United States Patent
Cullen et al.

(10) Patent No.: US 10,065,008 B2
(45) Date of Patent: Sep. 4, 2018

(54) DISCREET RESPIRATORY THERAPY SYSTEM

(71) Applicant: ResMed Limited, Bella Vista (AU)

(72) Inventors: Christopher Samuel Cullen, Bella Vista (AU); Damien Julian Mazzone, Bella Vista (AU); Muditha Pradeep Dantanarayana, Bella Vista (AU); Tumul Gupta, Bella Vista (AU); Joseph Debono, Bella Vista (AU); Andrew Sims, Bella Vista (AU); Justin John Formica, Bella Vista (AU); Aaron Samuel Davidson, Bella Vista (AU); Jeffrey Dean Jennings, Hendersonville, NC (US); David Alan Reed, Hendersonville, NC (US)

(73) Assignee: ResMed Limited (AU)

( * ) Notice: Subject to any disclaimer, the term of this patent is extended or adjusted under 35 U.S.C. 154(b) by 633 days.

(21) Appl. No.: 14/412,113

(22) PCT Filed: Jul. 5, 2013

(86) PCT No.: PCT/AU2013/000737
§ 371 (c)(1),
(2) Date: Dec. 30, 2014

(87) PCT Pub. No.: WO2014/005191
PCT Pub. Date: Jan. 9, 2014

(65) Prior Publication Data
US 2015/0335851 A1 Nov. 26, 2015

Related U.S. Application Data
(60) Provisional application No. 61/668,149, filed on Jul. 5, 2012.

(51) Int. Cl.
*A61M 16/20* (2006.01)
*A61M 16/00* (2006.01)
(Continued)

(52) U.S. Cl.
CPC .... *A61M 16/0066* (2013.01); *A61M 16/0051* (2013.01); *A61M 16/0057* (2013.01);
(Continued)

(58) Field of Classification Search
CPC .......... A61M 16/0051; A61M 16/0057; A61M 16/0063; A61M 16/0066; A61M 16/0069;
(Continued)

(56) References Cited

U.S. PATENT DOCUMENTS 1,848,232 A    3/1932  Swope et al.
3,611,801 A *  10/1971 Fagot .................. A61B 5/0816
                                                600/529
(Continued)

FOREIGN PATENT DOCUMENTS

EP    0512285 A1   11/1992
EP    0825103 A2    2/1998
(Continued)

OTHER PUBLICATIONS

Hastings Instruction Manual, "201/203 Series Flowmeters/Controllers", Aug. 2002.
(Continued)

*Primary Examiner* — Jackie Tan-Uyen T Ho
*Assistant Examiner* — Joseph D Boecker
(74) *Attorney, Agent, or Firm* — Lerner, David, Littenberg, Krumholz & Mentlik, LLP

(57) ABSTRACT

A device provides respiratory treatment such as for sleep disordered breathing and other respiratory conditions in a discreet configuration to provide a minimally invasive system. The system may include a flow pressurizer apparatus
(Continued)

configured to generate a pressurized flow of air through a small bore delivery conduit toward a patient interface. The system may further include a treatment compensator coupled with the fine bore delivery conduit. The treatment compensator may be configured at the patient interface to reduce pressure for patient inspiration. A processor may control adjustments to the pressure generated by the flow pressurizer apparatus.

27 Claims, 32 Drawing Sheets

(51) Int. Cl.
- A61M 16/08 (2006.01)
- A61M 16/10 (2006.01)
- A61M 16/12 (2006.01)
- A61M 16/06 (2006.01)
- A61M 16/16 (2006.01)

(52) U.S. Cl.
CPC ...... *A61M 16/0063* (2014.02); *A61M 16/026* (2017.08); *A61M 16/06* (2013.01); *A61M 16/0666* (2013.01); *A61M 16/0816* (2013.01); *A61M 16/0875* (2013.01); *A61M 16/1005* (2014.02); *A61M 16/12* (2013.01); *A61M 16/127* (2014.02); *A61M 16/20* (2013.01); *A61M 16/203* (2014.02); *A61M 16/204* (2014.02); *A61M 16/207* (2014.02); *A61M 16/209* (2014.02); *A61M 16/0069* (2014.02); *A61M 16/0683* (2013.01); *A61M 16/0866* (2014.02); *A61M 16/107* (2014.02); *A61M 16/109* (2014.02); *A61M 16/1055* (2013.01); *A61M 16/16* (2013.01); *A61M 16/201* (2014.02); *A61M 2016/0021* (2013.01); *A61M 2016/0027* (2013.01); *A61M 2016/0039* (2013.01); *A61M 2205/21* (2013.01); *A61M 2205/3344* (2013.01); *A61M 2205/3355* (2013.01); *A61M 2205/3553* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/75* (2013.01)

(58) Field of Classification Search
CPC .............. A61M 16/06; A61M 16/0666; A61M 16/0816; A61M 16/0866; A61M 16/0875; A61M 16/10; A61M 16/1005; A61M 16/12; A61M 16/127; A61M 16/20; A61M 16/201; A61M 16/202; A61M 16/203; A61M 16/204; A61M 16/209; A61M 2016/0021; A61M 2016/0027; A61M 2016/0039; A61M 2205/3355; A61M 2205/3351; A61M 2205/50; A61M 2205/502; A61M 2205/75
USPC ............ 128/204.18, 204.21, 204.24, 204.25, 128/204.26, 205.24, 205.25; 137/516.11–516.23
See application file for complete search history.

(56) References Cited

U.S. PATENT DOCUMENTS

| | | | |
|---|---|---|---|
| 3,717,147 A | 2/1973 | Flynn | |
| 3,733,898 A * | 5/1973 | Yamamoto | F15D 1/02 138/39 |
| 3,744,508 A * | 7/1973 | Hansen | G05D 16/08 137/115.06 |
| 3,906,996 A | 9/1975 | DePass et al. | |
| 4,098,285 A * | 7/1978 | Karing | G05D 7/014 137/115.1 |
| 4,393,869 A | 7/1983 | Boyarsky et al. | |
| 4,437,460 A * | 3/1984 | Glynn | A62B 9/025 128/204.26 |
| 4,827,964 A * | 5/1989 | Guido | A62B 7/14 128/204.21 |
| 5,036,847 A | 8/1991 | Boussignac et al. | |
| 5,245,995 A | 9/1993 | Sullivan et al. | |
| 5,485,850 A | 1/1996 | Dietz | |
| 5,676,342 A | 10/1997 | Otto et al. | |
| 5,704,354 A | 1/1998 | Preidel et al. | |
| 5,752,506 A | 5/1998 | Richardson | |
| 5,794,614 A | 8/1998 | Gruenke et al. | |
| 5,988,166 A * | 11/1999 | Hayek | A61H 31/02 128/202.12 |
| 6,253,764 B1 | 7/2001 | Calluaud | |
| 6,279,574 B1 | 8/2001 | Richardson et al. | |
| 6,332,463 B1 * | 12/2001 | Farrugia | A61M 16/00 128/204.18 |
| 6,349,724 B1 | 2/2002 | Burton et al. | |
| 6,354,291 B1 | 3/2002 | Brown et al. | |
| 6,363,933 B1 | 4/2002 | Berthon-Jones | |
| 6,398,739 B1 | 6/2002 | Sullivan et al. | |
| 6,401,714 B1 | 6/2002 | Giorgini | |
| 6,435,032 B1 | 8/2002 | Holloway et al. | |
| 6,615,831 B1 | 9/2003 | Tuitt et al. | |
| 6,634,356 B1 | 10/2003 | O'Dea et al. | |
| 6,635,021 B1 | 10/2003 | Sullivan et al. | |
| 6,708,690 B1 * | 3/2004 | Hete | A61M 16/0096 128/204.18 |
| 6,770,037 B2 | 8/2004 | Sullivan et al. | |
| 6,805,121 B1 * | 10/2004 | Flood | A62B 9/022 128/202.11 |
| 6,886,591 B2 | 5/2005 | Jennings | |
| 7,004,908 B2 | 2/2006 | Sullivan et al. | |
| 7,080,645 B2 | 7/2006 | Genger et al. | |
| 7,080,660 B2 | 7/2006 | Jennings | |
| 7,082,945 B2 * | 8/2006 | Lurie | A61M 16/06 128/203.11 |
| 7,141,021 B2 | 11/2006 | Sullivan et al. | |
| 7,314,046 B2 | 1/2008 | Schroeder et al. | |
| 7,331,345 B2 | 2/2008 | Haston | |
| 7,748,683 B1 | 7/2010 | Kelly | |
| 7,931,023 B2 | 4/2011 | Berthon-Jones et al. | |
| 8,011,380 B2 | 9/2011 | Califano et al. | |
| 8,025,053 B1 | 9/2011 | Prete et al. | |
| 8,166,974 B2 | 5/2012 | Pedemonte | |
| 8,215,336 B2 | 7/2012 | Jennings | |
| 8,365,728 B2 | 2/2013 | Hamilton et al. | |
| 9,669,172 B2 * | 6/2017 | Cullen | A61M 16/0066 |
| 2002/0096173 A1 * | 7/2002 | Berthon-Jones | A61M 16/00 128/204.23 |
| 2003/0015200 A1 | 1/2003 | Hansen | |
| 2003/0188586 A1 * | 10/2003 | Orleskie | G01F 1/34 73/861.61 |
| 2003/0192543 A1 | 10/2003 | Arnott | |
| 2003/0209246 A1 | 11/2003 | Schroeder et al. | |
| 2004/0016432 A1 | 1/2004 | Genger | A61M 16/00 128/204.18 |
| 2005/0004511 A1 * | 1/2005 | Figley | A61M 16/00 604/23 |
| 2005/0121035 A1 * | 6/2005 | Martin | B63C 11/2227 128/205.24 |
| 2006/0011198 A1 | 1/2006 | Matarasso | |
| 2006/0144401 A1 * | 7/2006 | Boelt | A61M 16/08 128/205.24 |
| 2006/0180149 A1 | 8/2006 | Matarasso | |
| 2008/0078395 A1 | 4/2008 | Ho et al. | |
| 2008/0307896 A1 * | 12/2008 | Ifft | G01F 1/42 73/861.61 |
| 2009/0044807 A1 | 2/2009 | Boussignac | |
| 2009/0151724 A1 * | 6/2009 | Wondka | A61M 16/0096 128/204.23 |
| 2009/0151728 A1 | 6/2009 | McConnell et al. | |

(56) References Cited

U.S. PATENT DOCUMENTS

| | | | |
|---|---|---|---|
| 2010/0011869 A1* | 1/2010 | Klosinski | G01F 1/42 73/700 |
| 2010/0043796 A1* | 2/2010 | Meynink | A61M 16/06 128/205.24 |
| 2010/0200084 A1* | 8/2010 | Lin | F16K 17/065 137/505.11 |
| 2010/0326533 A1 | 12/2010 | Mooney et al. | |
| 2011/0094518 A1 | 4/2011 | Cipollone et al. | |
| 2011/0315251 A1* | 12/2011 | Rampen | F16K 31/0696 137/561 R |
| 2012/0234323 A1* | 9/2012 | Connor | A61M 16/0066 128/204.21 |
| 2012/0298108 A1 | 11/2012 | Kane et al. | |
| 2012/0304993 A1 | 12/2012 | Nitta et al. | |
| 2013/0008444 A1* | 1/2013 | Chalvignac | A61M 16/0051 128/204.21 |
| 2013/0074842 A1 | 3/2013 | Boucher et al. | |
| 2013/0081616 A1* | 4/2013 | Tatkov | A61M 16/04 128/201.13 |
| 2013/0190632 A1* | 7/2013 | Baruch | A61B 5/4064 600/484 |
| 2013/0269693 A1 | 10/2013 | Neatrour et al. | |
| 2015/0107592 A1* | 4/2015 | Allum | A61M 16/0051 128/204.21 |
| 2015/0335851 A1 | 11/2015 | Cullen et al. | |

FOREIGN PATENT DOCUMENTS

| | | |
|---|---|---|
| EP | 1318307 A1 | 6/2003 |
| EP | 1655052 A2 | 5/2006 |
| EP | 1484242 B2 | 11/2010 |
| JP | 10-132137 | 5/1998 |
| WO | 0043060 A1 | 7/2000 |
| WO | 2000066920 A1 | 11/2000 |
| WO | 2011089491 A1 | 7/2011 |
| WO | 2012156885 A1 | 11/2012 |
| WO | 2013040198 A2 | 3/2013 |

OTHER PUBLICATIONS

Respironics, "WhisperFlow: CPAP system—Variable & Fixed User's Manual", Copyright 2008.

Wong et al., "Use of venturi entrainment to deliver nasal high flow oxygen", Crit Care & Shock (2010), vol. 13, No. 3, pp. 75-80.

Partial Search Report for Application No. PCT/AU2013/000737 dated Aug. 20, 2013.

Emerson Industrial Automation, Proportional Valves, 8202 / 8203 Series, Copyright 2013, <http://www.ascovalve.com/Applications/Products/ProportionalControl.aspx>.

Parker, Miniature Proportional Valves, VSP Series, Feb. 2013, <http://www.parker.com/literature/Literature%20Files/Precision%20Fluidics%20Division/UpdatedFiles/PPF_Proportional_Catalog.pdf>.

The Clippard Valve Equilibar, Proportional Valves, EVP Series Proportional Valves, Oct. 2012,<http://www.clippard.com/products/electronic-valve-proportional>.

South Bend Controls, Proportional Flow Control Valves Servoid, Aug. 2012,<http://www.sbcontrols.com/products.aspx/proportional-flow-control-valves>.

Bronkhorst USA, Control Valves, Dec. 2011, <http://www.bronkhorstusa.com/en/products/control_valves/>.

Teledyne Hastings Instruments, Instructional Manual, 201/203/205/207 Series Flow Meters/Controllers, Jul. 2011, <http://www.teledyne-hi.com/Manual/Flow/141-HFM-201_HFC-203_Manual.pdf>.

Equilibar Precision Pressure Control, Equilibar Back Pressure Regulator, Jun. 2011,<http://www.equilibar.com/back-pressure-regulator/introduction.asp>.

International Search Report and Written Opinion for Application No. PCT/AU2013/000737 dated Sep. 26, 2013.

Written Opinion of the International Preliminary Examination Authority for Application No. PCT/AU2013/000737 dated Jul. 4, 2014.

Teledyne Hastings Instruments, "Instructional Manual, 201/203/205/207 Series Flow Meters/Controllers", Jul. 2011, retrieved from http://www.teledyne-hi.com/Manuai/Fiow/141-HFM-201_HFC-203_Manual.pdf (as submitted by Applicant in IDS dated Oct. 7, 2014).

European Search Report for Application No. EP13813497 dated Dec. 21, 2015.

\* cited by examiner

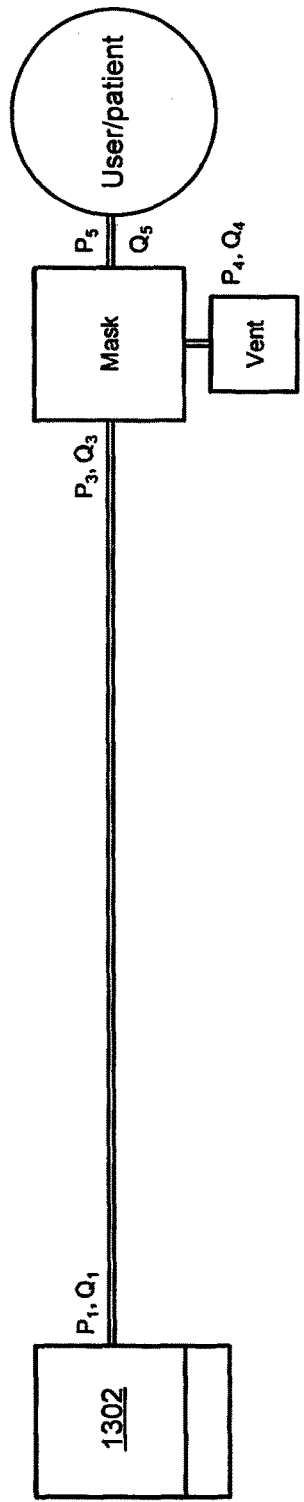
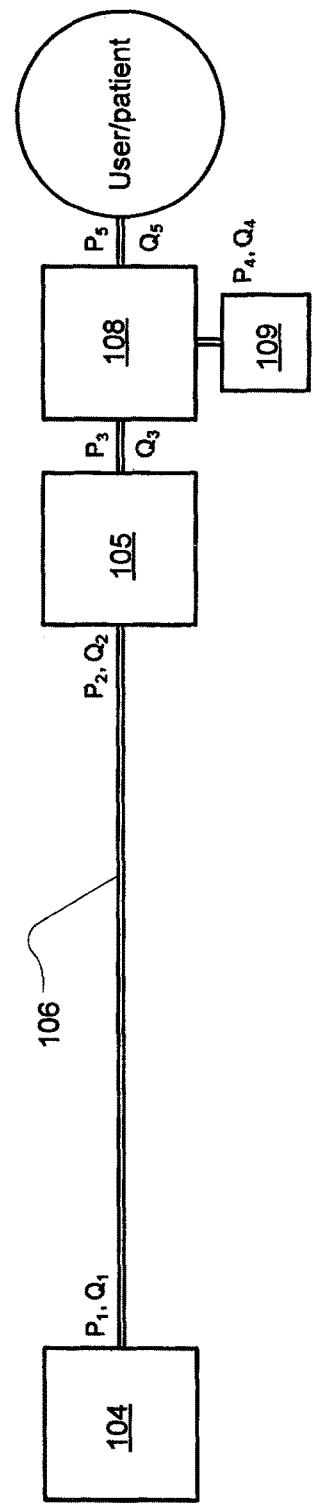
FIG. 13A
FIG. 13B

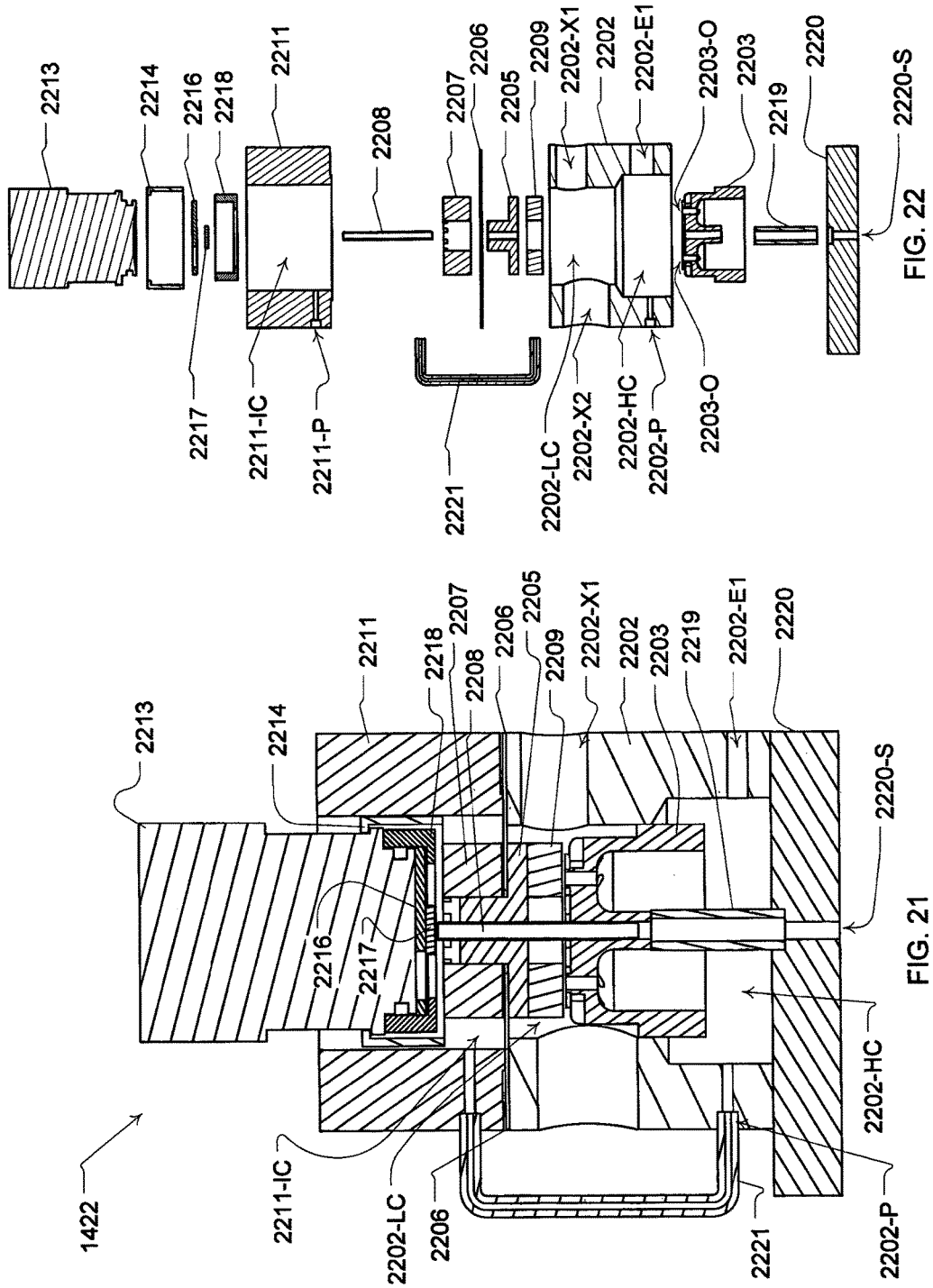

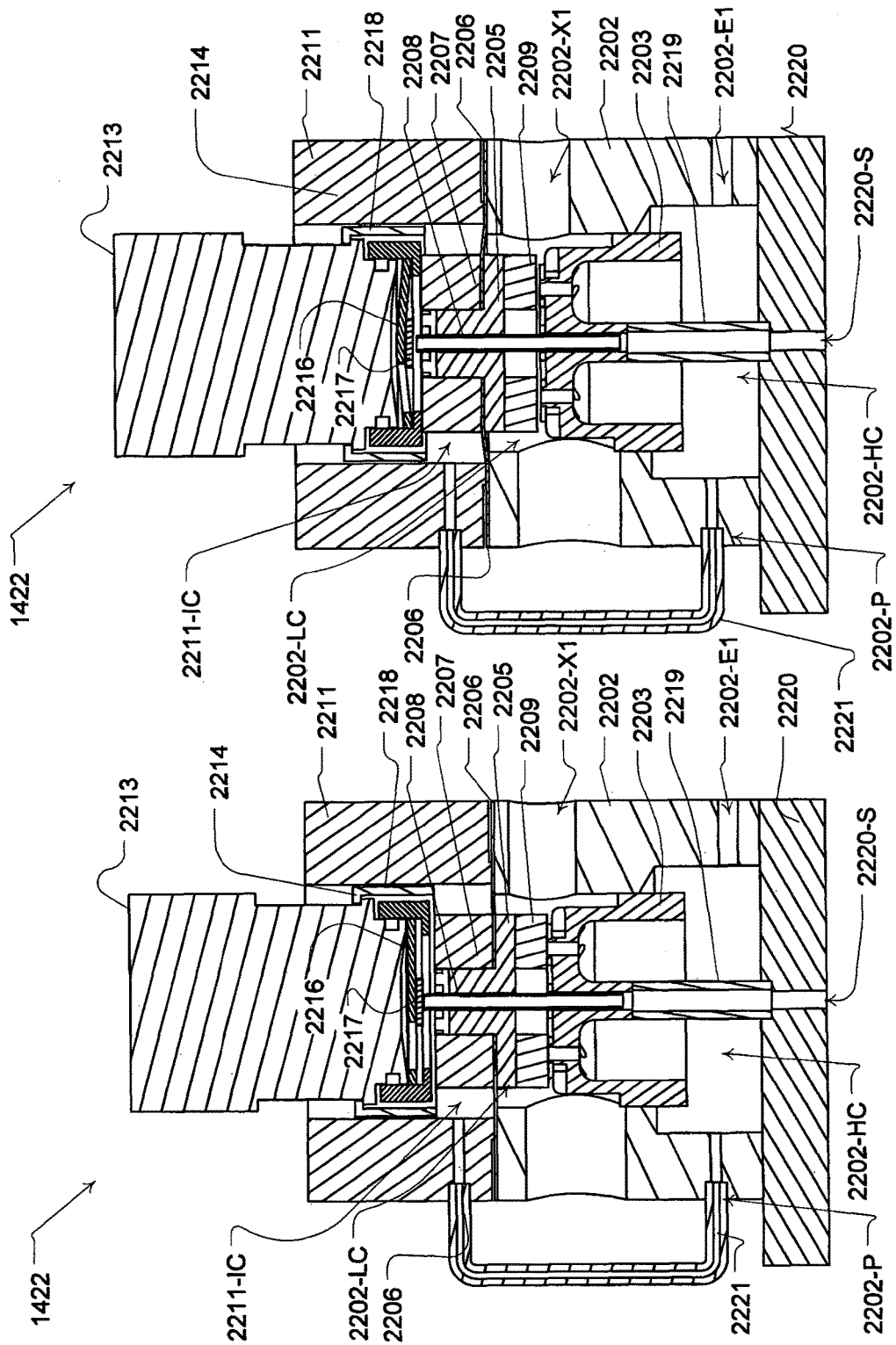

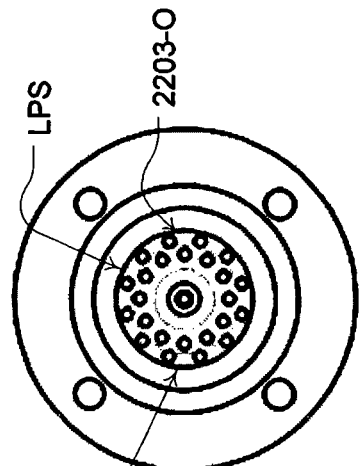
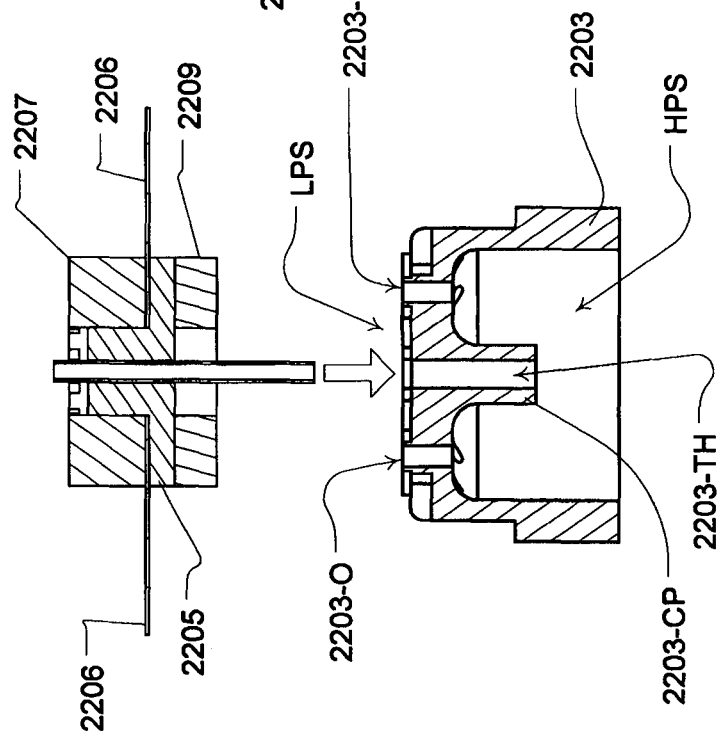
FIG. 24B
FIG. 24A

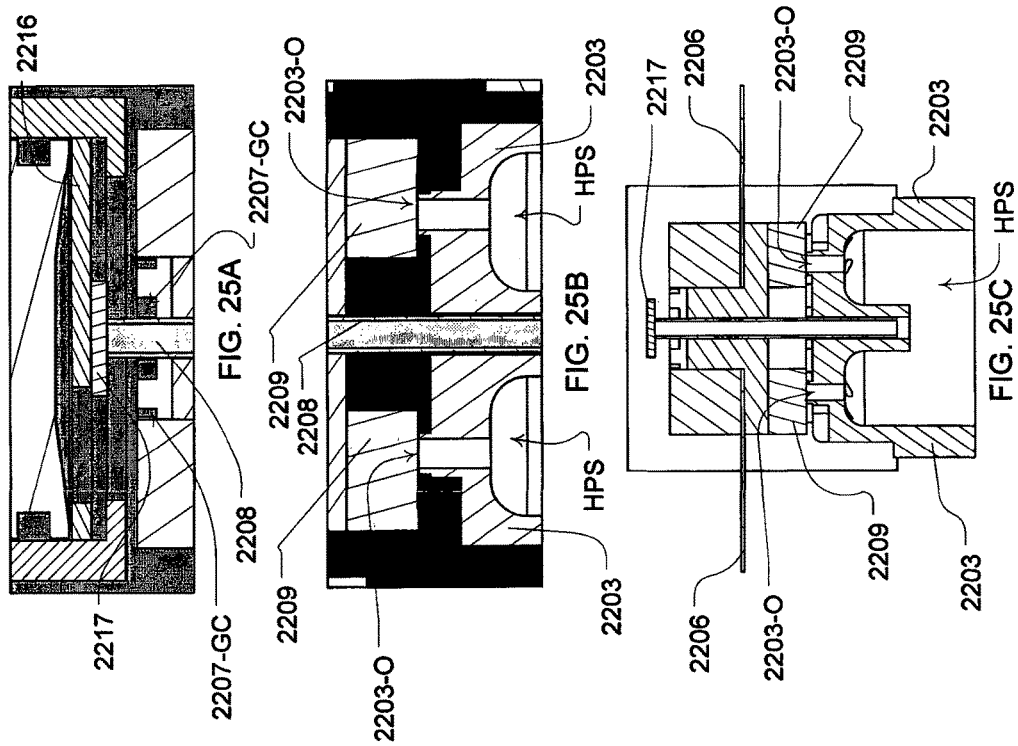
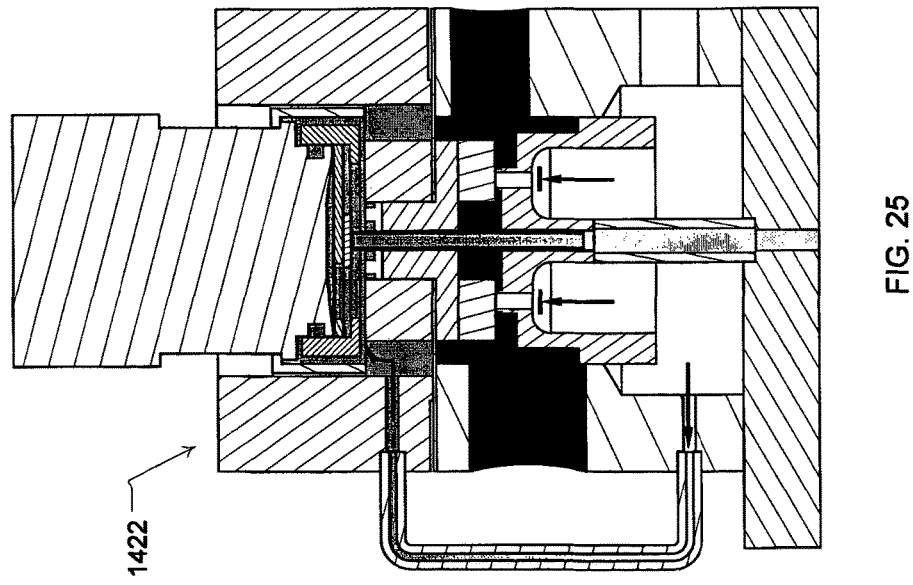
FIG. 25

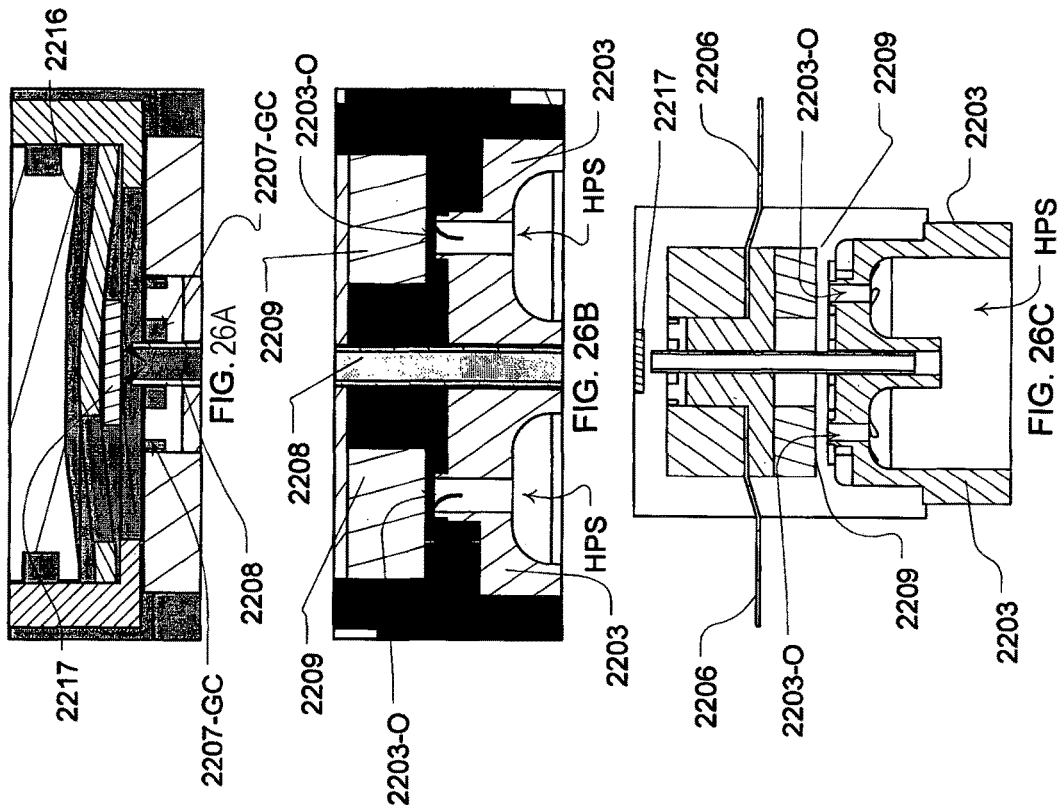
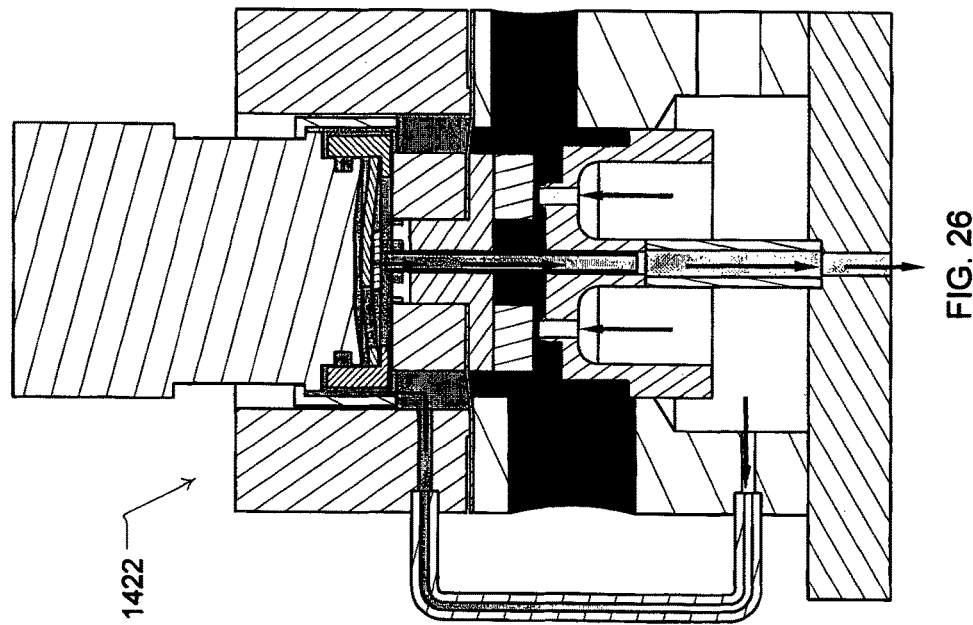

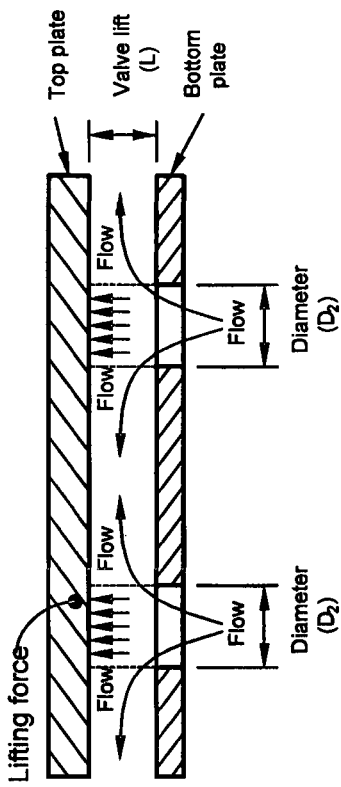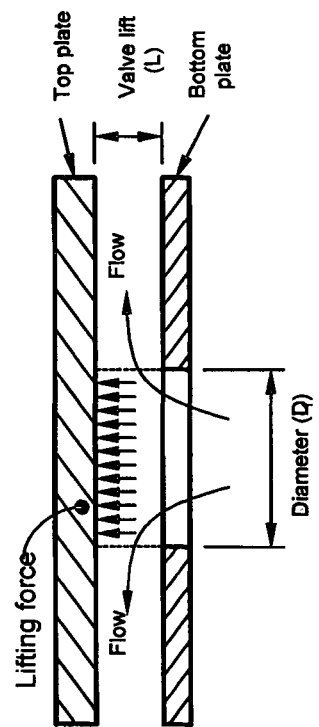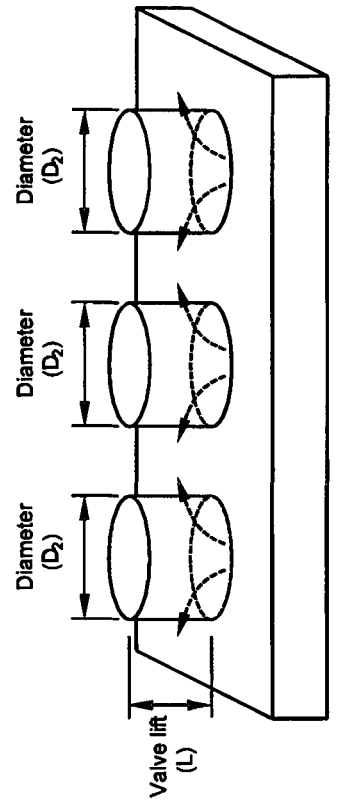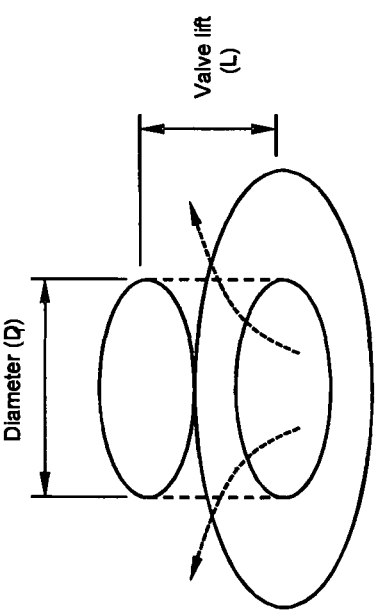
FIG. 27A
FIG. 27B

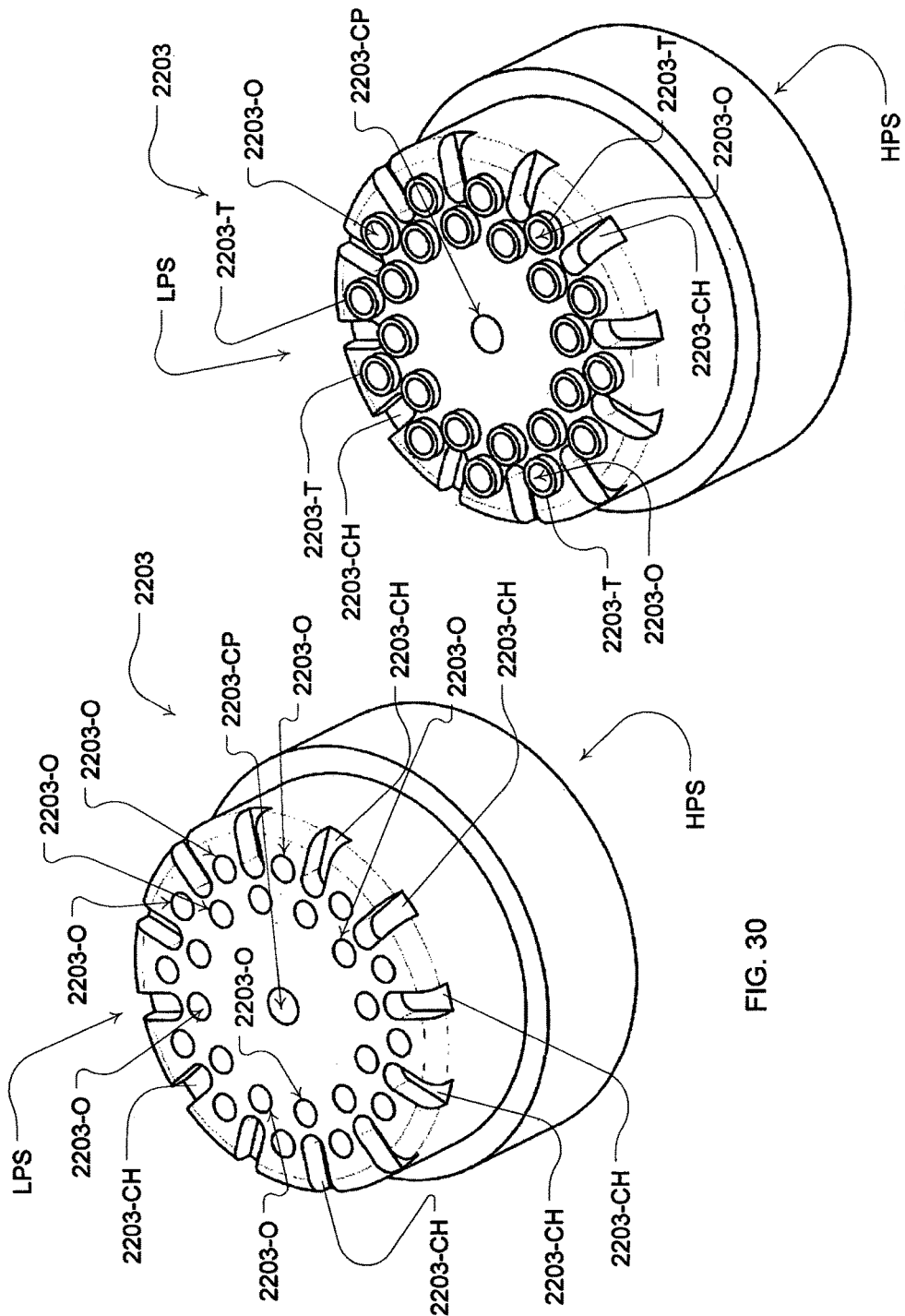

DISCREET RESPIRATORY THERAPY SYSTEM

CROSS REFERENCE TO RELATED APPLICATIONS

This application claims the benefit of the filing date of U.S. Provisional Patent Application No. 61/668,149 filed Jul. 5, 2012, the disclosure of which is hereby incorporated herein by reference.

FIELD OF THE TECHNOLOGY

The present technology relates to methods and apparatus for treatment of respiratory conditions such as the conditions related to sleep disordered breathing (SDB) (including mild obstructive sleep apnea (OSA)), allergy induced upper airway obstruction or early viral infection of the upper airway.

BACKGROUND OF THE TECHNOLOGY

Sleep is important for good health. Frequent disturbances during sleep or sleep fragmentation can have severe consequences including day-time sleepiness (with the attendant possibility of motor-vehicle accidents), poor mentation, memory problems, depression and hypertension. For example, a person with nasal congestion may snore to a point that it disturbs that person's ability to sleep. Similarly, people with SDB are also likely to disturb their partner's sleep. One known effective form of treatment for patients with SDB is nasal continuous positive airway pressure (nasal CPAP) applied by a flow generator (e.g., a servo-controlled blower via a connecting hose and patient interface. In some forms the supply of air at positive pressure is delivered to both the nose and mouth, such as with a mask. The positive pressure can prevent a collapse of the patient's airway during inspiration, thus preventing events such as snoring, apnoeas or hypopnoeas and their sequelae.

Such positive airway pressure may be delivered in many forms. For example, a positive pressure level may be maintained across the inspiratory and expiratory levels of the patient's breathing cycle at an approximately constant level. Alternatively, pressure levels may be adjusted to change synchronously with the patient's breathing cycle. For example, pressure may be set at one level during inspiration and another lower level during expiration for patient comfort. Such a pressure treatment system may be referred to as bi-level. Alternatively, the pressure levels may be continuously adjusted to smoothly change with the patient's breathing cycle. A pressure setting during expiration lower than inspiration may generally be referred to as expiratory pressure relief. An automatically adjusting device may increase the treatment pressure in response to indications of partial or complete upper airway obstruction or other sleep disordered breathing events. See U.S. Pat. Nos. 5,245,995; 6,398,739; 6,635,021; 6,770,037; 7,004,908; 7,141,021; 6,363,933 and 5,704,345. Treatment pressure produced by such CPAP devices typically range from 4 cm $H_2O$ to 22 cm $H_2O$ for treatment of OSA, depending on patient requirements. Treatment pressures for assisted ventilation can range of up to 32 cm $H_2O$.

Other devices are known for providing respiratory tract therapy. For example, Schroeder et al. describes an apparatus for delivering heated and humidified air to the respiratory tract of a human patient in U.S. Pat. No. 7,314,046, which was filed on 8 Dec. 2000 and assigned to Vapotherm Inc. Similarly, Genger et al. discloses an anti-snoring device with a compressor and a nasal air cannula in U.S. Pat. No. 7,080,645, filed 21 Jul. 2003 and assigned to Seleon GmbH.

It may be desirable to develop further methods and devices for treating respiratory conditions.

SUMMARY OF THE TECHNOLOGY

A first aspect of some embodiments of the technology is to provide methods and apparatus for directing pressurized air to a user or patient for a respiratory treatment of respiratory conditions.

Another aspect of some embodiments of the technology is to provide methods and apparatus for treating sleep disordered breathing.

A further aspect of some embodiments is to provide components of such technology with a configuration to improve comfort and patient compliance.

A still further aspect of some embodiments of such technology is to provide a system with minimal invasiveness.

In some embodiments of the technology, breathable gas may be directed toward an interface of a user or patient by implementation of fine bore delivery conduit.

Some embodiments of the present technology relate to a respiratory treatment system. The system may include a flow pressurizer apparatus configured to generate a pressurized flow of air through a fine bore delivery conduit toward a patient interface. The system may further include a treatment compensator coupled with the fine bore delivery conduit and configured at the patient interface to reduce the first pressure for patient inspiration to a second pressure above atmospheric pressure. The system may further include a processor configured to control adjustments to the first pressure generated by the flow pressurizer apparatus.

In some cases, the flow pressurizer apparatus may include a compressor configured to generate the pressurized flow of air. The flow pressurizer apparatus may include a step-up flow generator. Optionally, the flow pressurizer apparatus may further include a foundational flow generator. The foundational flow generator may be coupled with the step-up flow generator by a large bore delivery conduit.

In some cases, the system may include a Venturi chamber coupled to the patient interface. The Venturi chamber may be configured to entrain atmospheric air proximate to a nozzle coupled with an output of the fine bore delivery conduit. The system may also include a foam filter configured at an entrainment inlet of the Venturi chamber.

In some versions, the treatment compensator may include a pressure step-down chamber including a shuttle configured to move to reduce the first pressure at an input to the step-down chamber to the second pressure at an output of the step-down chamber. The shuttle may be activated by an air feed-back passage.

In some cases, the treatment compensator may include a pinch valve configured to selectively reduce a flexible passage of the treatment compensator to reduce the first pressure for patient inspiration. The pinch valve may include a solenoid actuator controlled by the processor as a function of a measure of pressure from a pressure sensor located proximate to an output of the pinch valve. The pinch valve may include an actuation lever. The lever may be configured proximate to a pressure feedback chamber having a membrane. Such a membrane may be configured to move the lever with changing pressure of the pressure feedback chamber.

In some cases, the pinch valve may include first and second pressure activation chambers adjacent to first and second membranes of the flexible passage. The first pressure activation chamber may be a feed-forward pressure chamber in gas communication with an input side of the flexible passage. The second pressure activation chamber may be a feedback pressure chamber in gas communication with an output side of the flexible passage. The first pressure activation chamber may include a release vent having a release vent gate.

In some cases, the system may further include a gas source input configured to couple with a supplemental oxygen gas source such that the input is configured to direct the supplemental oxygen to mix with the pressurized air.

Some embodiments of the present technology may relate to a method for control of a respiratory treatment apparatus. The method may include producing with a flow pressurizer system a flow of air through a fine bore tube toward a patient interface at a first pressure above atmospheric pressure. The method may further include compensating at the patient interface with a treatment compensator to reduce the first pressure for patient inspiration to a second pressure above atmospheric pressure. The method may also include controlling with a processor adjustments to the first pressure generated by the flow pressurizer system.

In some cases, the flow pressurizer apparatus may include a compressor configured to generate the pressurized flow of air. The flow pressurizer apparatus may include a step-up flow generator. The flow pressurizer apparatus may further include a foundational flow generator. The foundational flow generator may be coupled with the step-up flow generator by a large bore delivery conduit.

In some cases, the method may further include entraining atmospheric air with a Venturi chamber coupled to the patient interface such that entraining may be proximate to a nozzle coupled with an output of the fine bore delivery conduit. The entraining may be performed through a foam filter configured at an entrainment inlet of the Venturi chamber.

In some such cases, the treatment compensator may include a pressure step-down chamber including a shuttle moving to reduce the first pressure at an input to the step-down chamber to the second pressure at an output of the step-down chamber such that the shuttle may be activated by an air feed-back passage.

Optionally, the treatment compensator may include a pinch valve that selectively reduces a flexible passage of the treatment compensator to reduce the first pressure for patient inspiration. The pinch valve may include a solenoid actuator controlled by the processor as a function of a measure of pressure from a pressure sensor located proximate to an output of the pinch valve. The pinch valve may include an actuation lever. Optionally, the lever may be configured proximate to a pressure feedback chamber having a membrane such that the membrane may flex to move the lever with changing pressure of the pressure feedback chamber.

In some cases, the pinch valve may include first and second pressure activation chambers adjacent to first and second membranes of the flexible passage. The first pressure activation chamber may be a feed-forward pressure chamber in gas communication with an input side of the flexible passage. The second pressure activation chamber may be a feedback pressure chamber in gas communication with an output side of the flexible passage. The first pressure activation chamber may include a release vent having a release vent gate.

In some cases, a gas source input may be configured to couple with a supplemental oxygen gas source such that the input directs supplemental oxygen to mix with the pressurized air.

Additional features of the present respiratory technology will be apparent from a review of the following detailed discussion, drawings and claims.

BRIEF DESCRIPTION OF DRAWINGS

The present technology is illustrated by way of example, and not by way of limitation, in the figures of the accompanying drawings, in which like reference numerals refer to similar elements including:

FIGS. 13a and 13B are schematic diagrams respectively illustrating a conventional respiratory treatment system and a respiratory treatment system of the present technology.

FIG. 21 is a cross sectional side view of a valve-type treatment compensator suitable for some examples of the present technology;

FIG. 22 is an exploded view of the components of the treatment compensator of FIG. 21.

FIGS. 23A and 23B illustrated the compensator of FIG. 20 in closed and open states respectively;

FIG. 24A is a break out cross-sectional side view of a platen assembly and seat plate components of the compensator of FIG. 21;

FIG. 24B is an underside view of a seat plate component of the compensator of FIG. 21;

FIGS. 25, 25A, 25B and 25C illustrate operation of components of the compensator of FIG. 21 with respect to a closed position;

FIGS. 26, 26A, 26B and 26C illustrate operation of components of the compensator of FIG. 21 with respect to an open position;

FIGS. 27A and 27B illustrate gas transfer characteristics of the treatment compensator of FIG. 21 when implemented with a single orifice and a set of orifices such as between a platen seat and seat plate of the compensator of FIG. 22.

FIGS. 30 and 31 are perspective illustrations of different seat plates that may be suitable in some implementations of the compensator of FIG. 21;

FIG. 36c shows a schematic diagram of the electrical components of the PAP device of FIG. 36a.

DETAILED DESCRIPTION

Figure 1:
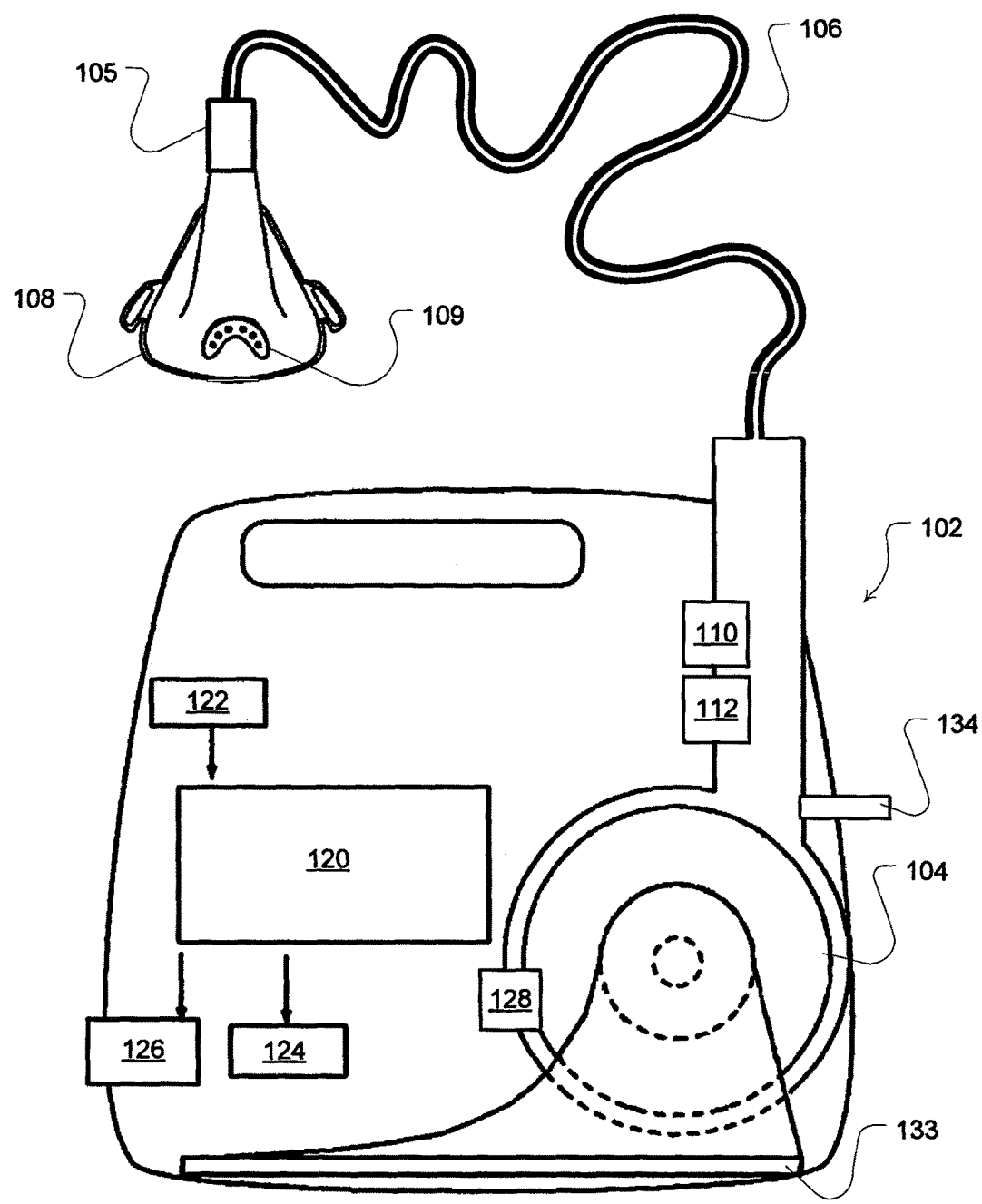
FIG. 1 shows example components of a discreet apparatus for treatment of the airway of a patient of the present technology.
Figure 2:
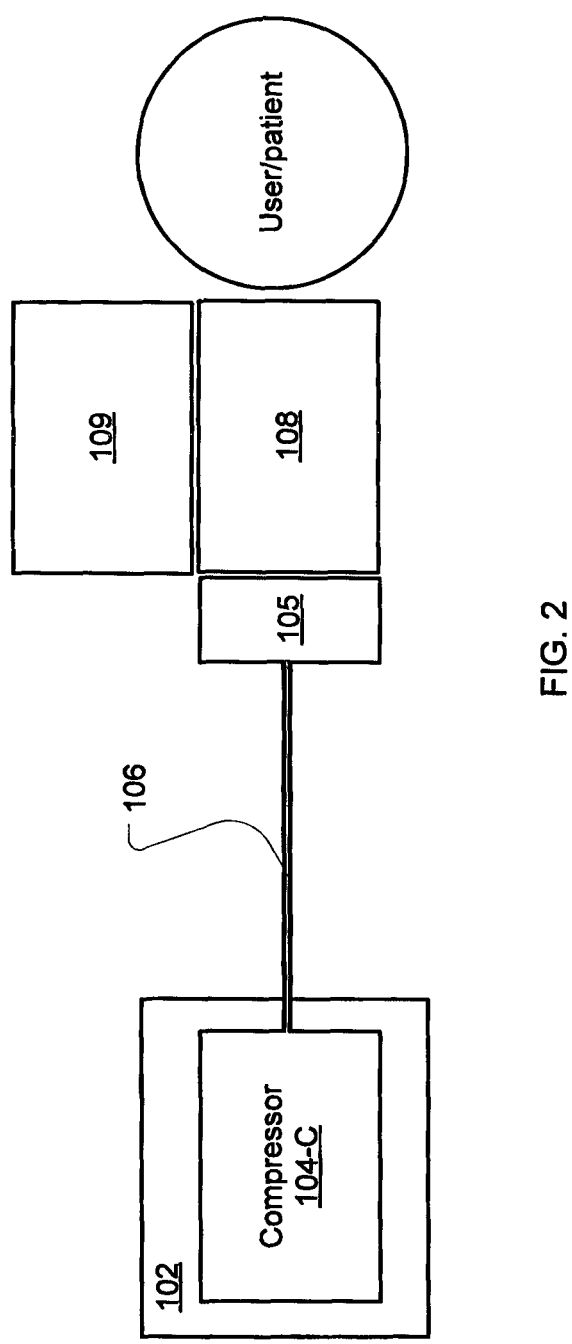
FIG. 2 is a schematic diagram of some of the elements of an example discreet system of the present technology.
Figure 3:
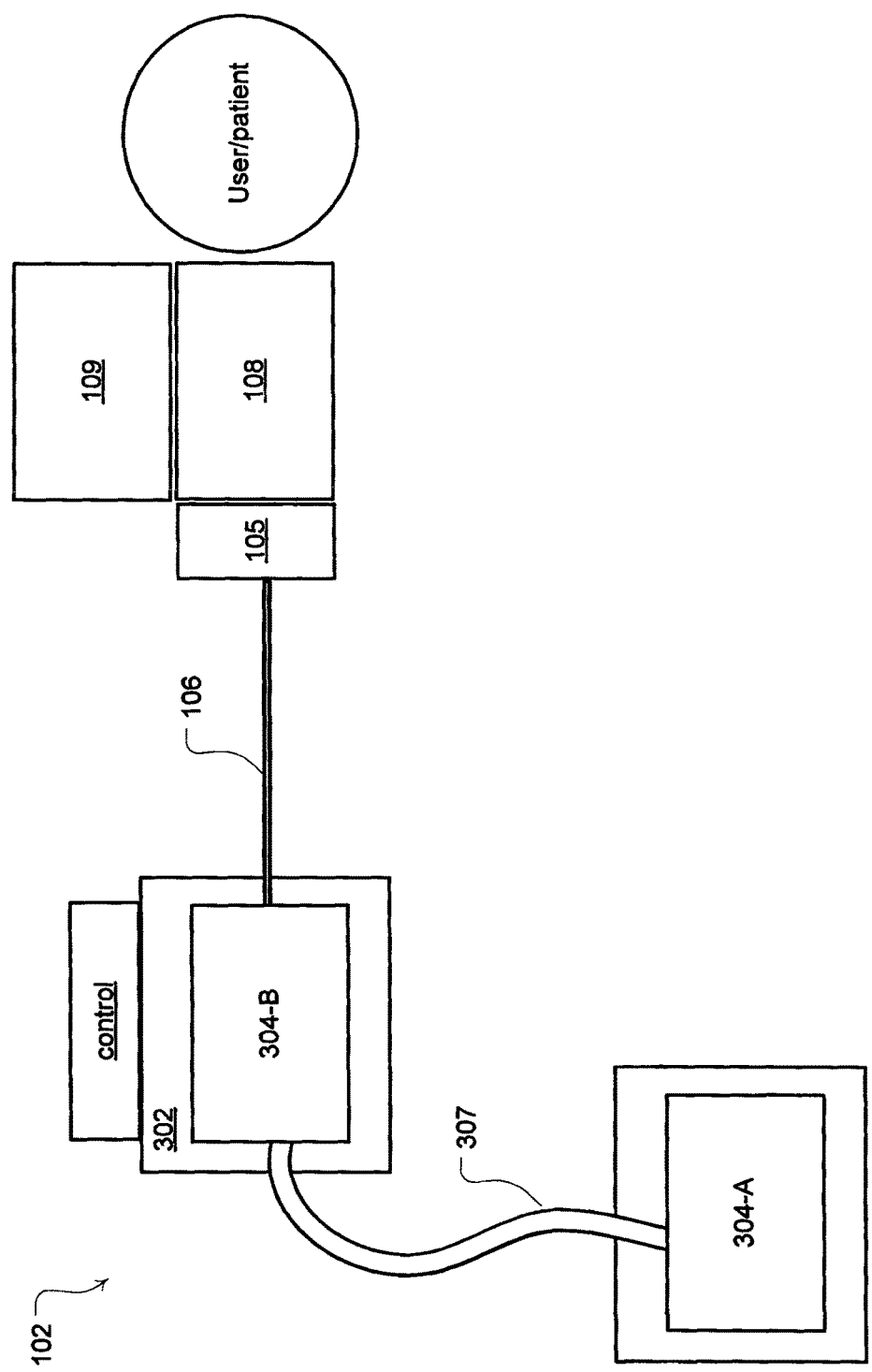
FIG. 3 is a schematic diagram of components of a system of the present technology that employs multiple flow generators.

Embodiments of the present technology may be implemented with an airway treatment device 102 or respiratory apparatus, such as a CPAP, APAP or ventilator apparatus, that may include some or all of the components illustrated in FIGS. 1, 2 and 3. For example, the airway treatment device 102 will typically include flow pressurizer apparatus 104, to generate a flow of air under pressure in a manner that increases the pressure of ambient air drawn in by the pressurizer. Thus, the flow pressurizer apparatus 104 may include an air inlet, which may have an optional filter 133. Optionally, a supplemental gas supply may be introduced through a supplemental gas port 134. Gas from such a distinct gas supply or gas source, such as oxygen, may mix with or supplement the pressurized air that is pressurized by the flow pressurizer apparatus. The airway treatment device 102 will typically include a user interface 122 such as one or more input buttons, switches or key press controls and a display 124, such as a light emitting diode (LED) display or liquid crystal display (LCD). An optional data interface 126 may be provided for wired or wireless data exchange between the controller of the apparatus and external systems.

A. Controller and Sensors

The airway treatment device 102 will typically include a controller 120, such as one or more processors. The controller may control the generated airway treatment based on signals from one or more optional sensors such a flow sensor 110 and/or a pressure sensor 112. The flow sensor generates a signal representative of the patient's respiratory flow and may include components of any intentional or unintentional leak. For example, flow associated with a nasal cannula or mask may be measured using a pneumotachograph and differential pressure transducer or similar device such as one employing a bundle of tubes or ducts to derive a flow signal f(t). Alternatively, a pressure sensor may be implemented as a flow sensor and a flow signal may be generated based on the changes in pressure. Although the flow sensor 110 is illustrated in a housing of the controller 120, it may optionally be located closer to the patient, such as in the patient interface 108 or an optional sense tube (not shown). Other devices for generating a respiratory flow signal may also be implemented.

One or more pressure sensors 112 may be positioned to provide information concerning the treatment pressure. The sensor may be positioned in various locations of the apparatus, such as in the mask or cannula, at an output of a compressor or blower etc., at or within any intermediary component of the flow path of the system (e.g., proximate to a treatment compensator as described in more detail herein or proximate to an outlet of a fine bore delivery tube.) Each pressure sensor will generate a pressure signal indicative of a pressure level at the location monitored by the sensor.

The signals from the various sensors (when present) may be sent to the controller 120 or processor, such as by wired signals or wireless signals (e.g., via Bluetooth transmissions). Optional analog-to-digital (A/D) converters/samplers (not shown separately) may be utilized in the event that supplied signals from the sensors are not in digital form and the controller is a digital controller.

Based on input signals from these sensors and/or other optional sensors, the controller 120 may in turn generate air flow or pressurization control signals. For example, the controller may generate an RPM request signal to control the speed of flow pressurizer apparatus 104 by setting a desired frequency or rotational velocity set point and comparing it with the measured condition of a frequency or velocity sensor 128. Alternatively, such changes may be based on determining a desired flow set point and comparing it with the measured condition of the flow sensor. Alternatively, such changes may be based on determining a desired pressure set point and comparing it with the measured condition of a pressure sensor. Typically, such changes to the motor speed are accomplished by increasing or decreasing supplied motor current with a servo based on determined differences between set and measured conditions such as in a closed loop feedback fashion and translating the difference to current. Thus, the processor or controller 120 may make controlled changes to the treatment delivered to the patient interface from the flow pressurizer apparatus 104.

The controller 120 or processor can typically be configured and adapted to implement particular control methodologies such as the methods described in more detail herein. Thus, the controller may include integrated chips, a memory and/or other control instruction, data or information storage medium. For example, programmed instructions encompassing such a control methodology may be coded on integrated chips in the circuits or memory of the device or such instructions may be loaded as software or firmware using an appropriate medium. With such a controller or processor, the apparatus can be used for many different airway treatment therapies, such as the pressure or flow treatments previously mentioned, by adjusting a pressure delivery equation that is used to set the flow pressurizer apparatus or the exhaust venting by an optional release valve (not shown). Thus, pressure may be controlled at desired levels as set by the switches or a user interface 122 of the device. The pressure may be kept substantially constant over the phases of respiration. In some embodiments, the generated pressure may be kept generally constant over the inspiratory cycle and provide some expiratory relief. Alternately, in some embodiments the pressure may be varied smoothly to replicate the patient's detected respiration cycle.

In some embodiments of the device, indications of upper airway obstruction determined by the controller are servo-controlled by varying the pressure. For example, a device in accordance with the technology may monitor the patient for signs of partial or complete upper airway obstruction, airway resistance, obstructive apnea, obstructive hypopnea, snoring etc. Upon detection of such events, and according to the severity and frequency of such events, the level of pressure is increased. In some embodiments, if the events are no longer detected, the level of pressure may be reduced.

In one embodiment, the controller may determine a tidal volume or other measure of inspired volume of air or gas over time by the patient during treatment. Such a determination may be used for setting the pressure or flow and/or analyzing conditions of the patient's airway or respiration for example, by controlling a pressure support (PS) to satisfy a target ventilation (e.g., a desired volume of air over a period of time).

B. Patient Interface

The airway treatment device 102 will also typically include a patient interface 108 such as nasal prongs or nasal cannula, nose mask, mouth and nose mask, nasal pillows etc. to direct the flow of air or breathable gas at the airway of a user of the device or a patient. The patient interface may be directly or indirectly coupled with the delivery conduit 106 to receive pressurized air from the conduit. In one form of such a patient interface, exhaust gas of the apparatus and/or expiratory gas from the patient's airway can be vented away from the patient interface with a vent 109, which may be a variable or fixed vent such as any of the vents described in U.S. Provisional Patent Application No. 61/558,158 filed on Sep. 13, 2011, the disclosure of which is incorporated herein by reference.

C. Breathable Gas Delivery Conduit

In response to the controller 120, the flow pressurizer apparatus 104 may generate varied flows or pressures for a patient treatment. Thus, it may be coupled so as to direct the breathable gas toward a patient interface through a gas delivery conduit 106. Such a conduit may be implemented with a length of fine bore tubing. A "fine bore" conduit may be understood herein to be a conduit having a gas channel with a cross-sectional area on the order of less than about 100 mm$^2$. The conduit may be defined by its internal or external diameter. For example, it may be a conduit having an air passage inside diameter in the range from about 2 mm to about 10 to 11 mm, preferably between 4 and 10 mm, and even more preferably between 7 and 9 mm. A further example conduit may be in the range of 4 mm to 12 outside diameter ("O.D.") tube, preferably between 6 and 11 mm O.D and more preferably between 8 and 10 mm O.D. tube. In some cases, multiple fine bore tubes (e.g., two 8 O.D. tubes or two 7 mm O.D. tubes) may serve as the delivery conduit. However, it will be understood that larger bore conduits may be implemented in some embodiments of the present technology. Such larger bore conduits may be, for example, 15 mm to 22 mm (either internal diameter or O.D.) tubing or other low impedance conduit. Since the gas delivery conduit 106 will typically lead to the patient interface 108, for purposes of comfort, the length of such a hose may be one or more meters (e.g., 1 to 6 Meters in length) to permit a comfortable distance from the flow pressurizer apparatus 104. In the case where the flow pressurizer apparatus 104 is intended to be wearable or in close proximity to the patient, the length of such a hose may be less than one meter (e.g. 1 m or less).

D. Flow Pressurizer Apparatus

As previously described, the breathable gas for treatment may be controlled to have various flow rates or pressure levels above atmospheric pressure to the patient interface for a patient treatment. Thus, the flow pressurizer apparatus, in response to the controller, may automatically adapt its treatment pressure based on detected conditions (e.g., SDB events like snoring, obstructive apnea, obstructive hypopnea, flow limitation, etc.). Moreover, the apparatus may be configured to produce pressures as a CPAP apparatus, Pressure Support apparatus, bi-level apparatus, APAP apparatus, etc. Such therapy pressures may typically be provided to the patient in the range of 4 to 22 cmH$_2$O for CPAP type devices and higher (such as 2-40 cmH$_2$O) for pressure support type devices. Similarly, the provided flows may be in a range of about 10 to about 40 liters/min for CPAP type devices and higher (such as 100-120 liters/min) for pressure support type devices. However, fine bore conduits have high impedance so can present significant issues in the control of treatment, due to the passage size restriction through which the breathable gas is directed. Thus, conventional flow generation system configurations may not be suitable for such implementations. Accordingly, the present technology may implement a flow pressurizer apparatus, such as with a set of flow generators as illustrated in FIG. 3 or a compressor as illustrated in FIG. 2. Such apparatus may be configured to generate air pressures significantly higher than the level required for patient therapy, and the levels typically provided by conventional devices, so as to overcome the limits (e.g., pressure drop) of the fine bore delivery conduit. Additional components for the airway treatment device 102 of the present technology herein may also be implemented to particularly compensate for restrictions associated with such conduits.

Thus, a flow pressurizer apparatus of the present technology may typically be configured to generate pressures to the fine bore conduit higher than the typical range for treatment of OSA or Pressure Support ventilation depending on the purpose of the device. Thus, a range of pressure generated by such a device may include the typical ranges for CPAP treatment of about 4-22 cm $H_2O$ or a typical range for pressure support treatment of about 2-40 cm $H_2O$, but may also be configured to generate additional high pressures exceeding those ranges depending on the different configuration of the delivery conduits (e.g., length, profile and diameter). Such highly increased pressure at the flow generator may thereby serve to increase the density of the breathable gas to levels that permit the airflow through the fine bore delivery conduit at relatively slow velocities (e.g., below typical velocities for such respiratory treatment apparatus). A subsequent reduction in pressure attributable to the treatment compensator at the patient interface may then permit a relatively higher (increased) velocity (e.g., a more typical velocity) of the gas to the patient interface as a result of gas expansion at the treatment compensator.

As illustrated in FIG. 2, the flow pressurizer apparatus 104 may include a compressor 104-C. In a typical embodiment, the compressor may include a motor (not shown). The motor may have an array of airfoils such as in an axially compressor configuration. The motor may also have an impeller such as in a radial compressor configuration. Other compressor configurations may also be implemented, such as one based on a piston configuration. The compressor may be configured to generate the pressures necessary to overcome the impedance restrictions of the fine bore delivery conduit.

Alternatively, as illustrated in FIG. 3, the flow pressurizer apparatus 104 may be formed by a set of flow generators 304-A, 304-B. In some such embodiments, the flow generators may be formed by a servo-controlled blower or fixed speed blower. The blower may include a motor with an impeller within a volute. Such a system configuration may include an initial stage flow generator 304-A and a step-up flow generator 304-B. The two flow generators may be coupled by a junction delivery conduit 307, such as a large bore conduit or other low impedance delivery conduit (e.g., 14-22 mm O.D. conduit or greater). The pressurized output flow of air from the initial stage flow generator 304-A is directed through the junction delivery conduit 307 to the input of the blower of the step-up flow generator 304-B. The two flow generators can provide a multi-stage pressurization configuration to provide the necessary pressures to overcome the impedance of the fine bore delivery conduit 106. For example, the initial stage flow generator 304-A may be controlled to dynamically adjust treatment pressure to the different levels of pressurization to treat SDB and/or to change to provide an expiratory pressure relief in synchronization with detected patient respiration while the step-up flow generator 304-B may provide a fixed pressure necessary to overcome the pressure drop associated with the fine bore conduit. Alternatively, the initial stage flow generator 304-A may be configured to provide a fixed level of pressure that may be associated with the pressure drop of the fine bore tube and the step-up flow generator 304-B may be controlled to dynamically adjust the pressure suitable for treatment (e.g., pressure support adjustments, bi-level adjustments, treatment pressure increases for expiratory pressure relief, automatic treatment pressure adjustments (increases or decreases) based on detected sleep disordered breathing events or lack thereof).

In some such embodiments, a controller 120 may be located within the initial stage flow generator 304-A, the step-up flow generator 304-B or both. For example, in some embodiments, the controller 120, as well as the user interface 122 and display 124 may be included in the step-up flow generator 304-B. A user or patient may then operate both flow generators by setting the controls of the step-up flow generator 304-B. In some such examples, the flow generator 304-B may have a small or mini size so as to be capable of placement on the patient's bed side table. The flow generator 304-A may be sized to be positioned under the patient's bed or otherwise out of sight. The flow generator 304-A may supply constant air to mini flow generator 304-B by for example, a 15 mm or 22 mm tube, or tube with low impedance. The mini flow generator 304-B may receive data from a sensor located on the patient interface 108 or mask. For example, the sensor may receive the pressure of the air at the mask. Based on the data from the sensor, mini flow generator 304-B may adjust the flow and/or pressure to the mask to ensure the patient is receiving a constant pressure at the mask. Mini flow generator 304-B may then be connected to the mask by a fine bore tube (e.g., a tube in the range of 6-9 mm, such as a 7 mm tube).

In some embodiments, the patient or user can control the system by buttons or other user controls on the mini flow generator 304-B as this may be in a convenient location. Of course, in some embodiments, all of the controls may be on the other flow generator 304-A. Alternatively, some controls may be positioned on the mini flow generator 304-B (such as frequently used controls for humidification and temperature (i.e., when a humidifier and water and/or tube heaters are implemented with any of the flow generators), and on-off switching) and other controls may be on the flow generator 304-A. In some such cases, a bus or interface may be provided for purposes of data communication between the flow generators.

In some versions of the configuration of FIG. 3, the initial stage flow generator 304-A can be implemented by a powerful and/or large footprint flow generator capable of generating the highest pressures as required to meet the pressure levels described herein to overcome the impedance issues of the fine bore tube. In such a case, the initial stage flow generator 304-A provides the high pressure to the flow generator 304-B via the junction delivery conduit 307. In this case, the flow generator 304-B may be configured to regulate or control regulation of the patient's pressure requirements to the high pressure input side of a treatment compensator that is described in more detail herein. This will permit the treatment compensator to be supplied with an ample reservoir of pressure at the treatment compensator's high pressure input side to allow the treatment compensator to satisfy the patient's pressure requirements at the low pressure output side of the treatment compensator so as to supply a suitable pressure to the patient or patient interface.

E. Treatment Pressure Compensation

Accordingly, some embodiments of the present technology may implement a treatment compensator, such as treatment compensator 105 located at, or near, the patient interface. The treatment compensator is configured to reduce the high pressures of the air treatment emanating from the fine bore delivery conduit 106 so that the output levels of pressure may be lowered to be suitable for inspiration by the user or patient with the patient interface for the pressure treatments described herein. Thus, in a typical embodiment, an air or breathable gas input to the treatment compensator 105 will be from an output of the fine bore conduit 106 and an output of the treatment compensator will lead to an input of the patient interface 108. Examples of such apparatus may be considered in reference to FIGS. 4 through 10.

Figure 4:
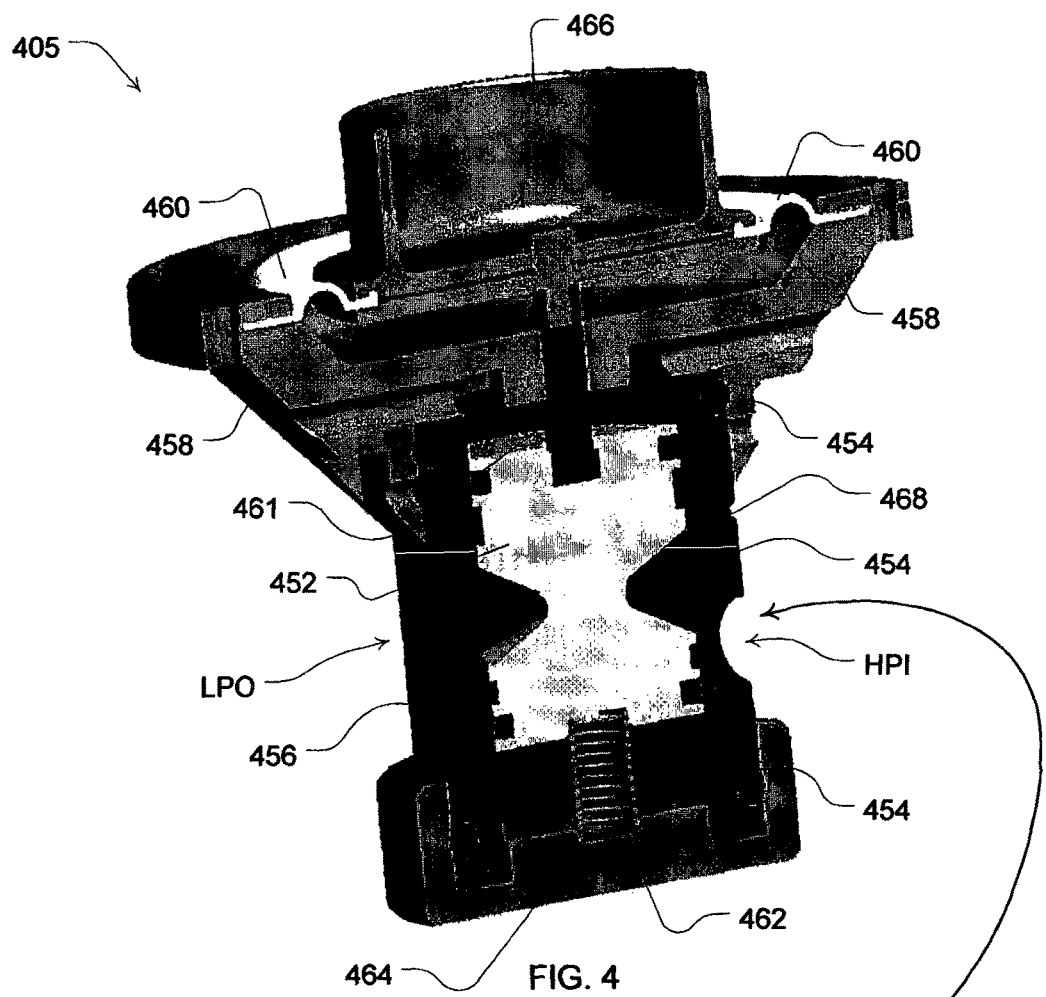
FIG. 4 is a cross sectional illustration of a treatment compensator in some embodiments of the present technology.
Figure 4A:
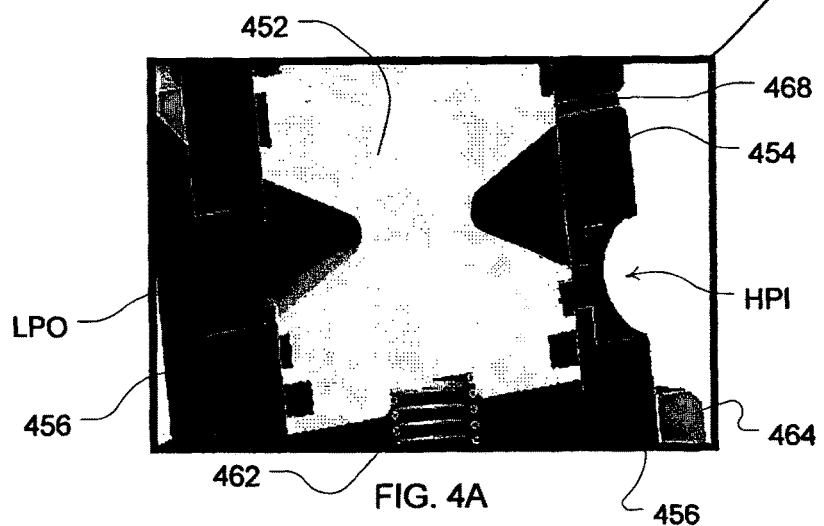
FIG. 4A is an enlarged cross section illustration of a portion of the treatment compensator of FIG. 4.

The treatment compensator 405 in the example of FIGS. 4 and 4A includes a mechanical shuttle 452, such as one with an hourglass shape that provides a central area for gas passage. The shuttle may move within a shuttle chamber 454 that may be formed by a cylinder 456. The cylinder 456 includes a high pressure input HPI, such as from an output of a fine bore conduit 106, and a low pressure output LPO, such as for providing treatment pressure to the patient interface or mask. Operational movement of the shuttle permits a step down or reduction of the pressure within the chamber 454 with respect to the high pressure input. In this regard, movement of the shuttle permits a greater or lesser size of an opening of the high pressure input HPI to the shuttle chamber 454.

Movement of the shuttle may be controlled by pressure in a control chamber 458. The control chamber 458 may expand and contract with pressure in accordance with a pressure of the low pressure output LPO that is directed to the control chamber 458 by a feedback passage (not shown) from the low pressure output to the control chamber 458. A control chamber diaphragm 460 permits expansion and contraction of the chamber. A shuttle rod 461 couples the shuttle and control chamber top 466 to permit a complementary movement of the top of the control chamber and the shuttle when the control chamber expands or contracts.

The shuttle may be biased by one or more biasing elements that provide biasing forces. Such biasing forces may serve to adjust the response of the shuttle to pressure in the control chamber 458 such that the compensator may be configured to reduce the high pressure to a desired degree such as to permit a fixed step down in pressure from the high pressure input side to the low pressure output side. For example, a shuttle spring 462 may be implemented between a base side of the shuttle and a base cap 464 of the cylinder 456. Similarly, a weight or other spring element may be applied at the control chamber top 466. Optionally, one or more of such biasing elements may be adjustable so as to permit adjustment of the force for or during use. For example, a screw may be implemented to increase or decrease a biasing force of a spring applied at the top. Optionally, an electro-mechanical actuator, such as a stepper motor having a threaded rod coupled to rotate with the rotor, may be implemented for automated controlled adjustments to the biasing force at the top 466. A leak passage or opening 468 from the shuttle chamber to atmosphere may be provided to permit an escape of air or gas that may be trapped in the shuttle chamber.

Figure 5:
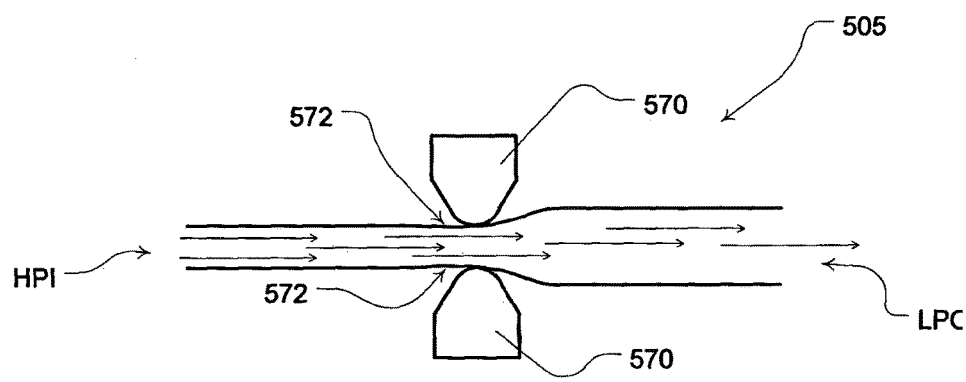
FIGS. 5 and 6 illustrate operation of a pinch valve version of a treatment compensator in some embodiments of the present technology.
Figure 6:
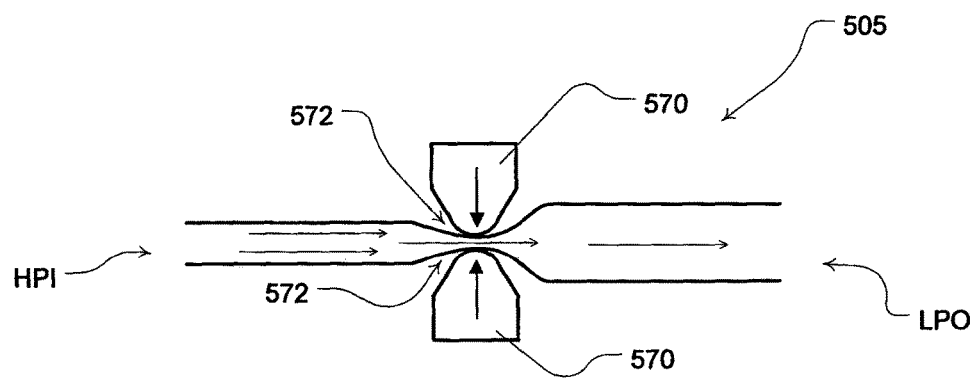

The treatment compensator 505 in the examples of FIGS. 5 and 6 may be configured as a pinch valve. The pinch valve may include one or more pinch elements 570. The pinch elements 570 may be configured to ply a force against a flexible portion 572 of a passage of the valve. For example, as illustrated in FIG. 6, a movement force of one of more of the pinch elements may constrict an opening of the passage of the valve with the flexible portion 572. As a result, a step down in pressure from a high pressure input HPI side and a low pressure output LPO side may be achieved. In such a case, the low pressure input side may be coupled with a fine bore conduit 106 as previously described while the low pressure output side may be coupled with a patient interface 108.

Figure 7:
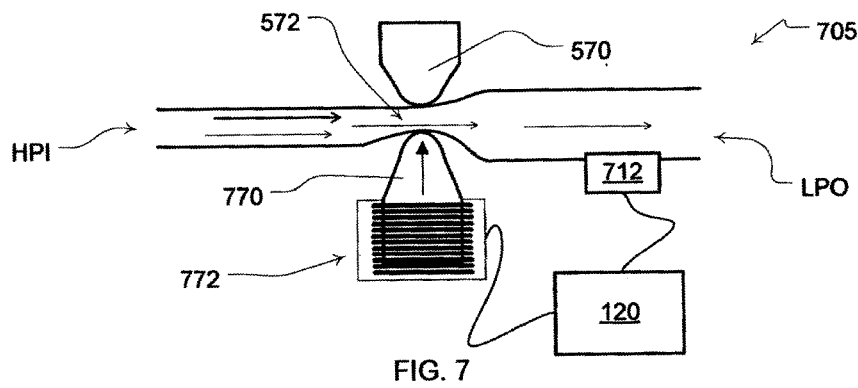
FIG. 7 is a cross sectional view of a pinch valve based treatment compensator with an electro-mechanical actuator.

While the pinch valve may be manually set for a fixed step down of pressure, some embodiments may be implemented to provide automated control for dynamically setting the restriction of the pinch valve and thereby dynamically setting the step down in pressure. Some examples are illustrated with reference to the treatment compensator 705, 805 of FIGS. 7 and 8 respectively. In FIG. 7, one or more of the pinch elements 570 may be formed by an actuator, such as an electro-mechanical actuator. For example, the pinch valve may include a solenoid 772 as a pinch element. The solenoid, including one or more field coils, may be controlled by a controller or processor, such as controller 120 so as to change a position of its pinch element 770 and thereby selectively increase or decrease the passage size of the valve. The controller may be responsive to changes in measured pressure detected by a pressure sensor 712. In such a case, the pressure sensor may be located to measure pressure within a gas passage of the low pressure output LPO of the pinch valve. When only one pinch element is configured for movement, the opposing pinch element 570 may serve as a stop.

Figure 8:
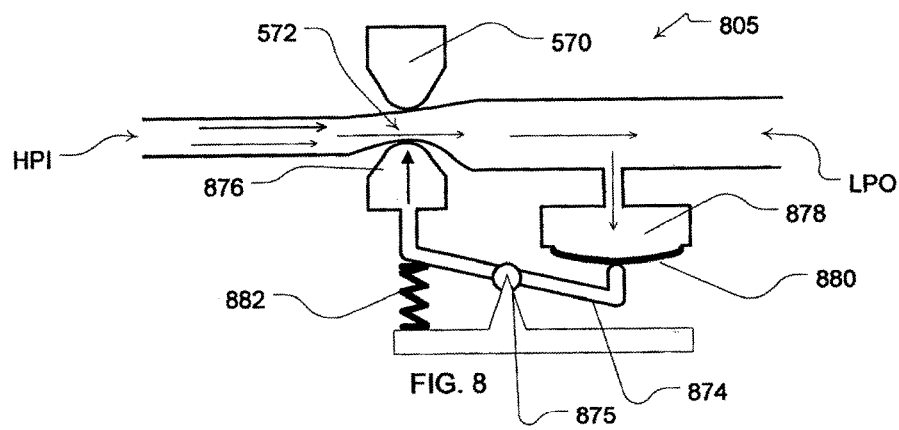
FIG. 8 is a cross sectional view of an pinch valve based treatment compensator with a pneumatic-mechanical actuator.

In some embodiments, the pinch valve may be dynamically adjusted by pneumatic forces. For example, as illustrated in FIG. 8, the pinch valve may include a lever 874, such as one on a pivot 875. The pinch element 876 may be a portion of the lever 874 or coupled therewith. A lever activation chamber 878 such as one providing a feed-back pressure from a low pressure output of the pinch valve may serve to actuate the lever by expansion or contraction of a flexible membrane 880 of the chamber in contact with the lever. Optionally, the lever may be biased, such as by a lever spring 882. Setting of the force of the lever spring may set a preload on the lever to change the set step down of pressure of the valve. Expansion of the chamber 878 with increasing pressure of the low pressure output side LPO may then serve to pinch the pinch valve to decrease the passage of the pinch valve and thereby decrease the pressure of the low pressure output side LPO. Contraction of the chamber, 878 with decreasing pressure of the low pressure output side LPO may then serve to open the pinch valve to increase the passage of the pinch valve and thereby increase the pressure of the low pressure output side LPO of the valve.

Figure 9:
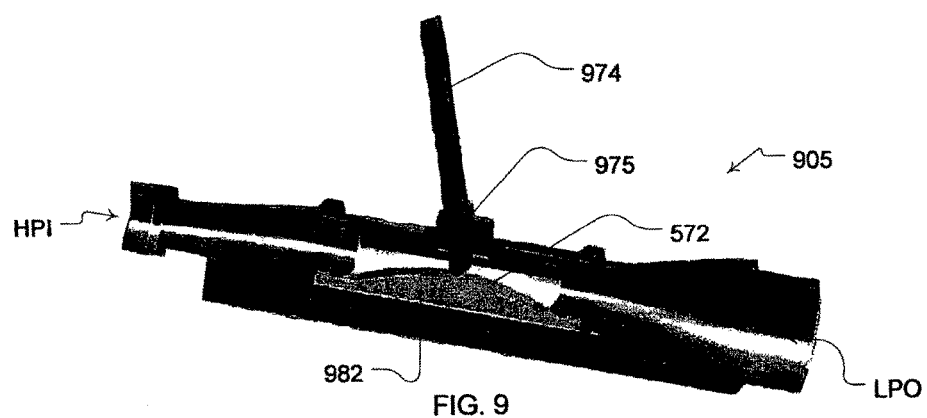
FIG. 9 is a cross-sectional perspective view of another example of a treatment compensator suitable for some embodiments of the technology.

In the example of FIG. 9, the pinch valve of the treatment compensator 905 includes a flexible passage 572 between the high pressure input HPI side and the low pressure output LPO side that is formed by a flexibly resilient cushion 982. The cushion may be in contact with a cushion actuation lever 974 that may swing on a pivot 975. Movement of the lever in one direction may compress the cushion to increase the passage size of the valve. Movement of the lever in an opposite direction may release the cushion from the force of the lever so that the cushion may resiliently expand to reduce the size of the flexible passage. In this way, the size of the flexible passage may be varied to selectively increase or decrease the step down of pressure between the input and output sides of the valve. Optionally, the lever may be actuated by various components. For example, it may be coupled with a solenoid or a screw drive motor to change the position of the lever.

Figure 10:
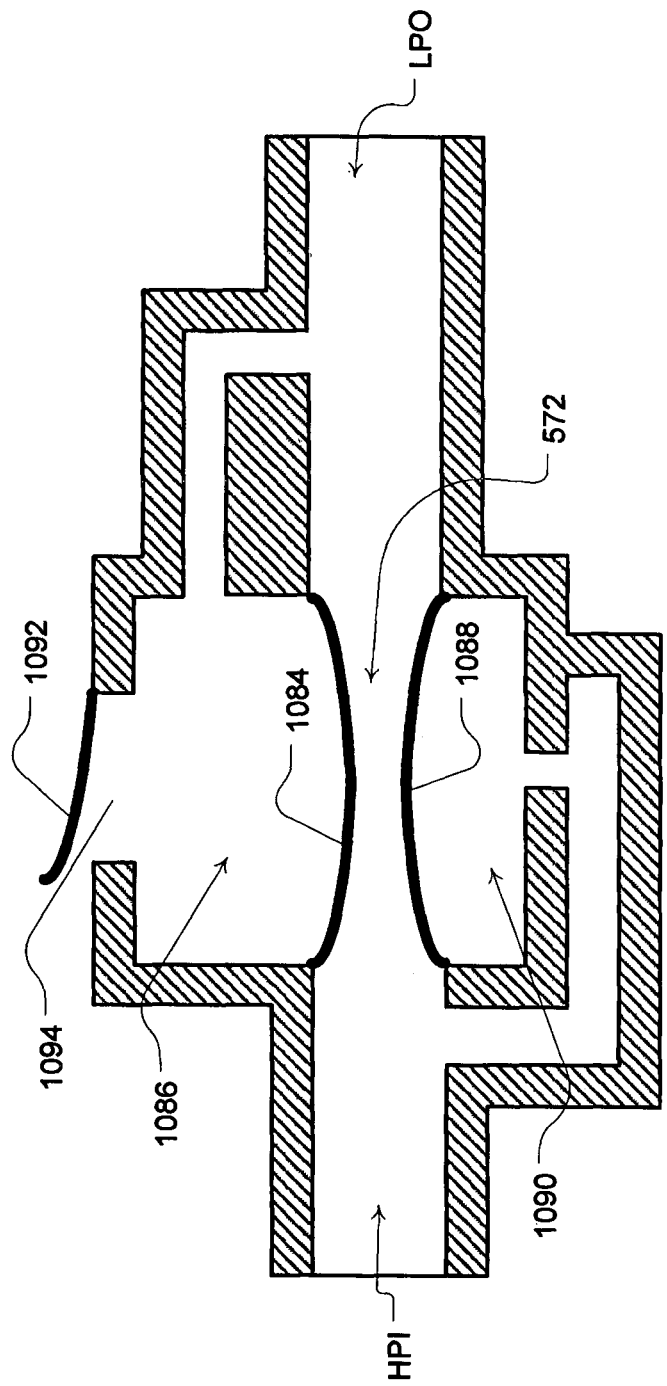
FIG. 10 is an illustration of an example pneumatic valve treatment compensator that may be employed in some embodiments.

In the example treatment compensator of FIG. 10, pneumatic control also serves to adjust the passage size of the pinch valve between the high pressure input HPI side and the low pressure output LPO side. In this version, no pinch elements are employed. Rather, constriction and expansion of the flexible portion 572 of the valve is achieved with multiple pressure chambers, such as a pressure feed-back chamber and a pressure feed-forward chamber. In this embodiment, a flexible membrane 1084 of a pressure feed-back chamber 1086 forms the flexible portion 572 of the valve. Similarly, the flexible membrane 1088 of a pressure feed-forward chamber 1090 also forms the flexible portion 572 of the valve. Optionally, the pressure feed-back chamber 1086 may include a release vent gate 1092 for a release vent 1094 opening. Pressure of the high pressure input side of the valve serves to adjust expansion or contraction of the membrane 1088 of the pressure feed-forward chamber 1090. Similarly, pressure of the low pressure output side of the valve serves to adjust the membrane 1084 of the pressure feedback chamber 1086. The release vent gate may be biased to open and release pressure of the feedback chamber in event of an increased pressure condition in the pressure feedback chamber 1086. The balancing of pressure forces of the chamber may permit a controlled compensation of the step down of pressure in the valve from the high pressure input HPI side to the low pressure output LPO side.

F. Venturi Chamber

Figure 11:
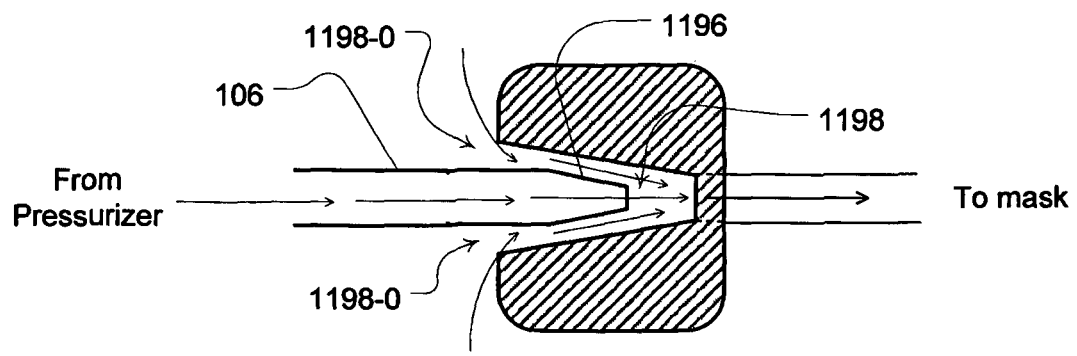
FIG. 11 is a cross-sectional perspective view of an example Venturi coupler for a fine bore delivery conduit of the present technology.

Some embodiments of the present technology may employ a Venturi chamber. Examples of such a feature may be considered in reference to the illustrations of FIGS. 11 and 12. Such a feature may permit an increase in the air supplied to a patient when a fine bore delivery conduit 106 is employed. Thus, the chamber may be implemented as a coupler for a fine bore delivery tube and/or a patient interface. For example, the fine bore conduit 106 may direct a flow of high pressure air to a nozzle 1196 having a tapered end. The nozzle may be positioned within or coupled to the Venturi chamber 1198 so as to have a gap of the chamber surrounding portions of the nozzle. The gap(s) of the chamber lead to a chamber opening 1198-O to atmosphere. During operation, the high pressure flow, accelerated by the taper of the nozzle, may entrain air from atmosphere into the Venturi chamber through the chamber openings 1198-O so as to increase the quantity of air entering the chamber and thereby increasing the air flowing toward a patient for treatment. Optionally, a foam filter 1199 may cover the chamber openings 1198-O to filter air and/or reduce noise at the openings (see FIG. 12).

Figure 12:
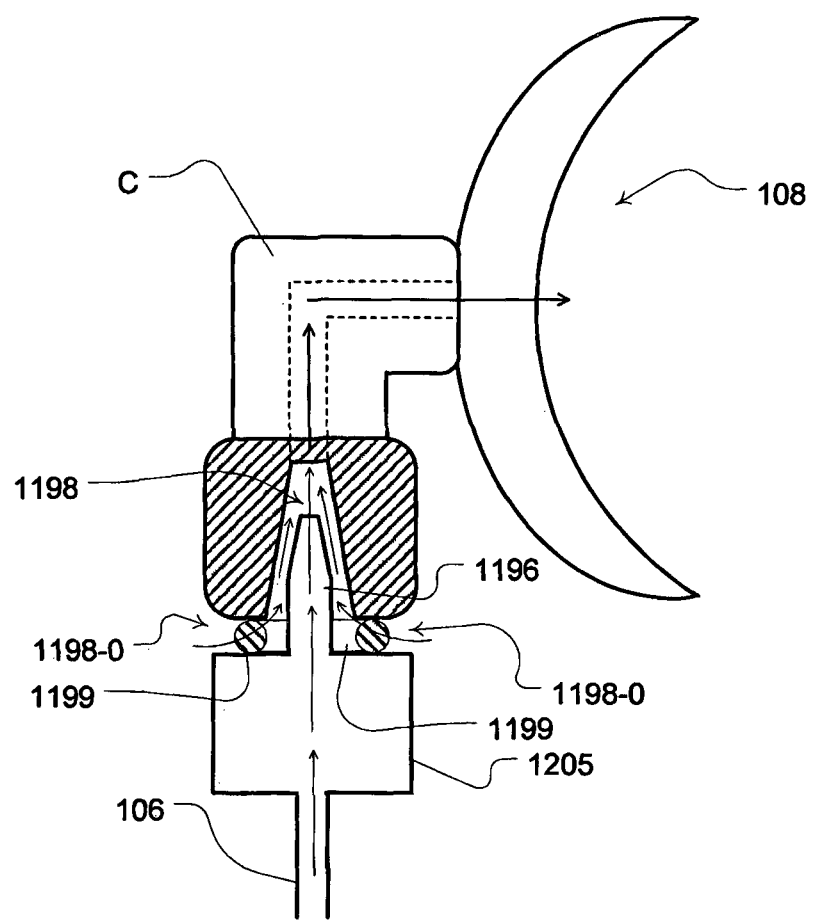
FIG. 12 is another cross-sectional illustration of an example Venturi coupler with a patient interface.

As illustrated in FIG. 12, the Venturi chamber may be coupled to an input of a patient interface 108, such as a mask. An optional swivel and/or elbow connector C may also be employed. Thus, an output of the Venturi chamber may lead to the input of a patient interface or otherwise form a part of the patient interface. In some such cases, a treatment compensator 1205, such as any one of the examples previously described, may optionally be coupled with the nozzle of the Venturi chamber such that the output of the compensator enters the nozzle. Such components may be coupled together with connector or they may otherwise be integrated as a unit.

G. Further Example Implementation of the Technology

In an example implementation of the aforementioned technology, a pressure treatment system may be configured with the following components:
1. Air compressor—The initial stage flow generator may be implemented as an air compressor. The device may thus be configured to pressurize the required amount of air per minute and supply it to the junction delivery conduit.
2. High pressure air regulator—The step up flow generator device may be configured to regulate the pressurized air entering the fine bore delivery conduit to a more accurate pressure and flow. In such a case, the step up device regulates the flow through the fine bore delivery conduit.
3. Treatment Compensator—This device then reduces the pressure exiting the fine bore delivery conduit to a therapy level of between 2-50 cm $H_2O$, which can be delivered to the patient. It may also regulate the delivery of this pressure to the patient according to the patient's breathing cycle.

Any of the functions mentioned above can be implemented in any other device as desired. Devices may be combined or split up according to any design requirement.

In the foregoing description and in the accompanying drawings, specific terminology, equations and drawing symbols are set forth to provide a thorough understanding of the present technology. In some instances, the terminology and symbols may imply specific details that are not required to practice the technology. Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology.

H. Additional Implementations

The respiratory technology described herein may be considered in reference to further system diagrams and components of the figures. As previously mentioned, a discreet delivery system (e.g., with a fine bore delivery conduit) can help to minimize respiratory therapy systems such as, for improving patient comfort. However, reducing the hydraulic diameter of a gas flow conduit can have multiple penalties. Such penalties may include any or all of the following:

(1) Impedance. This is a measure of resistance to flow. Impedance is felt both during steady state (constant flow) and transient conditions (accelerating or decelerating flow). Impedance is generally quoted in terms of static pressure loss and has (a) a fifth power relationship with hydraulic diameter for a turbulent flow (i.e. $\Delta P \propto D_H^5$). Thus, halving the hydraulic diameter results in an increase in losses on the order of 32 times.

(b) a second power relationship to velocity (i.e. $\Delta P \propto V^{(-2)}$). Thus, doubling flow velocity increases impedance by a factor of four.

(c) a linear relationship to conduit length. Thus, doubling the conduit length corresponds to a doubling of impedance.

(2) Inertance. This is a measure of resistance to the change of flow rate (resistance to acceleration or deceleration). As tube or conduit flow path size becomes smaller a greater change in pressure is required to cause the same flow acceleration or deceleration. This is largely influenced by flow area and for round conduits has a second order, relationship with hydraulic diameter (i.e., $\Delta P \propto DH^2$). Inertance is the equivalent of mass in the linear motion equation: F=ma.

(3) Power consumption. As a result of both impedance and inertance increases, higher levels of power consumption are observed. Impedance is an effect that is present regardless of flow type. Inertance increases power consumption whenever flow rate needs to change.

The architecture of the proposed high pressure systems described herein may address some or all of the above effects by changing distribution of pressure and velocity within various fluid paths of the system.

Conventional treatment pressure systems typically pressurize air to the minimum level necessary such that system pressure losses reduce this starting pressure to the desired therapy pressure by the time air reaches the patient. Such a typical flow generator measures flow and pressure internally and from these values calculates expected pressure losses and adjusts accordingly.

For example, FIG. 13A illustrates typical elements of a conventional respiratory pressure treatment system. The flow generator pressure (P1) and flow generator flow rate (Q1) of the air are shown leaving the conventional flow generator 1302. From flow generator flow rate (Q1), the system estimates mask pressure (P3) by calculating conduit pressure losses due to impedance. From here, vent flow rate (Q4) is calculated based on known vent pressure/flow relationships (often referred to as the "vent curve") and knowledge that the patient pressure (P5) is approximately that of mask pressure (P3) and vent pressure (P4) (i.e., P5≈P4≈P3). Lastly patient flow rate (Q5) is calculated by subtracting Q4 from Q3.

Losses based on individual components such as short tubes, elbows and the mask itself are accounted for by the flow generator but have not been described in detail since they do not typically change the fundamental operating principle of the system. Likewise, assessments of leak within the system are also not described.

A closed loop control system can be implemented within the flow generator to regulate blower output such that estimated pressure at the patient conforms to the active, therapy mode. It is here that factors such as inertance and impedance begin to become problematic when a fine bore conduit is implemented.

As tube sizes become smaller, the effects of inertance and impedance become increasingly significant. Thus, the control system may include parameters and components (e.g., higher pressure P1 and treatment compensator 105) for compensating for both effects, such as the system shown in FIG. 13b.

The details of how an impedance compensation can be implemented are provided further in the text. Reduction of tube size does have an exponential impact on pressure loss and hence power consumption (blower load). Beyond this, compensation for increased pressure loss basically requires the generation of higher pressures by the blower or the flow pressurizer apparatus 104. The magnitude of this increased pressure will change based on the flow rate through the fine bore conduit 106 ($\Delta P \propto V^2$). The end result is an increasing pressure range demanded of flow pressurizer apparatus 104.

Accounting for inertance requires the calculation of rates of change based on noisy pressure and flow signals. It is known that this type of calculation, even when based on good quality data, provides erratic results. Filtering and smoothing of measured data is possible but causes delays between measurement and availability of smoothed data. Combining this time delay with pressure/flow propagation delays (i.e., the time taken for a change in the fluid/gas to be felt at the opposite end of the system) can cause the system to become uncontrollable.

It some cases it might be possible, with the use of a pressure sensor at, or near, the mask, to achieve a controllable system with a tube diameter of approximately 11-12 mm while using a conventional flow generator 1302. However, below this range, control is predicted to be virtually impossible with such conventional architectures.

Furthermore, the increase of inertance places additional demand on the blower during transient conditions. Because of the increased inertance, a greater transient pressure change must be supplied by the blower to achieve the same flow acceleration. Since timeframes for flow acceleration are effectively fixed by the patient's breathing cycle, the blower must be capable of significantly increased rotational acceleration both for increasing and decreasing blower speed. Ultimately this means greater power consumption during positive acceleration and increasingly difficult braking during negative acceleration. Another consequence may be an increase in blower size and noise as larger, more powerful motors are required.

There comes a point when this transient pressure fluctuation required at the blower becomes impossible to supply. When taken far enough, just decelerating the motor may not be sufficient and the inertance problem eventually requires the blower to be able to provide negative pressures (i.e., suction). Conventional flow generator blowers are not capable of such negative pressures. Indeed the air flow across the blades of a blower will enter aerodynamic stall conditions at low impeller speeds or high back pressures. During stall, flow patterns are disrupted in the blower effectiveness diminishes rapidly.

One proposed high pressure system such as that illustrated in FIG. 13B approaches delivery of therapy pressure in a different manner and may overcome or mitigate at least some of the above discussed problems, or at least offer a useful alternative.

In the high pressure system of the present technology, the system may address both inertance and impedance effects of the small conduits described herein in two main ways:

(1) The system may alter where and how pressure regulation is achieved. For example, the proposed system may implement a treatment compensator with a flow control valve proximal to the patient to perform the function of a pressure regulation and thereby control therapy pressure delivered to the patient. This valve is fed comparatively high pressure air by a relatively high pressure flow source (e.g., flow pressurizer apparatus 104.)

(2) The proposed system may have an altered pressure distribution system compared with a conventional system. For example, higher circuit pressures upstream of the patient (i.e., in the direction of the flow generator) are employed compared with conventional positive airway pressure (PAP) systems. These higher pressures compress the air in the delivery conduit (e.g., fine bore conduit), increase its density and provide some velocity reduction and hence reduction in impedance losses. Higher system pressures necessitate and also enable the use of pressure control hardware other than conventional blowers such as pressure and flow control valves mentioned herein.

In some cases, a relief of expiratory back pressure may be necessary and can be achieved by inclusion of a blow-off/relief valve.

Accordingly, in the version illustrated in FIG. 13B, the treatment compensator 105 may be implemented with a control valve module. Generally, such a module may manage the regulation and control of a pressure step down from high to low pressure. In this example of the system, the components downstream of the compensator 105 may be conventional. Thus, such a system may be compatible with conventional positive airway pressure (PAP) patient interfaces. In some examples, mask venting may be with fixed exhaust orifice or adjustable/controllable orifice Size.

Depending on the function of the system, the mask itself may not need its own vent and consequently non-vented mask variants may be implemented.

In order to ensure that the proposed compensator functions properly, in some embodiments a pressure overhead may be enforced such that the pressure P2 received at the user end of the conduit is higher, and in some cases substantially higher, than the treatment pressure P5 (P5≈P4≈P3) required (i.e., P2>P3 or P2−P3≥K, where K is a constant representing the overhead pressure). In general, the magnitude of this relationship may depend on specifics of the compensator (e.g., valve), flow pressurizer (e.g., compressor) design and an acceptable compromise of efficiency versus conduit stiffness, system fixed and running costs. In the some cases, this pressure overhead may be suitably within a range 70-200 cm $H_2O$, and more specifically within the range 70-140 cm $H_2O$.

This can be considered a fundamentally different approach to conventional CPAP devices. With reference to FIG. 13B, the pressure from the flow pressurizer P1 is no longer the minimum pressure necessary to deliver therapy via characteristic losses. This pressure P1 is comparatively high and should be maintained such that worst case pressure losses in the conduit (based on peak flow conditions) do not bring pressure P2 at the compensator below the necessary overhead value.

I. Farther Valve Control System Examples

Figure 14:
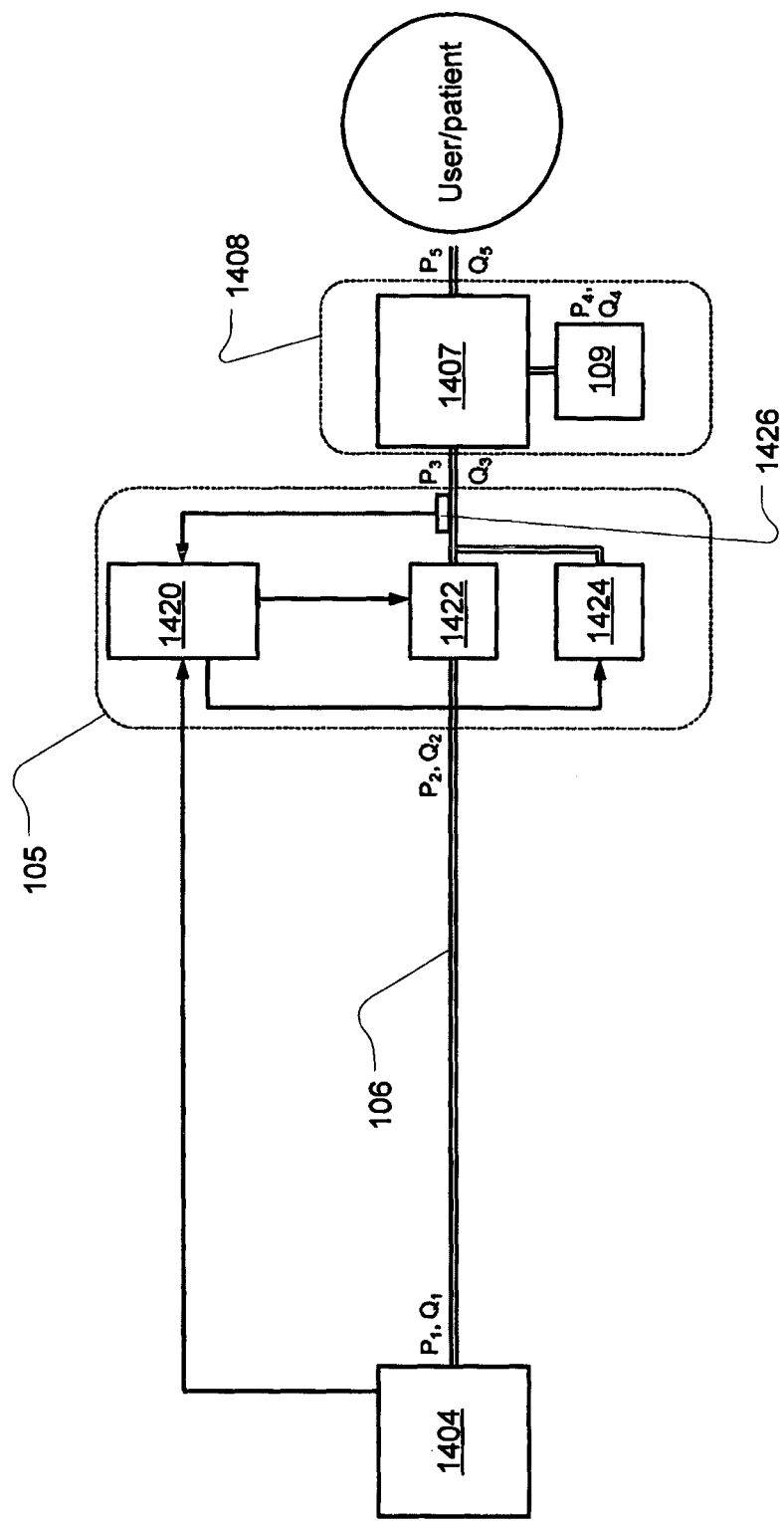
FIG. 14 is a further system configuration for some examples of the present technology.

FIG. 14 illustrates schematically an example system employing a valve-based treatment compensator 105 suitable for implementation with the present technology. The system may be configured to supply air to the respiratory system of a patient at levels suitable for respiratory therapy (e.g., typically 2-40 cm $H_2O$) via fine bore conduit 106 or other small fluid conduit (such as a tube). Complex therapies are possible (e.g., not simply a constant pressure, but rather varying pressures) as the desired pressure at the patient can be altered via a controller command in real time. Via configuration changes options for vented and non-vented masks may be implemented, each aimed at satisfying a different type of patient comfort. In FIG. 14, the system includes a flow pressurizer apparatus 1404, treatment compensator 105 and patient interface system 1408, which are further explained in detail below.

I.1. Flow Pressurizer Apparatus

Figure 16:
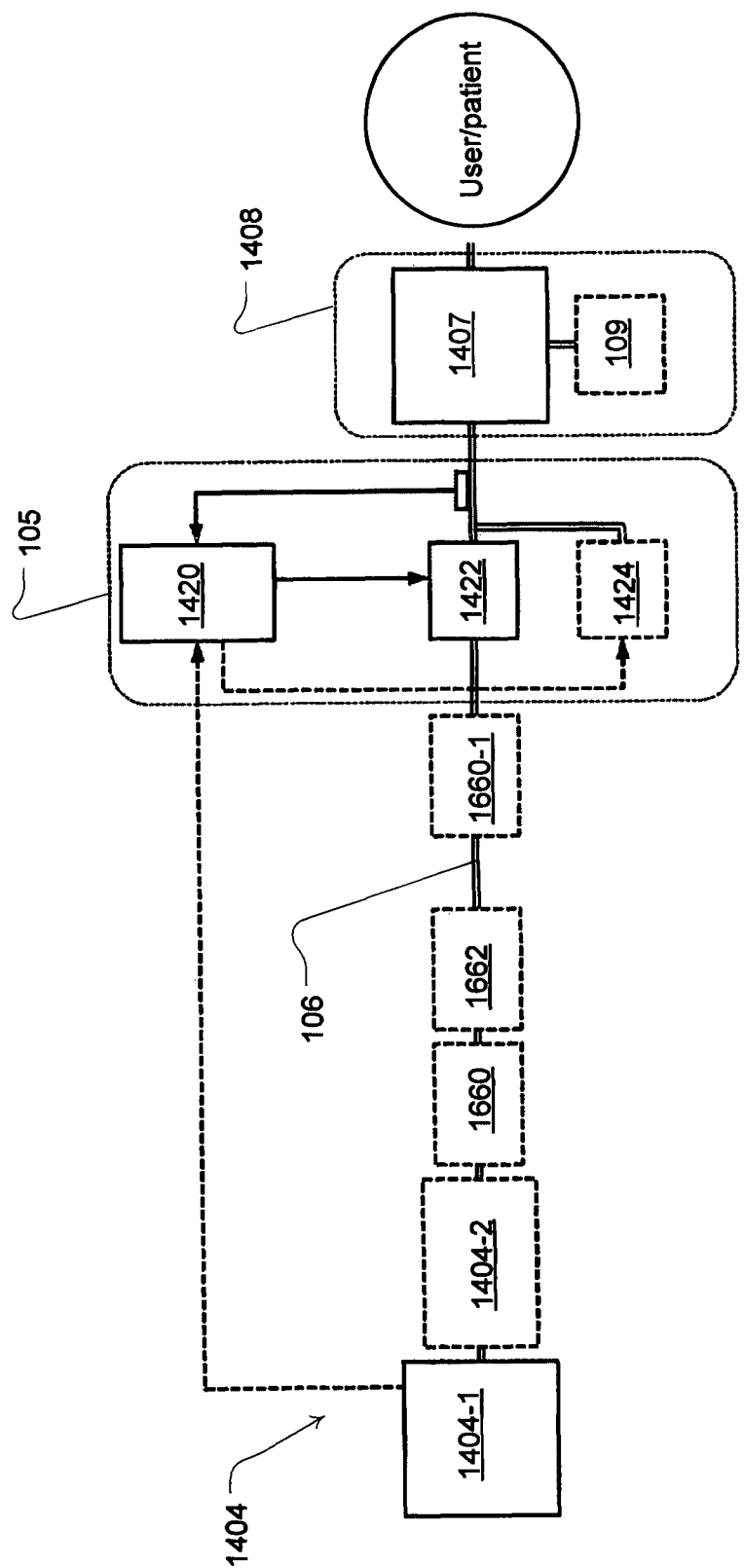
FIG. 16 is another diagram of an example system configuration for some examples of the present technology.

The flow pressurizer apparatus 1404 may include a primary pressure/flow generator (1404 in FIG. 14 or 1404-1 in FIG. 16). The primary pressure/flow generator creates an increased pressure that can be delivered either directly to the valve based treatment compensator via an air delivery conduit (as illustrated in FIG. 14) or to a supplemental pressure/flow generator 1404-2 (as illustrated in FIG. 16).

The primary pressure/flow generator can include various technologies. One common version includes an electromechanical rotary air pump. Additional versions may include piston type pumps, thermal pumps, and/or chemical pressure generators.

In some cases, the flow pressurizer apparatus 1404 may be a pressurizer implemented with one or more stages based flow generator. A two stage version may employ two ventilator blowers connected in series. The latter, case may be implemented with conventional blowers that are each capable of generating output pressure of approximately 100 cm $H_2O$ at up to 100 L/min volumetric flow rate. The blower implemented in ResMed's Elisee 350 may be a suitable device.

Figure 15:
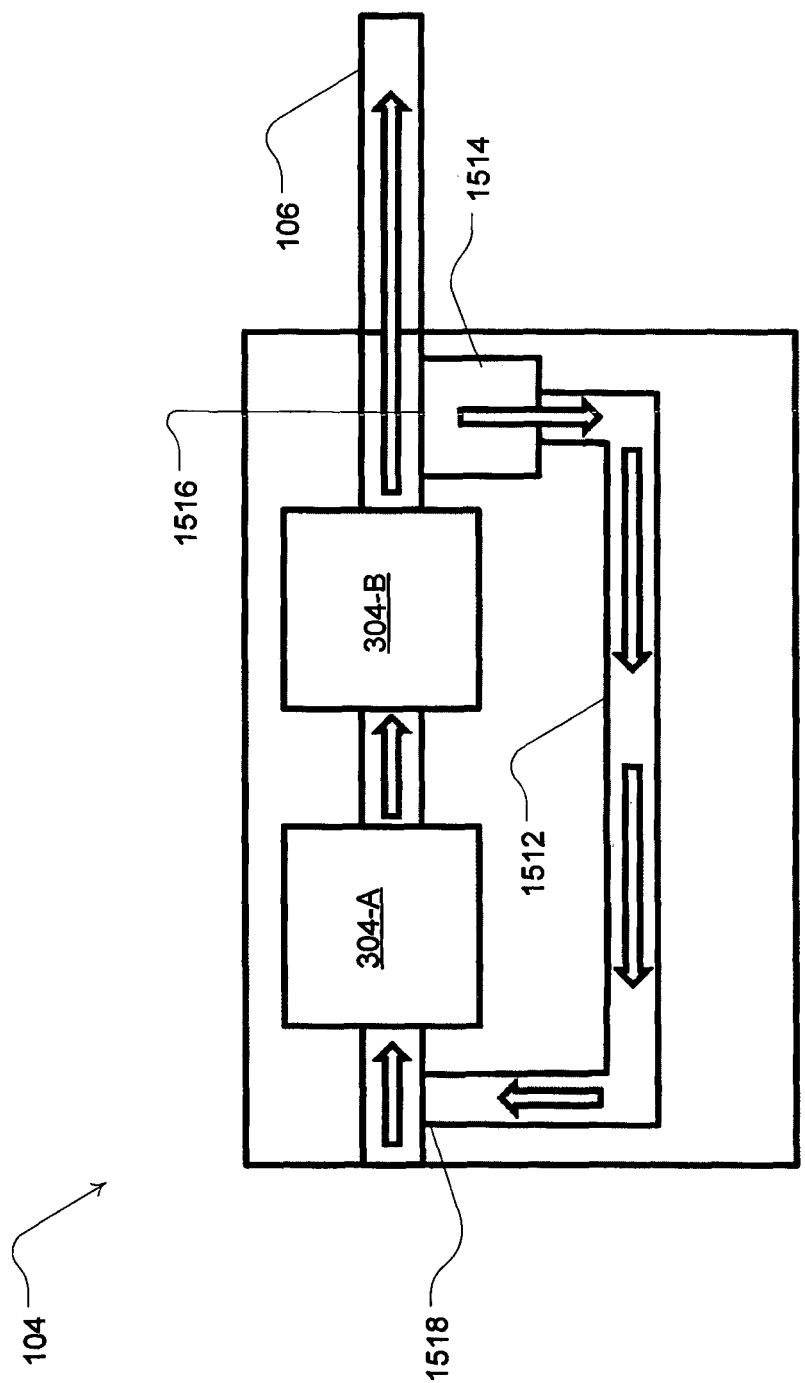
FIG. 15 is a schematic diagram of example components of a flow pressurizer apparatus suitable for use with some examples of the present technology.

As illustrated in the example of FIG. 15, a two stage system with flow generators 304-A, 304-B may optionally include internal bypass ducting 1512 and flow diverter/damper component 1514. These may assist for conditions of low to zero flow in the air delivery conduit of fine bore conduit 106. When the bypass flow diverter/damper component 1514 is set to be open, a path is created connecting the outlet 1516 of the second stage blower (e.g., flow generator 304-B) pneumatically with the inlet 1518 of the first stage blower (e.g., flow generator 304-A). Such a bypass arrangement allows the blower stages to avoid aerodynamic stall during periods where downstream air is not required. In simple terms, when activated, the bypass duct allows air to move through the blower stages despite there being little or no air demand via the air delivery conduit. This allows the blowers of the flow generators 304-A, 304-B to run at speeds and flows suited to their design throughout the breathing cycle, regardless of patient and mask flow requirements. With this optional feature, during low-to-zero flow conditions, the blowers can avoid forcing the supply flow into a dead-ended conduit.

In an alternative configuration, where the patient interface (e.g., mask) does not have a conventional vent it is possible to reduce these performance parameters. For example, by implementing an active vent (e.g., a vent with a controlled variable exhaust area) that can open and close on demand, the flow rate demands on the system by be lowered by reducing or eliminating waste vent flow throughout the patient breathing cycle. However, due to the pressure requirements of the proposed treatment compensator, a multi stage blower may be desirable. Nevertheless, power consumption can be reduced.

A connection of blowers in series can have an additive effect on pressure. This can enable the high system pressure as described herein to be generated in stages. For example, the total pressure output of the stages may be in a desired range of 140-200 cm $H_2O$ at up to 100 L/min flow rate.

In some cases, a single stage or more than two stages may be implemented. Such versions may be implemented with, for example, traditional ventilation blowers, positive displacement (piston or roots) compressors and screw or turbine compressors.

Optionally, although not shown in FIG. 15, one or both of the flow pressurizer apparatus (the flow generators 304-A and/or 304-B) may include either integrally or remotely, a controller configured for controlling or setting required patient therapy pressures by adjusting operation of the flow generators 304-A and/or 304-B. This may be performed in real time such that changes may be made throughout a patient's breathing cycle. Optionally, such a remote control may be implemented by a controller of the treatment compensator. In other cases, such control of the flow generators may be made unnecessary by an implementation of suitable control of the treatment compensator. For example, the treatment compensator may include a controller or other processing components configured for setting real time pressure profiles without reliance on control over the pressure generated by the flow pressurizer apparatus 1404.

In some cases, a real time pressure signal such as one representing a required pressure for the patient's airway may be communicated, such as via a data communication signal bus, from the pressurizer apparatus to treatment compensator 105 (e.g., a valve control system). Such communication between these components may be bi-directional and may include additional information. For example, such signaling may permit communication of various data including, but not limited to, measured flow rates, measured air pressure at the exit of the flow pressurizer apparatus 1404, measured pressure at the low pressure side or stepped down side of the treatment compensator, respiration rate, respiration phase (inhalation or exhalation) and a release valve state (e.g., percentage open or closed).

As previously mentioned, in some cases, the flow pressurizer apparatus 1404 may be implemented as a multi-stage pressure source system. For example, dual pressure sources may be provided and they may be provided in separate housings in contrast to the implementation of FIG. 15 which has a common housing. In the example of FIG. 16, a primary flow generator 1404-1, which may be hidden out of the way (e.g., under the bed) can primarily generate needed flow and most of the necessary pressure. It may be connected via a relatively large, low resistance conduit (as opposed to a fine bore conduit) to a supplemental pressure/flow generator 1404-2. The supplemental generator may be controlled to provide pressure boosting during peak flow conditions in order to keep system functionality stable. The supplemental generator would normally be employed to supply the additional pressure necessary to overcome delivery conduit losses. An advantage of this inclusion can be to move the primary noise source (associated with the operation of the primary generator) away from the patient.

In some alternatives, such pressure sources may be implemented with other devices. For example, they may be implemented with positive displacement compressors. As such, the air may be supplied to the entry of a delivery conduit via pistons, oscillating diaphragms and/or roots blowers. In some configurations the pressure of such air supply may be high (e.g., fractions to multiples of atmospheric pressure) and thus considerably higher than the pressure and flow sources of other examples described herein such as FIG. 14. In such situations, the system may be configured to include a primary air reservoir 1660. In further embodiments the system may include a secondary air reservoir 1660-1. When present, the function of reservoirs 1660 and 1660-1 is similar to a pressure tank of a conventional compressor system. The main purpose is to enable the use of a flow/pressure generator system that is capable of meeting average, but not peak, demand with the reservoir capacity being utilized during peak flow and charged during low flow. The system can also utilize a pressure regulator 1662 to limit the pressure entering the air delivery conduit. In yet further configurations it may be possible to tune the operation of these compressors to deliver air of sufficient pressure and volume to match the example of FIG. 14, thus negating the need for reservoirs and additional pressure regulators.

In yet further alternatives, the air delivery conduit may be connected to a compressed air supply often found in hospital rooms. This would eliminate the need for a dedicated flow and pressure source as described in the examples describe herein (e.g., FIG. 14) but may then require a therapy controller be integrated in a treatment compensator such as in the valve controller 1420. In some further cases, the real-time pressure profile of such a system may be dictated by additional external hardware.

I.2. Delivery Conduit

A delivery conduit, such as fine bore conduit 106, may serve as a main pneumatic connection between the flow pressurizer apparatus and the treatment compensator (and additionally the patient). The conduit's length may optionally be in the range of 70-200 cm. In some cases, the conduit may have an inner diameter of 7-8 mm and a wall section of approximately 1-1.5 mm, giving an overall outside diameter of approximately 9-11 mm. In such cases, when such small diameter conduits are used (as mentioned elsewhere in the specification, the system is designed to accommodate even smaller diameters), flow pressurizer apparatus will be configured to supply the higher pressures corresponding to the increased static pressure loses associated with flows through the smaller conduits.

The conduit may be substantially flexible and it may be crush resistant similar to the material characteristics of conventional therapy air conduit. Although different tube types may be implemented, in some cases, a helical tubing or wire reinforced tubing may be employed. Such conduit is comparable to endotracheal tubes. One example of the latter may include a length-extended version of the Mallinckrodt™ Oral/Nasal Tracheal Tube (Model 86470).

I.3. Valve Type Treatment Compensator

In some cases of the valve type treatment compensator 105 such as in the system of FIG. 14, it may be implemented with a valve controller 1420, a pressure reduction valve 1422, a relief valve 1424 and a pressure sensor 1426. The pressure reduction valve may be a typical flow control valve. The pressure input requirements of the valve may appropriately be in the range of 70-140 cm $H_2O$ depending on the output of the flow pressurizer apparatus. The valve controller 1420 is implemented to operate (e.g., control the settings for) the valve regulator to control pressure delivered to the patient. Thus, a pressure sensor 1426 may provide a pressure measure to the valve controller to enable it to serve as a closed loop pressure controller. For example, the valve controller 1420 may include a Proportional, Integral, Derivative controller (PID). Such a controller may be implemented as an integrated central controller for control of operations of the respiratory apparatus as described herein or may be an additional controller for the particular control operations of the compensator. In either case, the controller may optionally be implemented with a processor or other control circuitry component(s).

The optional relief valve 1424 may also be controlled by the valve controller 1420. This relief valve may be a proportional waste valve such as that as described in the international patent application WO2013/040198, which is incorporated herein by reference. The relief valve tends to mitigate the cyclic pressure swings during the exhalation phase of breathing, caused by the characteristic flow and pressure relationship of conventional mask vents. Thus, the relief valve can be implemented for improving patient comfort. In some examples, the relief valve may be omitted.

While the valve 1422 may be a flow control valve that regulates pressure, other valve types may also be implemented. For example, pinch valves and shuttle valves as previously described may be implemented and/or other pressure regulators. In each case, the control principle (e.g., a pressure step down) may be similar but the actuation mechanics of the operation may be different. In either case, a high impedance path is constructed through which high pressure air may flow from the pressure source. At the exit of the valve, pressure is controlled to step down by controllably setting the impedance of the valve to ensure the stepped down pressure remains within a target pressure window (e.g., a desired pressure for inhalation and/or exhalation and may optionally include a pressure treatment portion to prevent upper airway obstruction). This window may change depending on the controller's settings which, on the other hand, are dependent on the treatment pressure that needs to be provided to the patient.

In some cases, a hybrid valve may be implemented that includes an air entrainment component as a means to reduce overall mass flow demand on the compressor or other pressure source. In such an implementation, high pressure air is fed through a venturi-style nozzle which then draws ambient air into the flow stream. Pressure is thereby traded for flow multiplication. A nice advantage of this system is that in the event of failure of the pressure/flow source, the air path is effectively open, mitigating against any possible safety risks associated with asphyxiation. Thus, such an entrainment hybrid valve component may also serve as an anti-asphyxiation valve.

Figure 17:
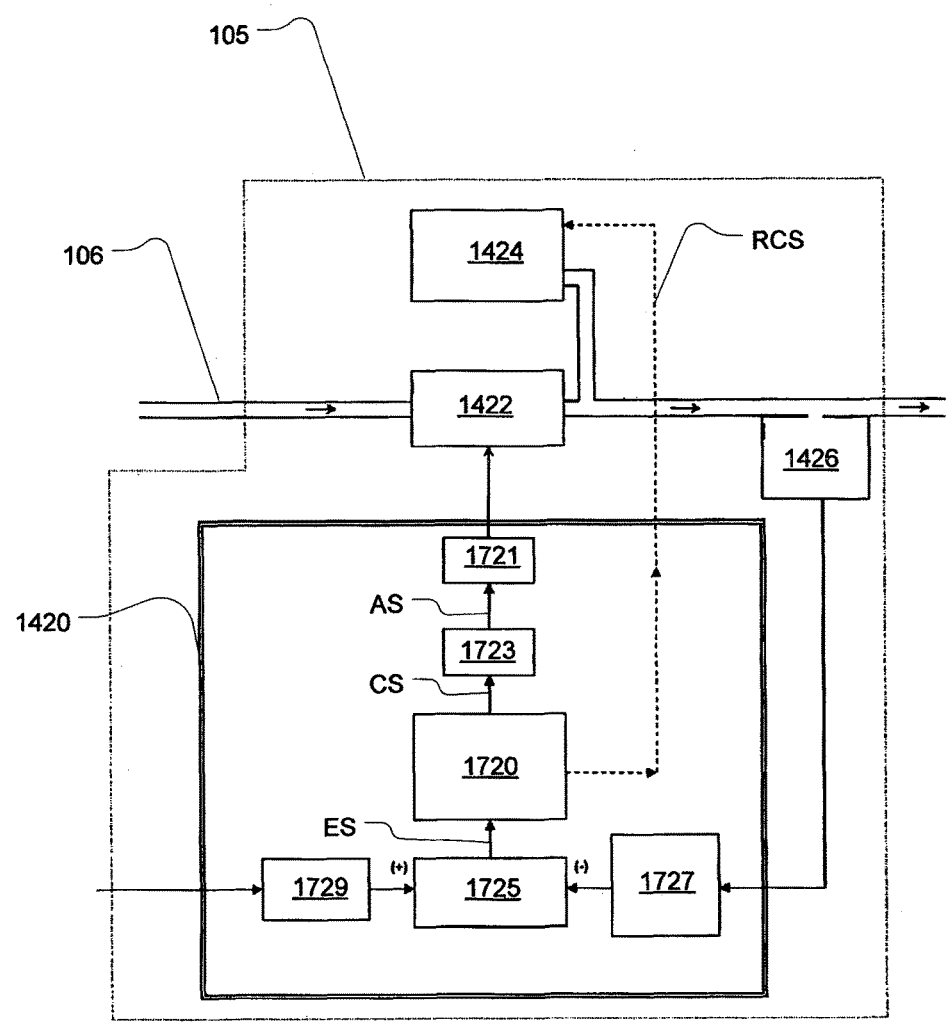
FIG. 17 is an example valve control system for implementation with versions of the present technology.

A detailed example of a valve-type treatment compensator may be further considered with reference to FIG. 17. In this example, the valve controller 1420 includes a discrete processor (e.g., processing unit 1720). The processor may be configured (e.g., programmed) with a control algorithm (e.g., a PID algorithm) to set the valve 1422 such as by controlling valve actuator 1721 via driver 1723 with a control signal from the processing unit 1720 to the driver and an actuator signal from the driver to the actuator. The processing unit may generate the control signal based on an error signal received from an error evaluation unit 1725 (e.g., comparator circuit). The error evaluation unit 1725 compares a processed pressure signal from a pressure signal processing unit 1727 with a pressure set point signal from an input signal buffer 1729. The pressure set point of the buffer may in some cases be set or provided by a processor or controller of the flow pressurizer apparatus 1404 via an input signal to the buffer. In some cases, the pressure signal processing unit 1727 may optionally include an anti-aliasing filter, a pre-amplifier and/or an analog-to-digital converter.

I.3.1 Valve Controller

The valve controller may have various configurations and may be implemented as illustrated in the example of FIG. 17. In some cases, as previously mentioned, it may include a valve actuator 1721, driver 1723, processing unit 1720, error evaluation unit 1725, set point input signal buffer 1729 and pressure signal processing unit 1727.

1) Valve Actuator

This may be an electro-mechanical transducer that converts an electrical signal such as an actuator signal (labeled "AS" in FIG. 17) into the mechanical change in the setting of the valve (e.g., opening aperture).

Valve actuators can be of the following types:

i) Linear Solenoid:

A linear solenoid may be implemented. Examples may include the Moog Medical standard linear series, Ledex Tubular series or Kuhnke miniature range etc. Typically, the range of force may be between 2 to 200 Newtons, with stroke of up to 10 mm depending on the configuration, level of friction and valve resistance encountered. An example may be the Ledex STA Push Tubular Solenoid (Part number: 195223, 13 mm dia.×27 mm) which may exert 4.5 N at 1 mm travel and traverse 5 mm in 13 ms. Preferably, the required stroke is less than 0.5 mm, and even more preferably the stroke is about 0.2 mm.

ii) Rotary Solenoid:

A rotary solenoid may be implemented. Such a component may provide valve actuation either through means of an actuation linkage or through a dedicated valve design such as an expanding iris aperture type. An example of the linkage could be to use a pushrod to depress the valve if that were desirable or rotation of a cam or roller on a contact plate to achieve the adjustment. One advantage of such an implementation would be that a greater force could be exerted through mechanical advantage when compared to linear solenoid for a given input power. A rotary solenoid with an angular stroke of between 25 to 110 degrees could be used depending on the valve design.

iii) Linear Piezoelectric:

Linear Piezoelectric motor(s) may be implemented in some version. An example may be the 6 N Piezo LEGS Linear Motor from Micro Motion Solutions. This may be adapted to control the valve. It may have the advantage of high step resolution and stalling force, without mechanical play or backlash. Rotary adaptions of piezoelectric motors could also be implemented as described above.

iv) Servomotor:

Additionally, a servomotor may be implemented and may provide a precise control of angular, position that in turn could be used to control the valve. Similarly, such a servo motor would demand adequate torque and angular speed response for actuating the valve.

v) Stepper Motor:

In some cases, a stepper motor could be included in a manner comparable to other angular control devices described above. This may be particularly suitable when the valve design dictates less resolution and feedback on position.

2) Output Driver.

The driver 1723 serves as the power block that produces the necessary output interface to the valve actuator 1721. It can be implemented using discrete elements (power MOS-FETs) or Integrated Circuits, for example.

3) Processing Unit.

This is the block that calculates or generates the control signal CS. Typically, such a signal will compensate for a detected deviation between a set point for the pressure (e.g., target pressure) and actually measured therapy pressure such as from a pressure sensor. Such a processing unit may be analogue and/or digital. An analog version typically uses analog electronics such as with, for example, Operational Amplifiers (OpAmps), to implement a control algorithm. A digital version may include one or more CPU/MPU devices or programmable logic, and the embedded software (firmware) that runs the control procedures (e.g., PID algorithm) to do the control signal calculations.

Another potential function of the processing unit can be to monitor the actual therapy pressure and produce the control signal RCS for the relief valve 1424 if/when the therapy pressure reaches or exceeds critical value(s).

4) Setpoint Signal Buffer.

This buffer (1729) can be used to accommodate and shape up the (optional) signal from the flow pressurizer apparatus that may determine and sets a therapy pressure set point (target pressure).

5) Error Evaluation Unit.

This unit (1725) may be implemented to calculate an "error" and produce an error signal ES. The error may represent a deviation in actual therapy pressure (measured) from the required (setpoint target). The unit may take the therapy pressure setpoint signal and a measured therapy pressure signal and process the values. For example, the values can be subtracted and the difference can be compared with zero. Alternatively, the values can be divided and the ratio can be compared to one.

The error unit can be of analog and/or digital types depending on the type of the processing unit 1720 above.

6) Anti-Aliasing Filter, Pre-Amplifier and A/D Converter Block.

A pressure signal processor may serve as a unit for conversion of the signal coming from a pressure sensor 1426 into a signal of a form suitable for operation of the error evaluation unit 1725. For example, it may be formed by one or more of an anti-aliasing filter, pre-amplifier and/or analog-to-digital (A/D) converter. In such cases, the A/D converter may typically be implemented when a digital type of valve control is implemented.

I.3.2 Pressure Reduction Valve

As previously mentioned, the treatment compensator may include a valve 1422 for pressure reduction.

I.3.2.1 Background and Theory

A conventional CPAP system supplies a therapy pressure and also adapts to patient breathing by reducing flow during exhalation and increasing flow during inhalation. This is because both the patient and the flow generator push air out of the mask vent during exhalation. However, during inhalation, the flow generator continues to blow air out of the mask vent but also has to supply air to the patient. If the vent in a mask is passive (i.e., just an opening), one particular rate of flow through the vent will result in only one pressure in the mask. This relationship between pressure and flow may be considered to form the "pressure flow curve" or simply the "vent curve" of a vent.

If the flow generator is programmed with the vent's pressure flow curve, it can correctly reduce flow during exhalation and increase flow during inhalation while keeping therapy pressure constant.

Figure 18:
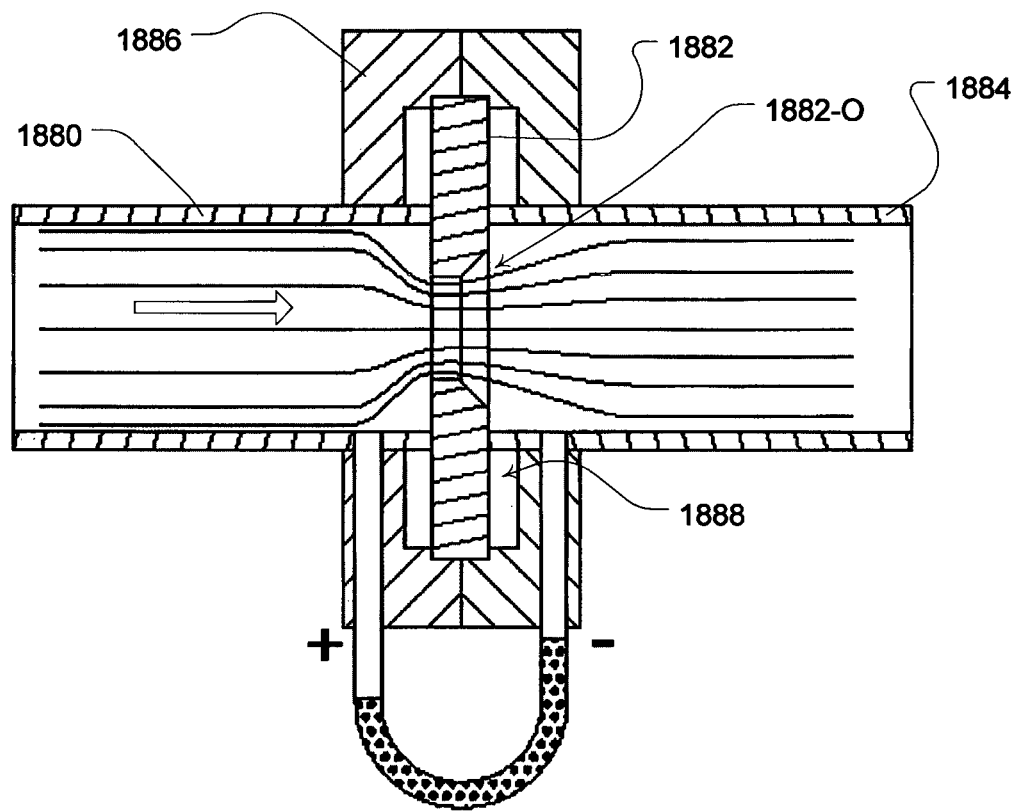
FIG. 18 is an illustration of an example orifice plate that may be configured as a treatment compensator in some examples of the present technology.
Figure 19:
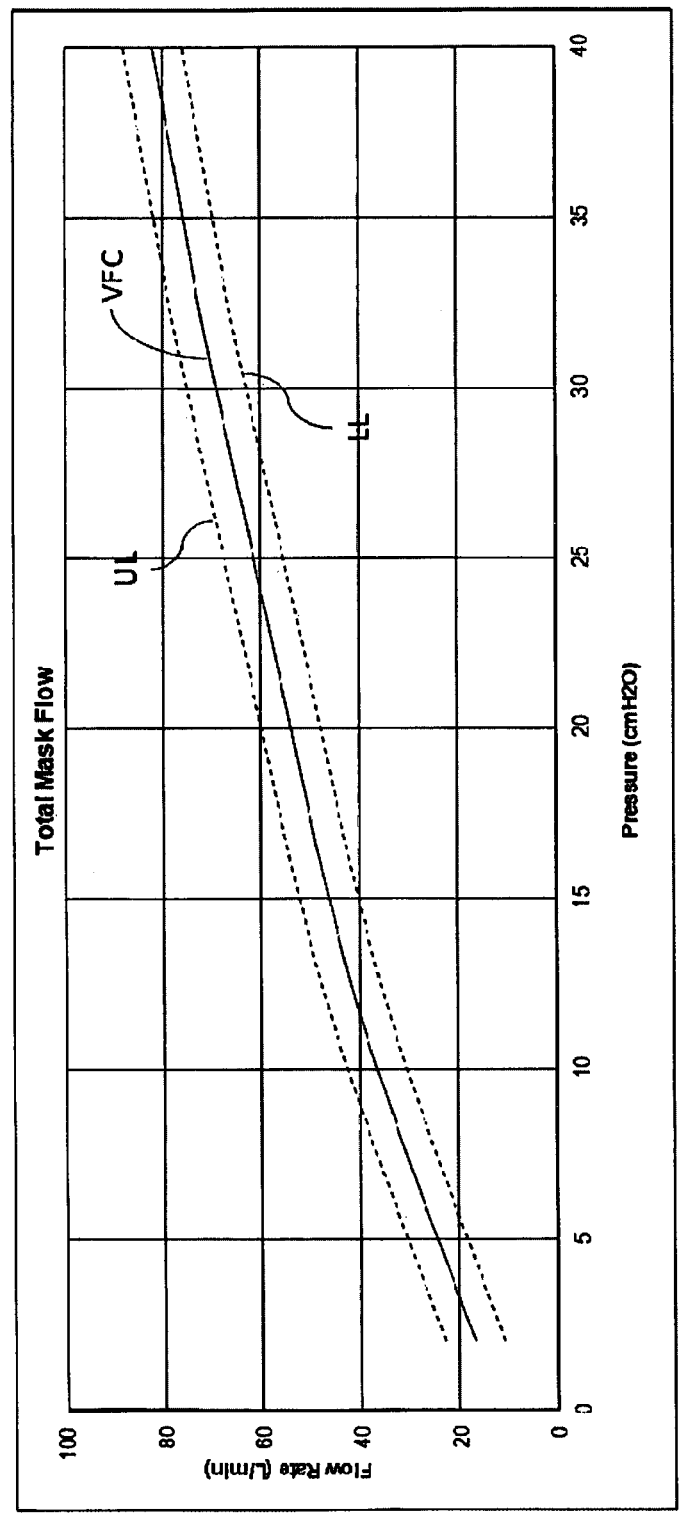
FIG. 19 is a graph illustrating an example mask vent flow pressure curve.

In the case of the proposed system, the pressure delivered to the mask by the flow pressurizer apparatus is too high to supply to the patient and should be reduced. One known way of reducing the pressure is by implementation of an orifice plate, such as the version illustrated in FIG. 18. The high pressure air is supplied at the inlet 1880, passes through an orifice 1882-0 of the orifice plate 1882 and out the outlet 1884. In this case, an optional carrier ring 1886 may serve as a housing to couple the inlet to the outlet with the orifice plate located therebetween and within an annular slot 1888. The high pressure is reduced by the impedance of the orifice.

In addition to simply reducing pressure, the orifice plate type-valve may also adapt flow to maintain pressure at the patient during both inhalation and exhalation. For example, by reducing the area of the orifice during exhalation and increasing it during inhalation, the valve can adapt to match the vent pressure flow curve.

A closed loop feedback system may be implemented in the cases where a change in the size of the orifice may be actuated so as to maintain the therapy pressure (and flow) at both inhalation and exhalation. A difficulty lies in using the lower energy, lower pressure side of the treatment compensator (See P3, Q3 in FIG. 14) to drive a valve at the higher energy, higher pressure side of the treatment compensator (See P2, Q2 in FIG. 14). This can be overcome via mechanical advantage, or leverage. For example, a large diaphragm at the P3 side can act as a force multiplier to operate a valve at the P2 side.

Figure 20:
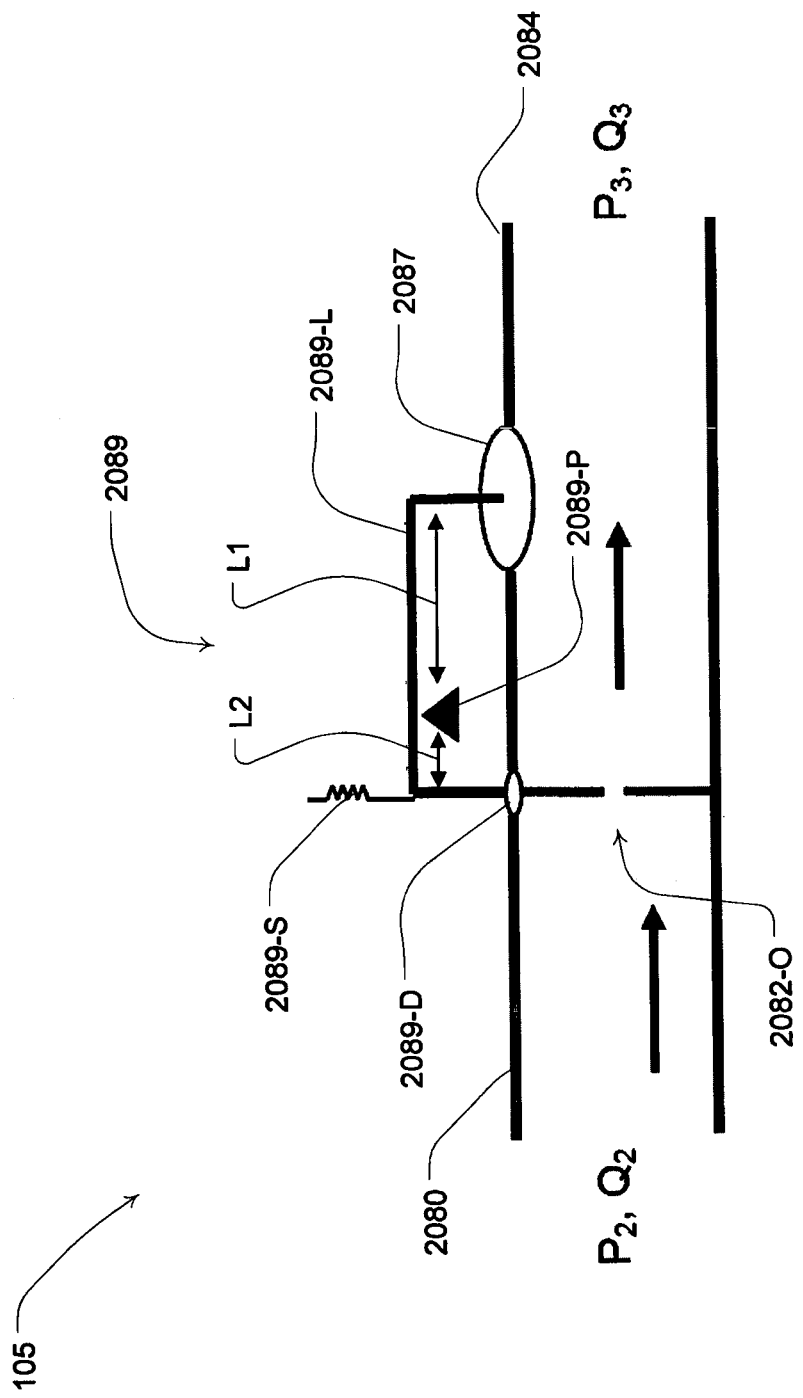
FIG. 20 is a diagrammatic illustration of an pneumatic-mechanical treatment compensator.

This principle may be considered in reference to the example illustrated in FIG. 20. In this example, the treatment compensator 105 employs a variable orifice 2082-0 between the inlet 2080 with an orifice actuator 2089 that is activated by an outlet diaphragm 2087 so as to selectively increase or decrease the orifice size. The actuator may include a lever 2089-L that couples the outlet diaphragm and orifice plate. This coupling may optionally include an inlet diaphragm 2089-D. The actuator may also include a pivot 2089-P that may be adjustable so as to selectively change the balance of the lever. An optional spring element 2089-S may also be included. For example, expansion (such as due to decreased outlet pressure) and contraction (such as due to increase outlet pressure) of the outlet diaphragm 2087 may activate the lever so as to move the orifice plate to increase or decrease the orifice size respectively.

I.3.2.3 Additional Valve Examples

Other devices for reducing pressure also involve passing air through small openings. However, the opening may be a small tube or tortuous path such as in the following additional examples as previously discussed.

(1) a pinch valve—a compliant tube whose lumen can be reduced to maintain therapy pressure close to a fixed value. This valve can be compared to fingers pinching shut a compliant tube to reduce its hydraulic diameter and, subsequently, to reduce the flow.

(2) a shuttle valve—a rigid moving part that closes off conduits within a housing in order to maintain therapy pressure close to a fixed value.

Air Entrainment System

The energy released during the expansion of the gas is, in some cases, not recovered such as when only an orifice is used. However, in some such cases, a Venturi component, such as a Venturi tube or chamber that can adapt the patient flow to recover some of the energy lost during expansion by entraining surrounding air to increase flow to the patient such as in the example previously described. This would enable only a portion of patient flow to be supplied at high pressure. The remainder of patient flow would be entrained at the valve close to the patient, thus increasing efficiency.

Thus, the pressure reduction valve may be implemented with an orifice plate, pinch valve, shuttle valve, venturi tube that recovers energy from gas expansion, etc.

I.3.2.4 Further Proportional Solenoid Valve Example

In the example of FIGS. 21-26 an example proportional solenoid valve 1422 is shown which may serve as a part of the treatment compensator 105 described herein.

I.3.2.4.1 Components

FIG. 21 is a cross sectional view of example parts for the valve 1422. A sectioned, exploded view of the example flow valve assembly implemented for pressure control is shown in FIG. 22. The valve may be implemented to maintain closed loop control over the therapy pressure delivered to the patient.

This version of the valve is an electromechanical device. The active element is a proportional solenoid that is under closed loop control (e.g., PID) based on the valve outlet pressure. While a proportional solenoid has been used in this design other types of linear actuators such as Piezo stacks could be implemented. As previously described, to be suitable for this application, an actuator should have a fast response and short stroke.

The device can regulate high incoming pressure, such as pressures in a range from above the therapy levels of respiratory treatment described herein up to about 2 psi (140 cm H₂O) (e.g., in a high range of about 70-140 cm H₂O) so as to convert them down to suitable patient breathable pressures (e.g., therapy pressures).

As shown in FIGS. 21 and 22; the valve assembly 1422 includes a lower body 2202 and seat plate 2203. The lower body includes low (step down) pressure exit ports 2202-X1, 2202-X2 and a high pressure entry port 2202-E1: The lower body also includes a first pilot tube connection port 2202-P. A platen assembly is formed by platen 2205, diaphragm 2206, platen top 2207, capillary tube 2208 and platen seat 2209. The valve also includes an upper body 2211. The upper body has a second pilot tube connection port 2211-P. A solenoid assembly is formed by solenoid coil 2213, solenoid collar 2214, solenoid return spring 2216, interior chamber valve seat 2217 and retaining collar 2218. The valve assembly also includes a capillary exit port 2219, base plate 2220 and pilot flow tube 2221.

I.3.2.4.2 Operation

Operation of the valve may be considered with further reference to FIGS. 23A and 23B which respectively illustrate closed and opened valve positions. The valve may be considered to form a main body comprised by the upper body 2211 and the lower body 2202. These may be fastened together, for example, with bolts, pins etc. (not shown). These upper and lower bodies sandwich a diaphragm 2206 such that the diaphragm separates the low pressure outlet chamber 2202-LC and an interior chamber 2211-IC. The platen assembly includes platen 2205, diaphragm 2206, plate top 2207, capillary tube 2208 and platen seat 2209. The platen assembly moves axially in the valve assembly to blank off or to open the orifices 2203-O of the air paths formed through the valve seat plate 2203 (see FIGS. 24A and 24B). The air paths (or air channels) through the orifices 2203-O are designed to connect the high pressure inlet chamber 2202-HC to the low pressure outlet chamber 2202-LC and the opening or closing of the orifices 2203-O by movement of the adjacent surface of the platen seat 2209 facilitates or prevents such a communication. The platen assembly includes an axial hole in which a capillary tube 2208 is affixed, providing a sealed fluid connection between the interior chamber and a low pressure sink 2220-S (exhaust), for the purpose of controlling the interior chamber pressure. This is used to control the movement of the diaphragm and the platen seat. The controllable opening or closing of the orifices facilitated by the movement of the platen seat that serves as part of an actuator seal, changes the air flow to the low pressure chamber and, therefore, the pressure in the low pressure chamber. Thus, in the proposed system the orifices are used for forward pressure control—this is to say that they are used to adjust the flow/pressure associated with the low pressure chamber.

The air paths in the valve seat plate 2203 are the primary path from the high pressure to the low pressure side of the valve via the orifices 2203-O. The seat plate 2203 can be a hollowed out cylindrical cap with an array of round holes (e.g., 24) that provide a path of air from the high pressure side to the low pressure output as illustrated in FIG. 24A. A pattern of holes of the seat plate is illustrated in FIG. 24B. The plurality of holes may be in a ring pattern as illustrated such that they may correspond to a ring surface of the platen seat 2209. Optional channels 2203-CH (as best seen in the seat plate examples of FIGS. 30 and 31) may be cut into the low pressure side LPS of the seat plate 2203 to provide a low resistance path for the air to reach one or more low pressure outlets, after passing through the orifices of the seat.

A central protrusion 2203-CP may be provided on the high pressure side HPS through which there is a bored through-hole 2203-TH. Within this bore slides the capillary tube 2208 under the action of the platen assembly. This tube and hole provide a fluid path from the interior chamber 2211-IC to a low pressure sink 2220-S (exhaust) via a sleeve of the capillary exit port 2219 and base plate 2220.

The interior chamber 2211-IC pressure is controlled through the use of the capillary tube as an air, and hence pressure, leak path. This forms part of the main control mechanism of the valve. Within the interior chamber 2211-IC the capillary tube 2208 is covered and uncovered in a controlled manner, via the action of the proportional solenoid assembly (solenoid coil 2013, solenoid collar 2014, solenoid return spring 2016, retaining collar 2018), depending on the desired operating conditions of the valve. The proportional solenoid can have a very small stroke in the order of about 0.007 inches (20 μm).

In the closed state, as shown in FIGS. 23A, 25, 25A, 25B and 25C, the valve prevents air from flowing from the high pressure inlet chamber 2202-HC to the low pressure exits 2202-X1, 2202-X2. While two such diametrically opposed outlet ports or exits are shown, in some versions a single outlet or low pressure exit will suffice.

In this closed state the solenoid is set to a position such that the interior chamber valve seat 2217 presses against the interior chamber opening of the capillary tube 2208 or is in very close proximity to it. This ensures minimal or zero relief flow escaping via the capillary tube 2208 to a low pressure sink 2220-S. The interior chamber 2211-IC is now, for functional purposes, a dead ended volume.

Under these conditions, positive pilot flow from the high pressure inlet chamber 2202-HC pressurizes the interior chamber 2211-IC (entering the pilot tube connection port 2211-P) via a high impedance fluid conduit or pilot flow tube 2221 that connects the lower body 2202 to the upper body 2211. Pressure in the interior chamber 2211-IC presses down on the relatively large area of the upper surfaces of the diaphragm 2206 and platen assembly. Opposing this are the combined lifting forces of air in the high pressure inlet chamber 2202-HC and low pressure outlet chamber 2202-LC. High pressure air from high pressure inlet chamber 2202-HC is applied to the underside of the platen seat 2209 via the comparatively small area of the orifice 2203-O flow paths. Low pressure air in low pressure outlet chamber 2202-LC acts on the remaining underside area of the diaphragm and platen assembly.

As interior chamber 2211-IC pressure rises, the resultant downwards force counteracts and overpowers the lifting forces from underneath. With a greater force from above than below, the diaphragm and platen assembly is forced down so that the platen seat 2209, which may be a rubber or other seal type material, reduces a flow gap between the ring shaped surface of the platen seat 2209 and a surface of the seat plate 2203 and may then come into contact with a surface of the seat plate 2203, thereby sealing against it (e.g., sealing each of a ring pattern of holes (e.g., each orifice 2203-O)).

When this occurs, the seat plate exit holes/orifices are sealed and air is prevented from flowing from the high pressure inlet chamber 2202-HG to the low pressure exit(s) 2202-X1, 2202-X2 as seen in FIG. 25.

Until the interior chamber valve seat 2217 is lifted by energizing the solenoid coil 2213, the interior chamber 2211-IC remains at high pressure and will keep the platen assembly pressed against and sealing against the seat plate 2203, ensuring the valve remains closed.

For the valve to be able to open, the platen assembly must be able to rise and thereby break the seal between the platen seat 2209 and the seat plate 2203 at the orifices 2203-O. Such an open state or configuration may be considered with reference to FIGS. 23B, 26, 26A, 26B and 26C.

When the valve is in its closed state, the interior chamber 2211-IC is under the influence of high pressure which in turn forces the platen assembly downwards onto the seat plate 2203 thereby blocking flow from the high pressure inlet chamber to the low pressure exit ports. For the platen assembly to lift, the interior chamber 2211-IC pressure must be reduced. This is achieved by energizing the solenoid coil, which deflects the solenoid return spring 2216 and lifts the attached interior chamber valve seat 2217 away from the top of the capillary tube 2208, ultimately exposing the tube's opening to the pressurized air in the interior chamber 2211-IC. As this occurs, air/pressure leaks out of the interior chamber 2211-IC via the capillary tube 2208 and runs to a low pressure sink 2220-S (exhaust). The interior chamber 2211-IC is now entering a controlled leak state and can allow both inward flow from the pilot flow tube 2221 and outward flow via the capillary tube 2208.

The depressurization of the interior chamber 2211-IC goes through several stages. With the opening of the capillary tube 2208, and with the subsequent fall of the interior chamber 2211-IC pressure, the force on the top of the platen assembly diminishes until it is insufficient to compensate for the high pressure air in high pressure inlet chamber 2202-HC, which will always attempt to lift the platen seat upwards (with respect to the representations of FIGS. 21 to 26). As a result, the force on the top of the platen assembly is no longer able to sealingly hold/press the platen assembly against the seat plate 2203.

After passing the above discussed equilibrium state, the platen assembly will lift away from the seat plate 2203 allowing air to escape from the high pressure side HPS to the low pressure side LPS via the orifices 2203-O.

As mentioned earlier, air is able to flow into the interior chamber 2211-IC via the pilot tube connection port 2211-P and does so as soon as air begins to flow out of the capillary tube 2208. The system now seeks a balance point.

At this instant, there is an unsustainable gap between the top of the capillary tube 2208 and the interior chamber valve seat 2217. If pressurized air drains from the interior chamber 2211-IC via this gap faster than it can be replenished by the pilot flow tube 2221 the interior chamber 2211-IC pressure continues to fall. As pressure falls it reduces the downwards force on the platen assembly which in turn rises. Throughout this description it should be noted that, in the interest of succinctness and simplicity, terms such as rising and falling, or moving up or moving down, are used with references to the illustrating FIGS. 21 to 26, in which the valve is vertically orientated. However, in the general case, the valve may be oriented not only vertically, but in any other direction. Thus, the above description should not be considered as a limitation, but as an illustration of the general case, where the movement is defined with respect to the locations of the various components with respect to each other. For example, the described case of the platen assembly rising as the interior chamber pressure falls, should be considered as an illustration of the general case where the movement is described as the platen assembly moving away from the seat plate 2203.

As the platen assembly rises, it brings with it the capillary tube 2208, which begins to close the gap between its entrance and the interior chamber valve seat 2217. The reduced distance begins to limit the flow escaping through the capillary tube. This motion will continue until a balance point is reached where the air flowing into the interior chamber via the pilot flow tube is equal to the air being bled through the capillary tube, thus equalizing the pressure related forces acting on the upper and the lower surface of the platen.

The system will always attempt to stabilize in this manner. The end result is that the capillary tube 2008 will follow the motion of the interior chamber valve seat 2217, albeit delayed and whilst maintaining a small distance from it. Given this property, it is possible to control the distance between the platen seat 2209 and the seat plate 2203 and hence the flow through the valve by moving the interior chamber valve seat up and down by a very small amount (in the case of this example design, about 0.007 inches of full travel can be achieved). Since the capillary tube is never required to touch the interior chamber valve seat (except during full valve closure or sudden change events), very small forces in the solenoid may be used to position the platen assembly by using system pressures to provide the necessary forces.

Generally, the valve device illustrated in FIGS. 21-31 may be considered effectively a servo-actuated flow control valve that amplifies a small actuation force with a limited stroke in order to control a larger flow stream. The small actuation forces allow for the use of a solenoid with lower electrical power requirements than contemporary electrically operated flow control valves. Such a device may also be suitable for implementation in non-therapy and non-medical applications, such as industrial flow control applications where the pressure and flow rates may be different from those mentioned in the therapy examples herein. For example, this valve may be implemented in industrial compressed air applications; such as where typical air pressures go up to 150 PSIG (pound-force per square inch gauge) and line sizes up to 2" in diameter (e.g., inside diameter). On the low pressure side, this device may serve in implementations, such as for tank blanketing applications, as low as 1 cm H2O output pressure.

Such a servo actuated flow control valve can be coupled with a sensor (pressure, flow, or other) and a controller, such as a PID controller, to provide control on the outlet of the valve, as mentioned in the therapy example. As such, the feedback control system can also be used in non-therapy and non-medical applications, such as industrial pressure control applications. As such, the pressures or flow rates described in this specification may have other suitable ranges not just as described in the therapy examples. In such cases, the valve components may be suitably scaled, such as by scaling the orifice sizes, diameter and area ratios, and diaphragm thicknesses, to address the varying pressure and flow rate demands. Proportional solenoids with higher magnetic strengths (and current consumption) can also be implemented in the valve to provide longer actuating stroke lengths and actuating forces than those described in the current example as may be desired.

I.3.4.3 Closed Loop Control

As described, the function of the valve is controllable via the motion of a proportional solenoid. Energizing the coil lifts the interior, chamber valve seat 2217 and the force and pressure balances within the system take care of the position of the platen assembly versus the seat plate 2203.

Use of a fast motion, short stroke proportional solenoid enables an extremely fast response. However, the system should be under closed loop control for such an operation. Thus, a Proportional Integral Derivative (PID) controller may be included so as to continually monitor the outlet pressure of the valve and use this to control energizing of the solenoid. In this example, a 0-12V proportional solenoid was used but others may also be implemented. The set up and tuning of PID controllers for this purpose is a well understood engineering activity.

I.3.2.4.4 Solenoid, Solenoid Spring, Solenoid Collar and Interior Chamber Valve Seat An embodiment of the proposed valve includes a proportional solenoid as a linear actuator to move the attached interior chamber valve seat 2217. In the current embodiment, the proportional solenoid, including elements (solenoid coil 2213, solenoid collar 2214, solenoid return spring 2216, and retaining collar 2218), is an existing commercially available component (e.g., see Clippard Model EVP Proportional Valve from Cincinnati, Ohio, US), but could be refined. The proportional solenoid effectively converts an electrical signal into a mechanical force through an induced magnetic field. The magnetic force is used to displace a moving element. In the case of this solenoid, the moving element is the solenoid return spring 2216 (also shown in FIG. 29) which deflects perpendicular to its plane of orientation under the action of the magnetic field. The interior chamber valve seat 2217 is affixed to the solenoid spring and therefore moves with it. Conventional solenoids have an on/off operation mode and typically act in one direction. The proportional solenoid uses the solenoid return spring 2216 as a return and control spring whose function is to balance magnetic force with the spring force, and deflect in a known manner. The magnetic force component increases in proportion to the inverse square of the distance from the magnetic field source. It is possible in certain conditions for the spring and the solenoid coil's core to get too close to one another or even to touch. If this happens, the magnetic force will increase due to the reduced or eliminated separation of components and the actuator will enter an unstable, positive feedback state and will "runaway", ultimately locking in an extreme position. This can only be retrieved by de-energizing the solenoid. As it would be discussed further in the text, the solenoid spring is nonlinear, since when the center of the spring is displaced from its equilibrium position, the return force is non-linearly proportional to the displacement distance. The non-linear return spring characteristics can be customized to be capable of following and matching the non-linear relationship between magnetic force and distance. This results in an actuator whose physical displacement follows a near linear response with respect to applied voltage.

Figure 29:
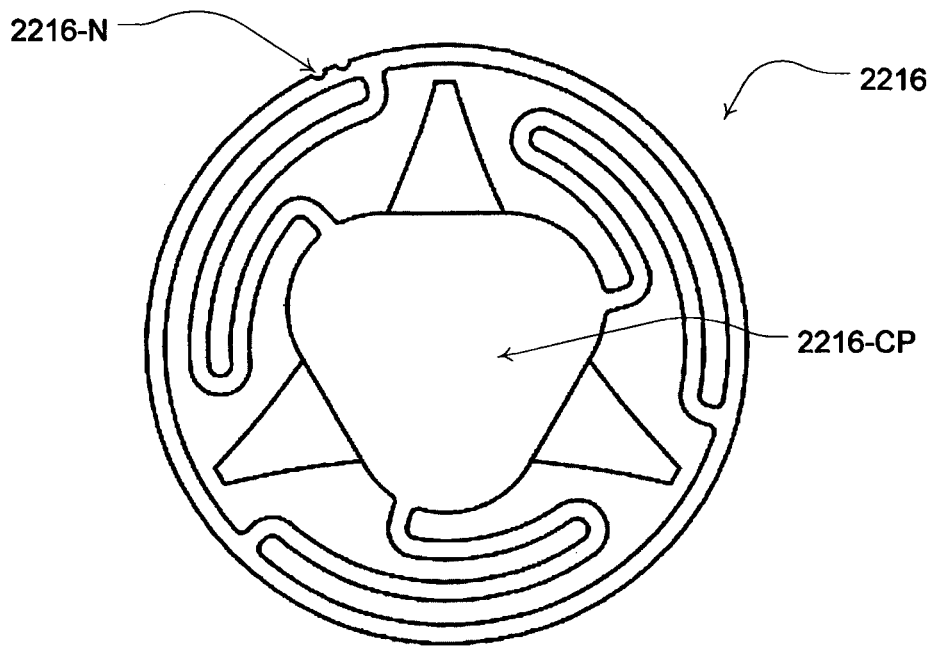
FIG. 29 is a plan view of an example solenoid spring that may be implemented with a compensator discussed herein, such as the example of FIG. 21.

The solenoid return spring 2216, such as the example shown in FIG. 29, is a mechanical component that exhibits a non-linear response and enables the proportional operation of the solenoid. The perimeter is keyed or notched 2216-N for positive location in the assembly. The outer ring is retained by the solenoid retaining collar 2218 (as best seen in FIGS. 25A and 26A) and the interior chamber valve seat 2217 is fastened to its central plate 2216-CP

I.3.2.4.5 Platen Top

The platen top 2207 is part of the platen assembly. It acts as a stroke limiting device to prevent runaway of the solenoid and locking the valve in the open position. The platen top at the upper limit of the stroke bears against the retaining collar 2218. This prevents the solenoid return spring 2216 getting too close or coming in contact with the magnetic core of the solenoid. Grooved channels 2207-GC (best seen in FIGS. 25A and 26A) provide a path for air to the entry of the capillary tube 2208.

I.3.2.4.6 Pilot Flow Tube

The pilot flow tube 2221 is a significant component in the valve assembly. It provides fluid (gas) connection or flow path between the high pressure inlet chamber 2202-HC and the interior chamber 2211-IC. It is a flow resistor designed to only allow a small flow of air into the interior chamber 2211-IC and a controlled pressure drop at a known flow. This then allows for the fine control of the valve through the relative positioning of the interior chamber valve seat 2217 and the entry to the capillary tube 2208, as explained in the following text. One version may be formed from a narrow bore tube (such as one in the range of about 0.1-0.8 mm internal diameter). It should be noted that for a given flow, the resistance of the pilot flow tube 2221 should exceed that of the capillary tube 2208 that acts as an air/pressure leak path for the interior chamber 2211-IC. If this is not the case, the pressure release through the capillary tube 2208 may be unable to compensate sufficiently for the increase of pressure supplied by the pilot flow tube 2221, thus causing difficulty in balancing flows and forces within the interior chamber 2211-IC via the gap between the interior chamber valve seat 2217 and the top of the capillary tube 2208. One possible outcome of mismatched tubes resistance, resulting from air/pressure being fed into the interior chamber 2211-IC faster than it can be drained through the capillary tube 2208 is the valve locking shut.

Figure 28:
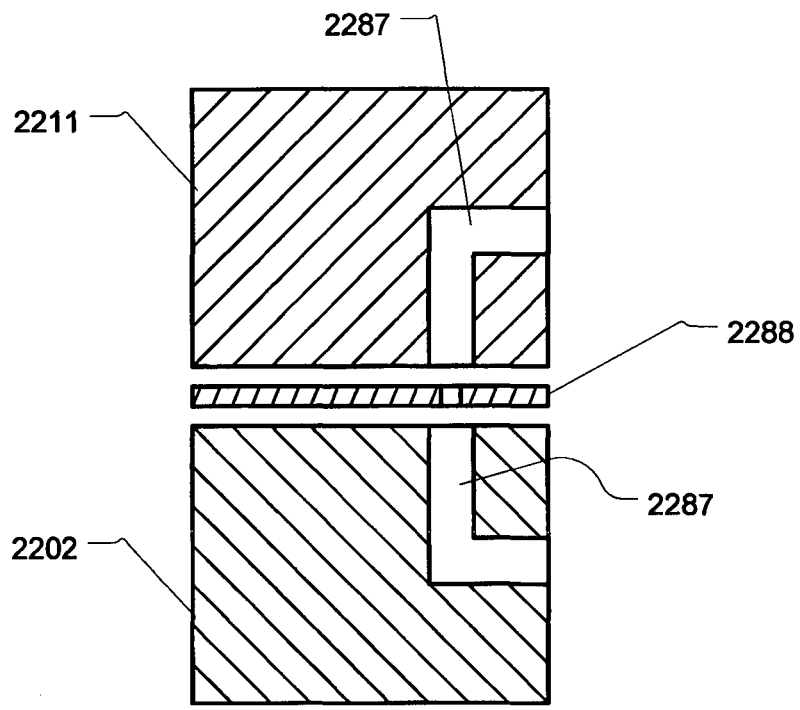
FIG. 28 is a cross-sectional illustration of an alternative resistance flow path to a pilot flow tube that may be implemented with a compensator such as the version of FIG. 21.

Alternate structures may provide the function of the pilot flow tube 2221. For example, an Orifice plate, porous media (such as a sponge or foamed material), a woven mesh, filter media, a pierced foil plate, a grub screw impinging on a flow path or an external valve may serve as a resistance flow path between the pilot tube connection ports of the upper and lower bodies. In an alternative example, the current pilot flow tube function could be incorporated into the walls of the upper and lower housings using aligned drilled holes in the upper and lower housing components. In another embodiment, it is possible to use mating drillings of a diameter larger than the capillary tube 2208 provided that a flow restrictor such as an orifice plate (flow restrictor) is included in the fluid path. An example is illustrated in FIG. 28 The upper body 2211 and lower body 2202 include integrated flow conduits 2287. Interposed between the flow path of each is an orifice plate 2288 configured to provide the desired flow resistance.

I.3.2.9.7 Seat Plate Design

The proportional solenoid valve, such as the one illustrated in FIGS. 21 and 22 is actually a flow control valve. However, it is configured so that the flow control effectively regulates the required pressure. This duty is possible because of the valve's fast response. A flow control valve configuration was chosen because this form of design allows for small valve sizes and relatively low internal forces. Traditional pressure control valves require large differential pressures and require large forces to operate. This is not feasible for this design as it is intended to operate in therapy conditions where the pressures, and hence available forces, are very low. At least some main applications of the valve are envisaged to be not only located in a user's (or patient's) home, but also on or near the user's mask, a small size, quiet and safe operation are also a significant design concern for the valve.

Common flow control valves use a similar arrangement to the one presented in this design with at least one fundamental difference. Where this valve's seat plate uses an array of small holes, a common flow control valves typically employ a single large hole. In some cases, a single hole assists manufacturing simplicity. However, it increases the size of and forces acting within a valve. These forces may be considered with reference to FIGS. 27A and 27B. In FIG. 27A, a typical flow control valve configuration is shown that has the combination of a single hole and a lifting plate to control flow. As the top plate lifts, a greater flow will be permitted to travel through the valve and will eventually reach a limit based on the size of the hole. This is so, because any fluid passing though the valve must first pass axially through the hole and then secondly it must flow transversely between the top and bottom plates. In doing so, it spreads outwards through the walls of a virtual cylinder formed by the hole's perimeter and the valve lift height (L). For small valve lifts, there is relatively little cylindrical (transverse) flow area compared to the hole flow area and it is, therefore, the cylindrical transverse flow area that provides flow limitation. If the lift is increased dramatically such that the cylindrical transverse area is large compared with the hole flow area, the dimension of the hole becomes the flow limiting element.

It can be shown that this happens for lift heights (L) of between ¼ to ⅓ of the diameter ($D_1$) of the hole. The reason for this lies in the axial and transverse flow areas and their relationship to one another.

In more detail, as the air travels, its passes first through the hole's orifice where the flow area is governed by the orifice diameter: $A_o = \pi/4 * D_1^2$. Once it passes through the orifice it changes direction and travels substantially horizontally, spreading out through a transverse, cylindrical flow area (indicated by dashed lines in FIGS. 27A and 27B) whose area is $A_c = \pi L D_1$. With the diameter fixed, it can be seen that the valve lift height (L) directly controls this cylindrical flow area. If the lift height (L) is increased, the cylindrical flow area increases linearly. Since the flow must pass through the hole first and the cylindrical area second, it can be seen that whichever of these two flow areas is smallest, will be the major flow limiting element. A theoretical optimum point is reached when the flow areas are equal. From these equations is can be shown that the theoretical optimum diameter of an orifice for a given lift height is D=4L. In practical terms, it is often observed that this limit may settle around D=3L as some of the cylindrical flow area is wasted due to flow inertia causing the flow to crowd around the top plate as it changes direction.

To increase the rate of flow through a single orifice valve for a fixed lift distance (L) one must increase the diameter of the orifice. This provides additional cylindrical flow area (and hence additional flow) proportionally with the increase in diameter (see the formula for $A_c$ above). While this is a simple solution, the problem becomes one of forces. The force tending to lift the top plate is based on the orifice area $A_o$, not cylindrical flow area $A_c$. If one doubles the diameter of a single orifice, the flow in the valve doubles, but the forces acting on the top plate, which are a function of orifice area, increase by a factor of four. Increased forces bring control difficulties.

In the case of the newly proposed design, a different approach has been taken to optimize the size of the flow orifice for the expected level of lift (e.g., about 0.007 inches in this design). This particular example leads to an optimum orifice diameter of about 0.028 inches. As a single orifice of this diameter will not supply the required flow, multiple orifices are used.

By example: in the case where a single 0.5" orifice is needed to supply flow, the ideal and limiting valve lift height value would be 4×0.5"=0.125". In the case of the valve being described only 0.007" stroke is available (due to mechanical constraints elsewhere in the valve). Therefore, only approximately 5.6% of the needed cylindrical flow area is possible. The forces in the valve are governed by the area of a 0.5" diameter hole. To achieve the correct flow a much larger hole is needed, which would be associated with yet larger forces.

Alternatively, if we used multiple holes (e.g., 24) of $D_2=0.028"$ (as illustrated in FIG. 27B) a greater cylindrical flow area may be achieved than the single orifice version but with only 7.5% of the total orifice area. In other words, by using multiple orifices it is possible to achieve the equivalent flow of a large, single orifice but with drastically reduced orifice area and hence drastically reduced internal lifting forces. This reduced the complexity of the design. The use of multiple holes also allows a short stroke of the solenoid, which is beneficial for the quick response of the system.

I.3.2.4.7.1 Seat Plate Examples

Accordingly, the step down surface between the high pressure side HPS and the low pressure side LPS of the valve component that separates the high pressure inlet s 2202-HC from the low pressure outlet chamber 2202-LC may include a set of orifices (e.g., multiple fine holes that may satisfy the above design calculations). In the example above, this component is referred to as the seat plate 2203. Two example versions of the step down surface of the seat plate are shown in FIGS. 30 and 31.

In the example of FIG. 30, a set of round holes are arranged about the periphery of the step down surface of a cylindrical seat plate 2203. Such an arrangement permits their selective closure by contact with a ring shaped surface of the platen seat 2209. An orifice of the central protrusion 2203-CP serves as a sleeve for the slidable insertion of the capillary tube 2208. As previously mentioned, optional channels 2203-CH along the periphery provide a low resistance path for a radial movement of the air. This allows for a more uniform distribution of the pressure in the area. The set of holes comprises two concentrically disposed circles with the holes of the circles being staggered with respect to each other. Other arrangements, where the holes are distributed in different arrangements or randomly, are also possible.

The version of the seat plate of FIG. 31 is comparable to that of FIG. 30. However, in the version of FIG. 31, to even further improve the flow between the platen seat 2209 and the valve seat plate 2203, boundaries of the orifice set are raised above the surface of the seat plate. In this example, tube portions 2203-T are embossed on the surface, the space between them providing low resistance path for the air to flow around.

As such, the component may include any geometry to reduce resistance to flow between the platen seat 2209 and the valve seat plate 2203 by the introduction of narrow raised structures to surround each orifice. In the example, hollow bosses protrude from each flow path through the seat plate 2203. These provide additional clearance between the large, planar surfaces of the platen seat 2209 and the seat plate 2203. Once the air passes through the seat plate flow paths and exit the boss orifices or raised set of orifices, it meets a low impedance path which reduces undesirable pressure loss. The end result is that higher flow rates may be achieved through the valve for a given input pressure. This is desirable as it allows for lower input pressures to be used with the valve. These structures address a flow restriction issue that is related not to losses associated with the orifices themselves but with their surrounding area. Thus, this solution is distinct from the phenomena of lift height versus orifice diameter explained previously.

The elevated bosses also serve to increase the sealing stresses on the seat surface around the orifices, which has the effect of giving the valve better closure (turn-down ratio). The raised bosses further ensure that the pressure surrounding the orifices is very close to the low outlet pressure. With the alternative arrangement having a flat plate with openings on the surface, there could be a local build-up of pressure in the center of the seat plate slightly higher than the low outlet pressure, due to the limited escape area. Such slight increase in pressure can cause an undesirable opening bias and make the valve slower to close.

I.3.2.4.8 Capillary Tube Exhaust

As previously mentioned, in some versions the capillary tube exhausts using the ambient atmosphere as a low pressure sink 2220-S such as at the base plate 2220. In other versions, the capillary tube may be configured to exhaust to one or both of the low pressure exit ports 2202-X1, 2202-X2 thereby using waste flow exiting the capillary tube to contribute to the volume of therapy air delivered to the patient. This may also serve to reduce noise generated by the valve.

I.3.2.5 Pressure Divider Valve Example

In some cases, a pressure divider valve may be implemented to either reduce the high incoming pressure down to a suitable mask pressure or to simply regulate the pressure within specific boundaries. One such example may be considered with reference to FIGS. 32A, 32B and 33. In this example, an air pressure/flow delivery mask 3208 includes an integrated divider valve 3222 or a coupler 3223 (e.g., swivel elbow) with such a divider valve 3222. The divider valve may include a multi-sectioned piston 3227 shown in more detail in FIG. 33. The piston includes first and second ends 3227-E1, 3227-E2 having different diameters and, therefore, areas. The respective piston activation chambers 3229-C1, 3229-C2 of the valve in which the piston ends traverse may then have comparably different chamber diameters and transverse areas. These diameters and areas are associated with the diameters and the areas of the respective faces of the piston ends 3229-E1 and 3229-E2.

Figure 32B:
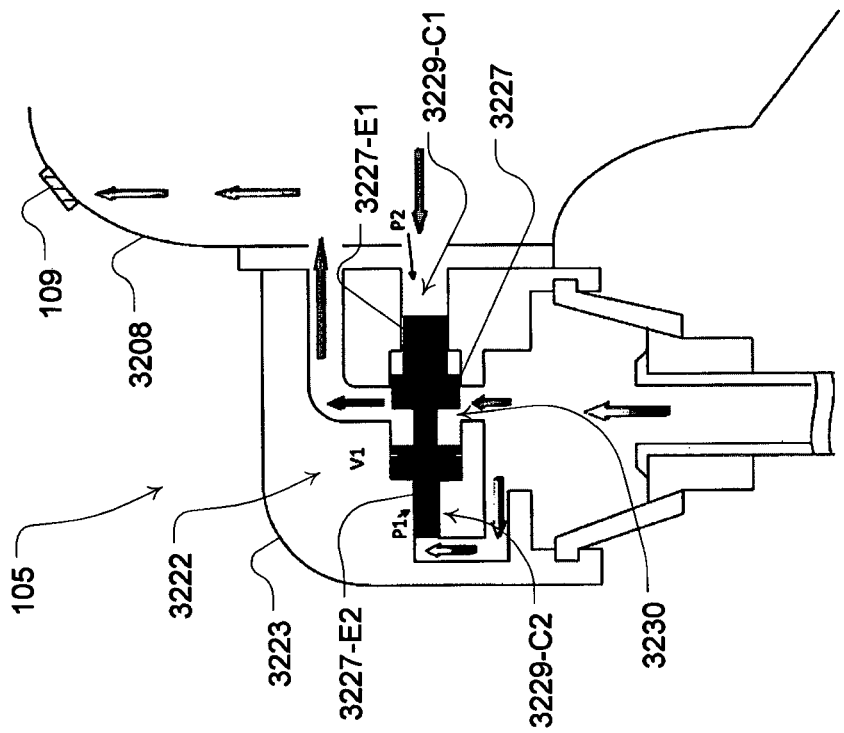
FIGS. 32A and 32B are side view illustrations of a patient interface with a treatment compensator employing a piston assembly that may be suitable for some versions of the present technology.
Figure 32A:
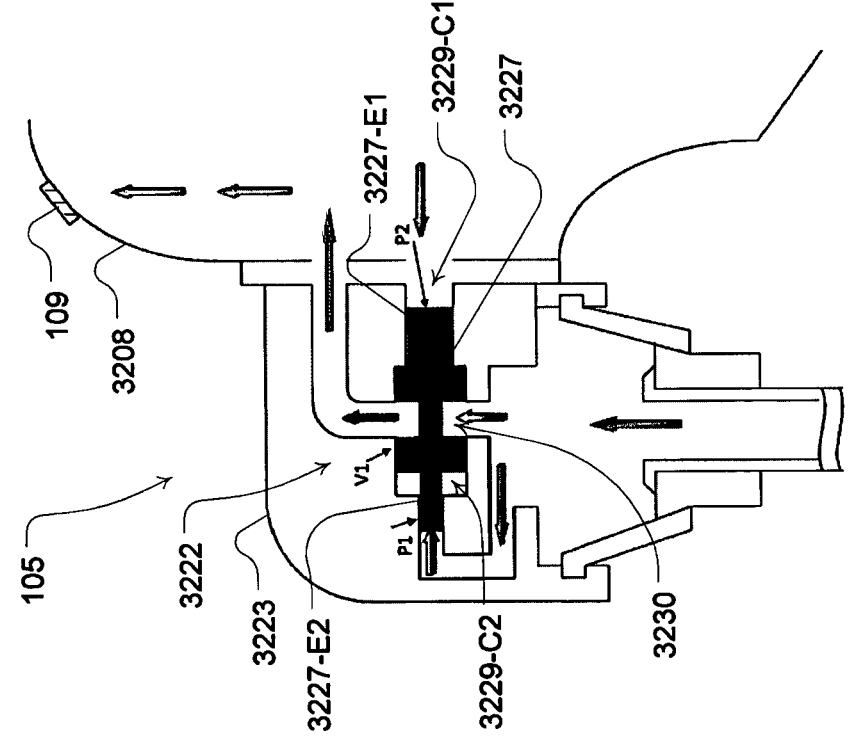
Figure 33:
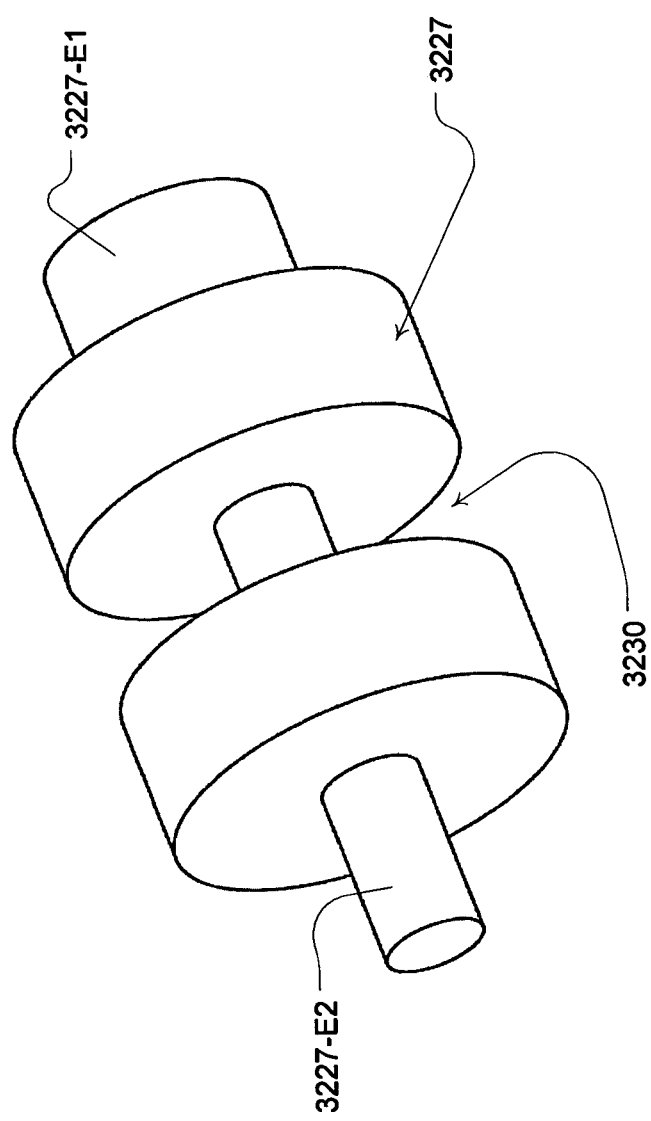
FIG. 33 is a perspective view of an example piston that may be implemented in some versions of the compensator of FIGS. 32A and 32B.

The face of one of the ends 3227-E1 may be exposed to the mask pressure (e.g., in chamber 3229-C1) and the face of the other piston end 3227-E2 may be exposed to the upstream pressure on the flow pressurizer apparatus side of the treatment compensator (e.g., in chamber 3229-C2). As such, the divider valve may be designed with different area ratios so as to permit suitable activation of the valve. Based on the specific ratio, the piston of the valve may traverse so as to selectively increase or decrease a passage to the mask of a piston orifice 3230 through the piston. In this regard, a larger opening of the piston orifice 3230 is illustrated in FIG. 32A and a smaller opening of the piston orifice 3230 is illustrated in FIG. 32B.

For example, the divider valve may be designed to have a balance at a ratio of 4 to 1 so as to step down the pressure by that ratio. In the examples below, the input high pressure side (P1 on FIGS. 32A and 32B) may then be for example, 40 cm $H_2O$, and the mask pressure side (P2 on FIGS. 32A and 32B) may then be kept at 10 cm $H_2O$ positive pressure given the piston ratios. Such operations of the valve may be implemented for various treatments.

For example, a continuous positive airway pressure (CPAP) type device may be configured to deliver a generally constant pressure such as about 40 cm $H_2O$, which may be regulated by a control loop of a controller of the flow generator of the CPAP device using an internal pressure sensor in a typical way. This pressurized flow may be delivered by a fine bore conduit (e.g., a 10 mm diameter tube the 10 mm tube example was chosen since the cross sectional area is approximately one fourth (4) that of a standard 19 mm mask tube). When high pressure enters the mask swivel elbow (coupler 3223) the divider valve is open as shown in FIG. 32A and air fills the mask till 10 cm $H_2O$ is reached. As shown in FIG. 32B, once the large area piston end 3227-E1 shown at P2 is exposed to a pressure that is about a ¼ of the incoming high pressure, it closes (e.g., reduces) the flow path of piston orifice 3230 reducing the airflow as the force at P2 is greater than the force P1. However, with the closure of piston orifice 3230, P2 is progressively reduced until the force at P1 becomes greater than at P2 and the flow path of piston orifice 3230 will start to open again, letting more air flow through the orifice and increasing P2 once again.

For PAP systems that automatically adjust the treatment pressure, such as in the response to the detection of sleep disordered breathing events (e.g., upper airway obstruction, flow flattening, etc.) when the therapy requires an increase in mask pressure due to leak or treatment, the controller of the flow generator may then set the desired increase in pressure as a multiple of the piston ratio (e.g., by multiplying pressure by 4.) For example, to increase mask pressure from 10 to 12 cm $H_2O$ to treat an obstruction, the flow generator of the automatically setting PAP device may control an increase in pressure from 40 to 48 cm $H_2O$ so that the pressure may be stepped down to the desired range in the mask. Furthermore, other adjustments to the setting of the pressure at the flow generator may also be made such as to account for friction losses etc. that may affect the pressure arriving in the mask.

An advantage of such a system lies in the simplicity of its construction. It can in some cases eliminate complex electronic sensors and the need for extra wires embedded in the delivery conduit. Existing pressure and flow sensors located within the flow generator may then be able to calculate the mask pressure, such as without sensors in the mask, similar to calculating tube pressure drop but also by taking into account the step down ratio attributable to the piston valve.

I.3.3 Pressure Sensor

The pressure sensor 1426 senses the therapy pressure and may convert it into an electrical signal representative of therapy Pressure value. It can be a gauge type sensor or an absolute type. It may have an appropriate operating pressure range for the therapy pressures (e.g., in a typical range of about 0-30 cm $H_2O$). An example of such a device is a Honeywell P/N X203767 pressure sensor. The pressure sensor may be located on the respiratory mask or in one of the controlling devices, such as the treatment compensator 105.

I.3.4 Expiratory Relief Valve

As illustrated in FIGS. 14, 16 and 17, a relief valve 1424 may optionally be included. The valve may be implemented to serve as an expiratory relief valve. Such a valve can provide expiratory pressure relief so as to provide any or additional outgoing venting to ambient air during expiration. Such relief can reduce or completely eliminate an uncomfortable feeling of a therapy pressure that increases with the patient's breathing out.

The relief valve may also act as a safety device. It may be configured to prevent the therapy pressure from exceeding the specified safety levels. For example, it may adjust the relief, valve if a detected pressure exceeds a safety threshold.

Generally, these operations are achieved by opening an extra air path to atmosphere to reduce the therapy pressure in the conduits proximate to the patient. Such opening may be of the proportional type where the valve opens gradually maintaining the pressure relief, or of ON/OFF style with only two stages (open or close), depending on the configuration and function of the valve.

The relief valve can be directly controlled or activated by the therapy pressure itself, which is the pressure in the respiratory mask, and/or by a processing unit of the valve controller 1420. In the case of the controller, it will monitor a measure of the actual therapy pressure and produce a relief valve control signal to set the relief valve either during the expiratory breathing phase or when the therapy pressure reaches or exceeds a critical safety value(s).

Any suitable relief valve may be implemented. Moreover, whilst the relief valve has been described as a separate valve, in some versions of the system, its functionality can be accommodated, partially or entirely, by control of the valve 1422.

I.4. Patient Interface

In at least the cases illustrated in FIGS. 14 and 16, the compensator is coupled with a patient interface 1408. For example, a conventional PAP mask 1407 may be included, which comprises a vent 109. This may take the form of an integrated vent, a tube cuff mounted vent or other versions as desired. In some cases, this would represent a conventional, integrated mask vent included in the mask's frame, cushion or similar.

In some versions, a coupler, such as a conventional elbow with an anti-asphyxia valve, may be implemented between the compensator and the patient interface. In some cases, the compensator may be more integrally configured with the patient interface, such as being a component or an integral component of the mask. In some cases, such as with the inclusion of the optional relief valve 1424, a non-vented mask may be implemented. One such example is a ResMed Mirage Quattro FX Non-Vented mask. Moreover, in some examples, masks including or coupled with active venting technologies may also be included. For example, any of the adjustable vents described in International Patent Application No. PCT/US12/55148 filed on Sep. 13, 2012 may be included, the entire disclosure of which is incorporated herein by reference.

I.5 Reservoir(s)

In some versions, such as the one illustrated in FIG. 16, one or more optional reservoirs may be included. Such a component may be implemented as an air and pressure storage volume. One such reservoir 1660 may be located near the flow pressurizer apparatus 1404. It may serve as a buffer to reduce peak demands on the flow pressurizer apparatus 1404. Such a reservoir may supply supplemental pressure or flow to the system or delivery conduit. It may respond to system perturbations so as to avoid rapid changes in output from the flow pressurizer apparatus 1404. A further valve system of the reservoir may then be configured to ensure that the operating pressure range is controlled. Since the reservoir 1660 may be located near the flow pressurizer apparatus 1440, the reservoir 1660 may be a larger unit (e.g. volume) but may also be located discreetly away from the patient (e.g., under the bed).

Additional reservoirs may also be implemented. For example, a further optional reservoir 1660-1 can be configured to operate as reservoir 1660. However, it may be located more proximal to the patient on the high pressure side of the treatment compensator 105. Being in this position, close to the compensator, this reservoir 1660-1 is close to the patient so it may be a smaller size (e.g., volume). When it is close to the compensator, its response time in delivering supplementary pressure/flow is reduced, which may improve the control of the system. Any reservoirs included in the system may act as mufflers, the reduced noise being beneficial for the user's comfort.

I.6 Example Operations

In the examples, such as that shown in FIG. 14, the flow pressurizer apparatus 1404 generates and delivers high pressure air to the entry of the fluid conduit at pressures in a desired range such as that of about 140-200 cm $H_2O$ gauge pressure. This air travels along the delivery conduit (e.g., fine bore conduit 106), losing static pressure due to the frictional characteristics of the tube and flow therein.

In the configuration with a conventional CPAP mask with a vent, mask venting occurs throughout the breathing cycle. The system will supply the flow of both the patient and the vent, when present, and can do so during peak inhalation conditions. The summation of these flows combined with characteristics of the conduit dictate any static pressure losses. Depending on the type of mask and breathing characteristics of the patient, these losses may typically be in the range of about 40-80 cm $H_2O$ pressure, although larger ranges are possible.

The system is configured such that characteristic conduit losses bring the static pressure down to the range of the desired control valve input pressure (e.g., about 70-140 cm $H_2O$). The control valve system will then operate to leak this relatively slow, high pressure air in order to supply controlled, low pressure output suitable for the patient at a suitable flow rate(s).

A significant element of this system is the treatment compensator and its valve controller. It can perform the function of regulating electro-mechanical elements so as to ensure correct output pressure. In the case of closed loop control, a PID controller can be implemented to do so. In such a controller, the derivative (D) term may be minimized or set to zero to avoid detrimental effects of numerical derivatives on noisy data.

In some cases, the pressure sensor may be electronic (either with either digital or analog outputs) as previously discussed. In some cases a purely mechanical (i.e., analog) device for sensing and reacting to pressure may be included. Thus, the pressure sensor may be understood to mean an electronic sensor or a pressure type that feeds pressure to a diaphragm which in turn pneumatically actuates valve elements based on the balance of pressures (analog). In some cases, the controller elements can include mechanical assemblies of springs, levers, pistons, etc., designed to affect a mechanical response to achieve closed loop control.

A pressure profile may be generated from the system in real time (representing the therapy itself) and may either be determined by the valve controller 1420 of the compensator (e.g., as a constant value in the case of simple CPAP therapy, bi-level or other smooth pressure curve) or by a therapy engine of the flow pressurizer apparatus 1404 or flow generator by real-time setting of a target pressure. In some cases, this functionality may be included in the valve controller 1420 such that at least some control functions of the therapy engine reside (e.g., as programming instructions) in the valve controller 1420 itself.

In addition to this controller, the actuation devices mechanically act on the valve, or on physical elements of the valve, in order to adjust the pressure. These elements will be manipulated dynamically and/or in real time to account for the varying pressures and flows resulting from patient respiration.

In some cases, such as that illustrated in FIG. 14, an actuator may be integrated into the valve 1422 such as when the valve is implemented with a proportional solenoid. In some cases, such a solenoid may have a full scale displacement of about 0.007 inches and a coil energizing voltage range of about 0-12V. In this case, the valve controller 1420 monitors pressure from the pressure sensor 1426 and responds by generating a controller effort signal that may be in the form of a voltage applied to the solenoid coil of the valve 1422 that in turn adjusts the valve's output pressure.

In alternative embodiments, control of the mechanical valve elements may be via controller effort in the form of a mechanical signal (actual force) such as when the actuator is classified as being "inside" or part of the valve controller 1420, rather than in the valve 1422 itself.

One particular feature of some versions of the system is its ability to reduce expiratory back pressure via a pressure relief system. In the example of at least FIG. 14, proportionally opening an exhaust port (e.g., of a relief valve 1424) controlled by the valve controller 1420 can reduce this expiratory back pressure. In conventional respiratory therapy systems, it is common to use the delivery conduit, tube as a temporary storage tank for exhalation gases that cannot be instantly discharged via the mask's vent. When this occurs the patient pushes air into the tube against the action of the flow generator. This works best when the tube is a low impedance path and may be assisted by an expiratory pressure relief system designed to reduce blower output during exhalation. During the latter stages of exhalation, when patient flow rate is low, the gas previously pushed back up the tube returns to the mask cavity where normal vent flow attempts to wash it out prior to the patient's next inhalation.

This system behavior may be prevented in the proposed system if:

A high impedance version of valve 1422 is included in the circuit that will close as exhalation raises pressure above the valve's current pressure target;

High upstream pressures are present from the flow pressurizer apparatus 1404; and/or The main fluid conduit from the flow generator is a relatively high impedance path (e.g., a fine bore conduit).

Without expiratory pressure relief it is possible for the patient to exhale when the system includes a vented mask. However, the back pressure experienced by the patient is determined by the flow and pressure characteristics of the mask's venting arrangement. Typically, this will cause a pressure rise in the mask cavity and may feel unpleasant to the patient.

Inclusion of a pressure relief system, such as with the relief valve 1424, is a desired approach for alleviating this issue. As mentioned earlier, such a valve may be a proportionally controlled exhaust port and may be implemented with those known in the art.

Such pressure relief may be implemented with an active vent. Depending on the configuration of the system, the inclusion of an active vent may complement the action of, or even negate the need for, a conventional mask vent. This has several performance benefits for the system. In the configuration where the proposed system includes an active vent and is used in conjunction with a non-vented mask, the overall air demand on the blower may be reduced significantly. During inhalation, the vent may be set as closed, thereby eliminating unnecessary vent flow and reducing the quantity of air needed to be supplied to the mask. As the patient exhales, the valve controller 1420 may halt or limit the pressurized air supply by partially or fully closing the valve 1422 ensuring that the active vent of the expiratory pressure relief system only needs to discharge the air exhaled by the patient and any minimal air allowed through the valve 1422. The combined effects of these behaviors, are a reduction in air demand from the flow pressurizer apparatus 1404 and a reduction in nuisances associated with conventional vents (e.g., air jetting, noise, feelings of coldness and/or discomfort).

I.7 Potential Benefits

As mentioned earlier, whilst being attractive from patient's convenience point of view, small air delivery conduits carry penalties in the form of increased impedance and inertance that may lead to control difficulties and patient discomfort.

In conventional system architectures the blower's rotation speed ultimately controls all pressures and flows within the system. In this case, the provision of stable and reliable therapy becomes increasingly difficult with the reduction of the diameter of the air delivery conduits, due to inherent limitations of this system. Aspects of rotational inertia, control system function, motor size and fluctuating pressure requirements render conventional architectures unsuitable below air delivery conduit internal diameters of approximately 11-12 mm.

The proposed technologies may allow the utilization of small air delivery conduits by altering the manner in which air is pressurized, supplied and ultimately controlled. It also changes the locations within the system at which this regulation is performed. First and foremost, the inclusion of a fast response valve 1422 removes the need for blower speed to be the direct controlling element of therapy pressure. The valve 1422 may be opened and closed much faster than a conventional blower can accelerate. In the case of a valve system described herein, full valve travel may be achieved in the range of 5-10 milliseconds, much faster than some blowers are able to respond.

The use of the valve 1422 can effectively disconnect blower rotation speed from being the direct controller of patient pressure such as the task may now be performed with the valve. It is then possible to implement new control methodologies for the primary air source's blowers. In conventional systems, the acceleration of blowers has to match the patient's breathing cycle exactly. In some version of the proposed system, it is now possible to sequence the acceleration of blowers to pre-empt patient behavior. For example, consider the case where a patient is exhaling and the valve 1422 is limiting air coming from the flow pressurizer apparatus. In some embodiments, the valve 1422 may be entirely closed for a period of time (such as if non-vented masks are used). During these conditions the output of a primary blower may be reduced (to save power and reduce noise) and/or use of the bypass duct may be engaged such as in the case of the implementation of FIG. 15. When the patient is reaching the tail end of exhalation, it is possible to begin increasing the blower output once again. However, this can be performed prior to the patient's inhalation cycle starting and thus prior to the point where flow demand experience high rates of change. In this way, it is possible to cater for a blower's relatively slow response time due to their acceleration cycles and via the interaction of the blower, delivery tube and valve 1422 provide smooth and pleasant breathing experiences on the downstream side of the valve of the treatment compensator.

This behavior also provides an elegant solution to the complex behavior of inertance. At the moment that a patient begins to inhale (i.e., at the transition between exhalation and inhalation), a large rate of flow acceleration is required. For a 7 mm internal diameter air delivery conduit, inertance effects require a pressure differential in the range of 2-5 cm $H_2O$ (or possibly larger depending on patient breathing performance) to be supplied instantly and maintained over the length of the conduit, over and above any impedance pressure loss.

Due to the difficulties of controlling flow acceleration within conventional architectures, the patient is likely to experience a moment where the blower is attempting to accelerate but cannot match the instantaneous inertance pressure requirement. The end result is that the blower is unable to accelerate air in the conduit fast enough and the patient experiences a momentary but significant pressure drop. This manifests as a feeling of needing to pull air from the air delivery conduit. This phenomena has been often termed as pressure swing or expiratory pressure drop.

The proposed system may avoid this eventuality in two ways:

(a) The system may maintain a pressure overhead such as 70-140 cm$H_2O$ across the valve 1422 such that sufficient pressure is always available to overcome tube inertance. In other words, instantaneous inertance pressure demands are easily supplied by a perpetual or sustained valve pressure overhead.

(b) Locating the valve proximal to the patient means that any inertance effects downstream of the valve 1422 are negligible. Inertance varies linearly with conduit length. Locating the valve near the patient substantially eliminates an inertance path on the low pressure side of the valve.

J. Further Example Flow Pressurizer Apparatus

J.1 Flow Generator Systems

Figure 34:
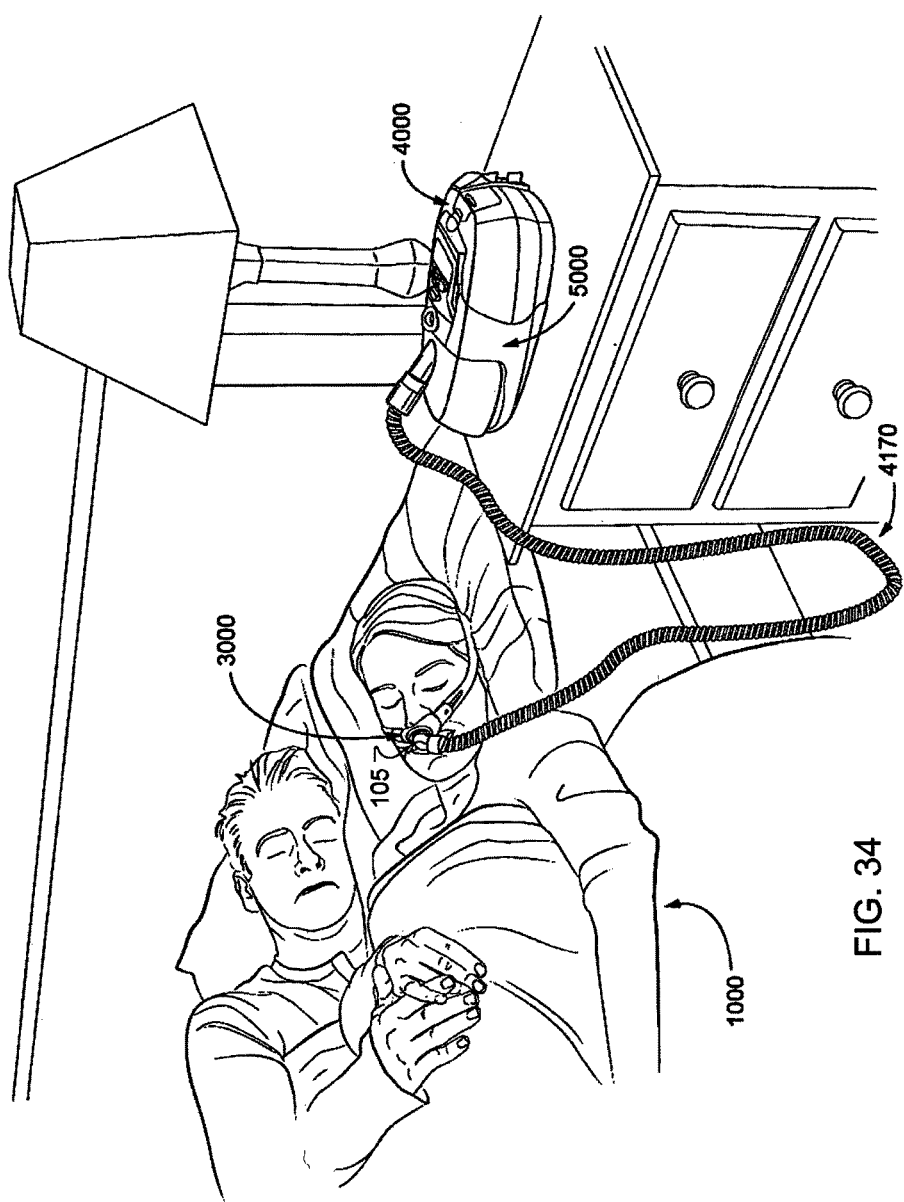
FIG. 34 illustrates another system in accordance with the present technology. A patient 1000 wearing a patient interface 3000, such as one with a treatment compensator 105, receives a supply of air at positive pressure from a PAP device 4000. Air from the PAP device may optionally be humidified in a humidifier 5000, and passes along an air circuit 4170 (such as one with a fine bore delivery conduit 106) to the patient 1000.
Figure 36A:
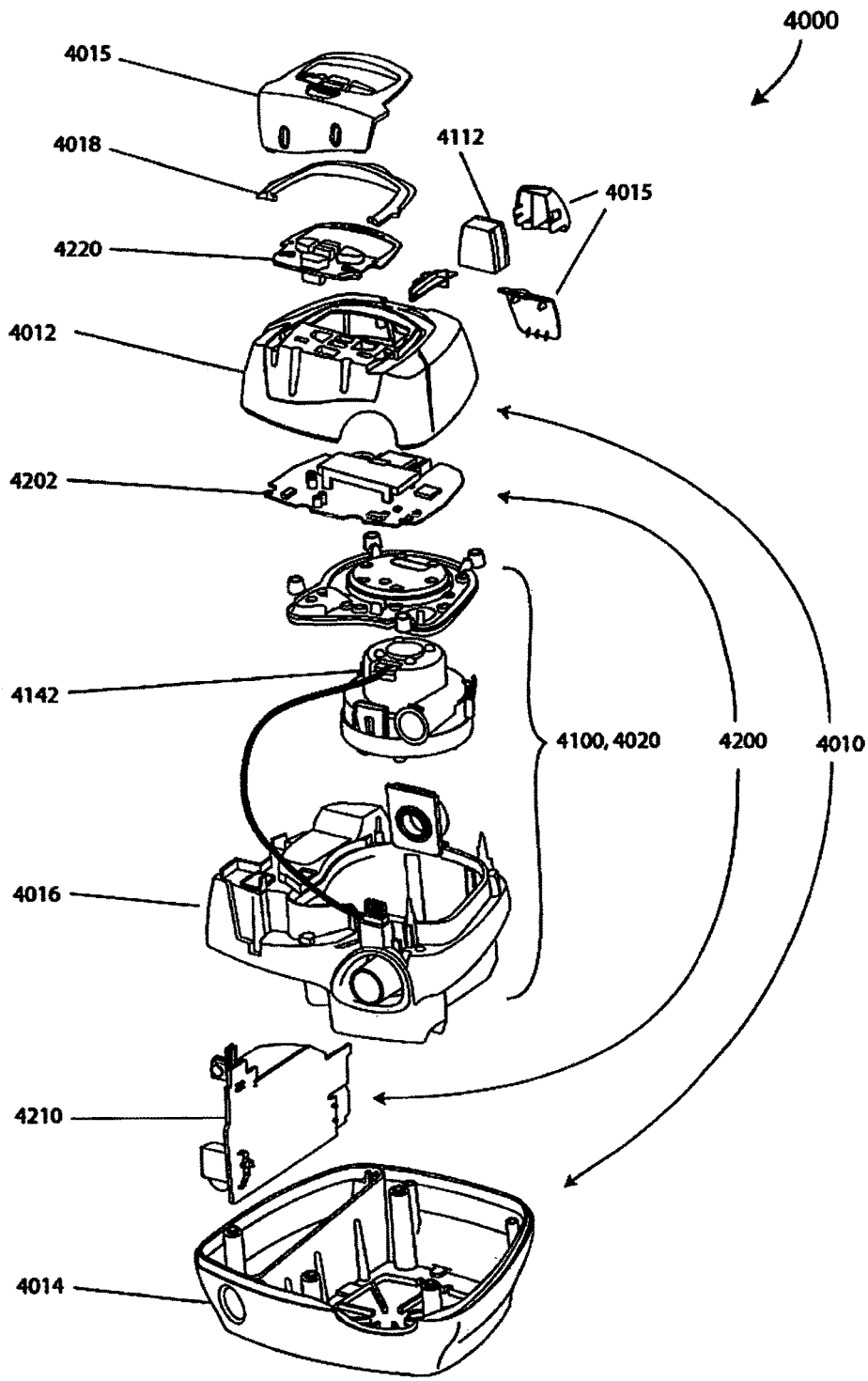
FIG. 36a shows a PAP device with components that may serve as a single stage blower or in a dual stage configuration in accordance with some versions of the present technology.

In one form, the present technology may form part of an apparatus for treating a respiratory disorder, such as that illustrated in FIGS. 34 and 36*a*. The apparatus may include a flow generator or blower configured as a flow pressurizer apparatus 104 for supplying pressurised respiratory gas, such as air, to the patient 1000 via an air delivery tube leading to a patient interface 3000.

J.2 Therapy

In one form, the present technology may serve as part of a method for treating a respiratory disorder comprising the step of reducing a generated positively pressure and applying the reduced positive pressure to the entrance of the airways of a patient 1000, such as to the nasal passages of the patient via one or both nares and/or the mouth. For example, the PAP device 4000 may generate pressures so as to provide with the treatment compensator a Nasal Continuous Positive Airway Pressure (CPAP) therapy to treat Obstructive Sleep Apnea (OSA) of the upper airway by pushing the soft palate and tongue forward and away from the posterior oropharyngeal wall.

The PAP device 4000 may generate pressures so as to provide with the treatment compensator a Non-invasive ventilation (NIV) such as has been used to treat Cheyne-Stokes Respiration (CSR), OHS, COPD, MD and Chest Wall disorders. In some cases of NIV, the pressure treatment may be controlled to enforce a target ventilation by measuring a tidal volume or minute ventilation, for example, and controlling the measure of ventilation to satisfy the target ventilation. Servo-controlling of the measure of ventilation, such as by a comparison of an instantaneous measure of ventilation and a long term measure of ventilation, may serve as a treatment to counteract CSR. In some such cases, the form of the pressure treatment delivered by an apparatus may be Pressure Support ventilation. Such a pressure treatment typically provides generation of a higher level of pressure during inspiration (e.g., an IPAP) and generation of a lower level of pressure during expiration (e.g., an EPAP).

J.3 Patient Interface 3000

Figure 35:
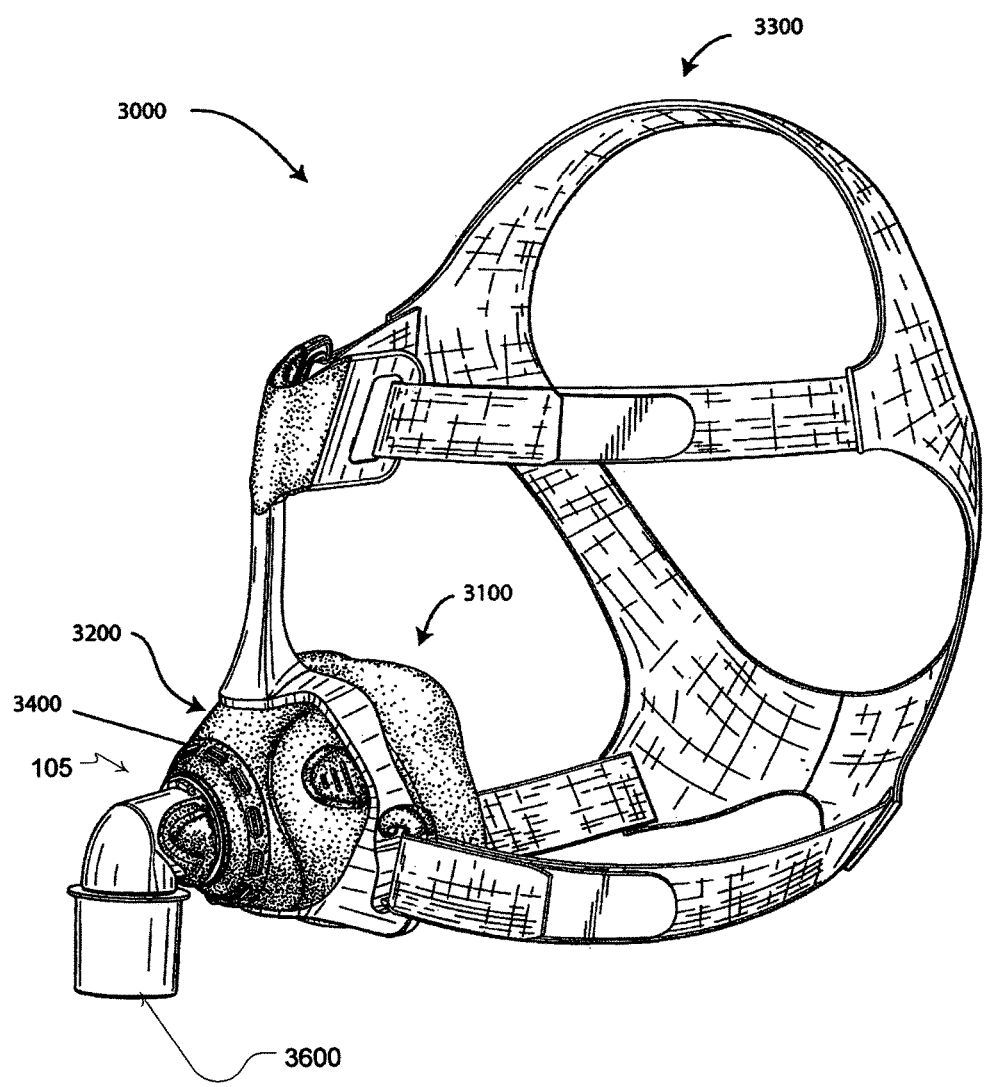
FIG. 35 shows a patient interface in accordance with one form of the present technology that may be coupled with a fine bore delivery conduit and/or integrated so as to include a treatment compensator.

As illustrated in FIG. 35, a non-invasive patient interface 3000 in accordance with one aspect of the present technology may include the following functional aspects: a seal-forming structure 3100, a plenum chamber 3200, a positioning and stabilising structure 3300 and a connection port 3600, such as one with an included treatment compensator, for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the compensated supply of air at positive pressure to the airways.

J.4 PAP Device 4000

Figure 36B:
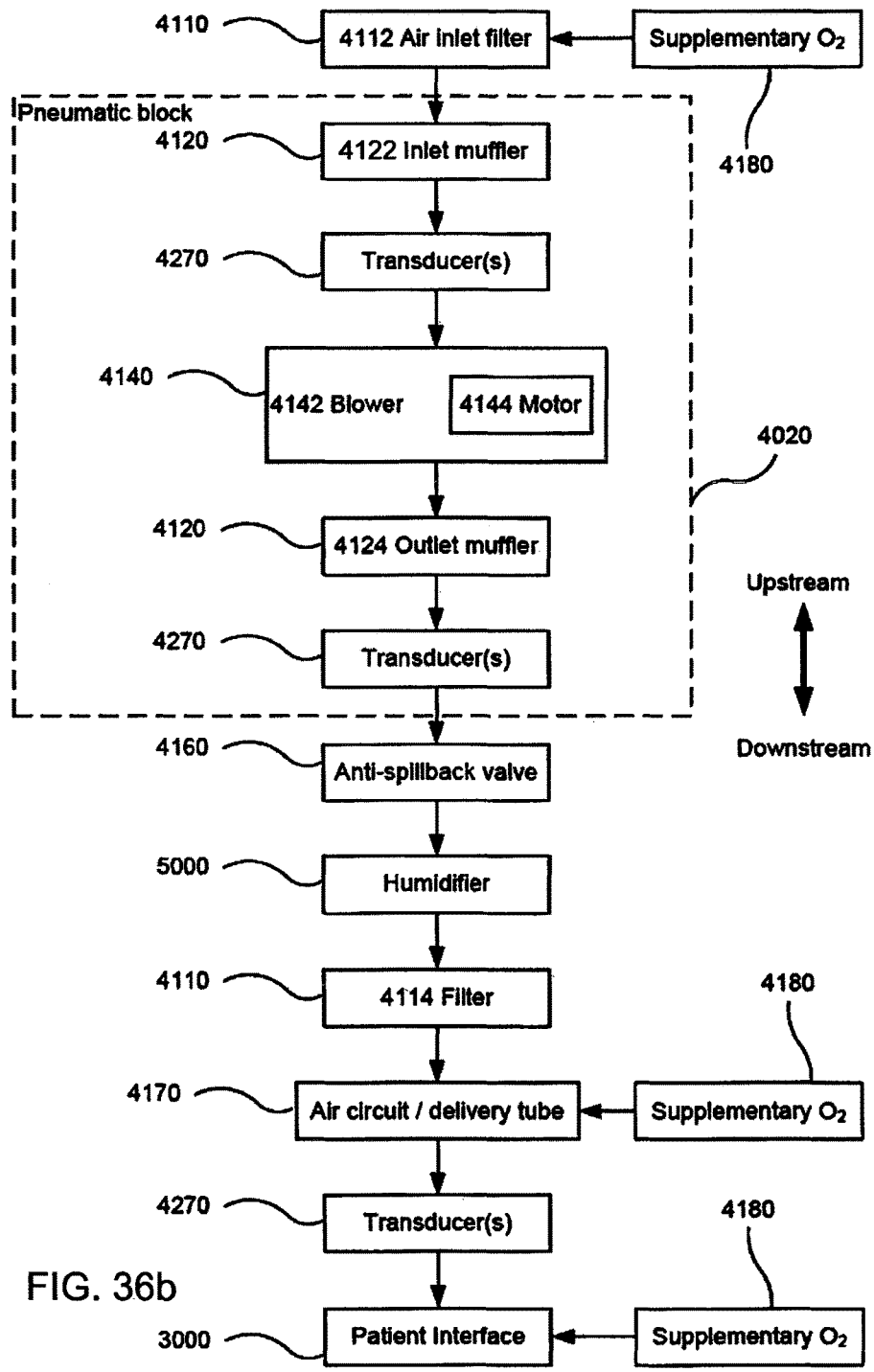
FIG. 36b shows a schematic diagram of the pneumatic circuit of a PAP device of FIG. 36a. The directions of upstream and downstream are indicated.
Figure 36C:
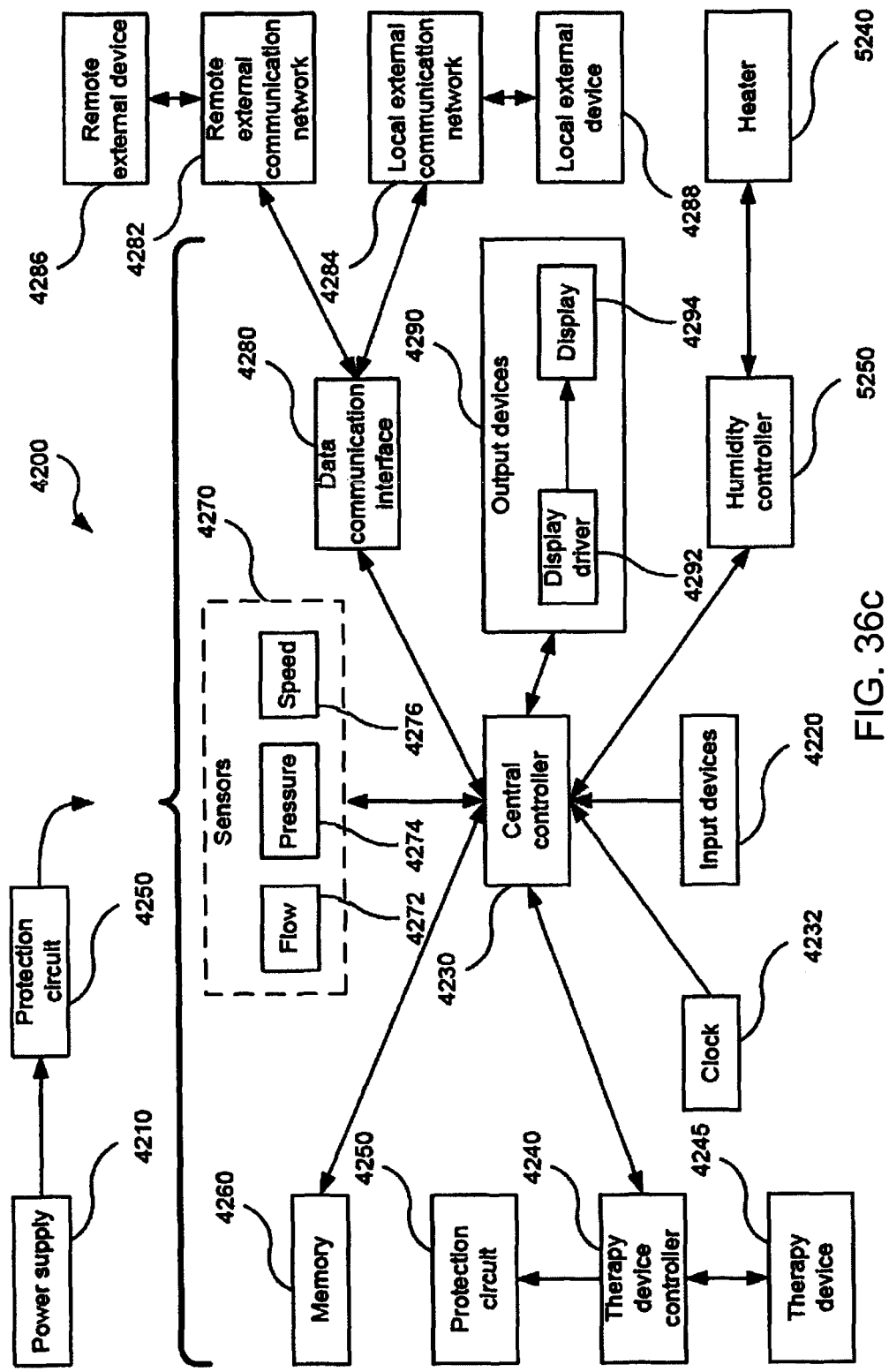

As illustrated in FIGS. 36*a*, 36*b* and 36*c*, an example PAP device 4000 in accordance with one aspect of the present technology may include mechanical and pneumatic components 4100, electrical components 4200 and may be programmed to execute one or more algorithms so as to generate the higher pressures that may be necessary for providing air via the smaller delivery circuits described herein. The PAP device may have an external housing 4010 formed in two parts, an upper portion 4012 of the external housing 4010, and a lower portion 4014 of the external housing 4010. In alternative forms, the external housing 4010 may include one or more panel(s) 4015. The PAP device 4000 may include a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 may include an inlet air filter 4112, an inlet muffler 4122, a controllable pressure device 4140 capable of supplying air at positive pressure (preferably a blower 4142), and an outlet muffler 4124. One or more pressure sensors (e.g., pressure transducer 4272) and flow sensors (e.g., flow transducer 4274) may optionally be included in the pneumatic path.

The pneumatic block 4020 comprises a portion of the pneumatic path that is located within the external housing 4010.

The PAP device 4000 has an electrical power supply 4210, one or more input devices 4220, a central controller 4230, one or more a therapy device controller(s) 4240, one or more therapy device(s) 4245, one or more protection circuits 4250, memory 4260, optional transducers 4270, data communication interface 4280 and one or more output devices 4290. Electrical components 4200 may be mounted on a single Printed Circuit Board Assembly (PCBA) 4202. In an alternative form, the PAP device 4000 may include more than one PCBA 4202.

The central controller 4230 of the PAP device 4000 may be programmed to execute one or more algorithm modules, including in one implementation a pre-processing module, a therapy engine module, a pressure control module, and a fault condition module.

In what follows, the PAP device 4000 is referred to interchangeably as a ventilator.

J.4.1 PAP Device Mechanical & Pneumatic Components 4100

J.4.1.1 Air Filter(s) 4110

A PAP device in accordance with one form of the present technology may include an air filter 4110, or a plurality of air filters 4110.

In one form, an inlet air filter 4112 is located at the beginning of the pneumatic path upstream of a blower 4142. See FIG. 36b.

In one form, an outlet air filter 4114, for example an antibacterial filter, is located between an outlet of the pneumatic block 4020 and a patient interface 3000. See FIG. 36b.

J.4.1.2 Muffler(s) 4120

In one form of the present technology, an inlet muffler 4122 is located in the pneumatic path upstream of a blower 4142. See FIG. 36b.

In one form of the present technology, an outlet muffler 4124 is located in the pneumatic path between the blower 4142 and a patient interface 3000. See FIG. 36b.

J.4.1.3 Pressure Device 4140

In one form of the present technology, a pressure device 4140 for producing a flow of air at positive pressure is a controllable blower 4142. For example, the blower may include a brushless DC motor 4144 with one or more impellers housed in a volute. The blower is capable of delivering a supply of air, at the levels previously described herein.

The pressure device 4140 may be under the control of the therapy device controller 4240 which may include or communicate with the treatment compensator controller described herein.

J.4.1.4 Transducer(s) 4270

In one form of the present technology, one or more transducers 4270 may be located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000, such as near or within the treatment compensator.

J.4.1.5 Anti-Spill Back Valve 4160

In one form of the present technology, an anti-spill back valve may be located between the humidifier 5000 and the pneumatic block 4020. The anti-spill back valve is constructed and arranged to reduce the risk that water will flow upstream from the humidifier 5000, for example to the motor 4144.

J.4.1.6 Air Circuit 4170

An air circuit 4170 in accordance with an aspect of the present technology is constructed and arranged to allow a flow of air or breathable gasses between the pneumatic block 4020 and the patient interface 3000 such as the delivery conduits previously described.

J.4.1.7 Oxygen Delivery

In one form of the present technology, supplemental oxygen 4180 may be delivered to a point in the pneumatic path.

In one form of the present technology, supplemental oxygen 4180 is delivered upstream of the pneumatic block 4020.

In one form of the present technology, supplemental oxygen 4180 is delivered to the air circuit 4170.

In one form of the present technology, supplemental oxygen 4180 is delivered to the patient interface 3000.

J.4.2 PAP Device Electrical Components 4200

J.4.2.1 Power Supply 4210

In one form of the present technology power supply 4210 is internal of the external housing 4010 of the PAP device 4000. In another form of the present technology, power supply 4210 is external of the external housing 4010 of the PAP device 4000.

In one form of the present technology power supply 4210 provides electrical power to the PAP device 4000 only. In another form of the present technology, power supply 4210 provides electrical power to both PAP device 4000 and humidifier 5000.

J.4.2.2 Input Devices 4220

In one form of the present technology, a PAP device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input, device 4220 may be constructed and arranged to allow a person to select a value and/or a menu option.

J.4.2.3 Central Controller 4230

In one form of the present technology, a central controller 4230 may be included which may be a processor suitable to control a PAP device 4000 and/or treatment compensator such as an x86 INTEL processor.

Such a processor suitable to control the device in accordance with another form of the present technology includes a processor based on ARM Cortex-M processor from ARM Holdings. For example, an STM32 series microcontroller from ST MICROELECTRONICS may be used.

Another processor suitable to control the apparatus in accordance with a further alternative form of the present technology includes a member selected from the family ARM9-based 32-bit RISC CPUs. For example, an STR9 series microcontroller from ST MICROELECTRONICS may be used. In certain alternative forms of the present technology, a 16-bit RISC CPU may be used as the processor for the PAP device 4000. For example a processor from the MSP430 family of microcontrollers, manufactured by TEXAS INSTRUMENTS, may be used.

The processor is configured to receive input signal(s) from one or more transducers 4270, and one or more input devices 4220 such as those described herein.

The processor is configured to provide output signal(s) to one or more of an output device 4290, a therapy device controller 4240, a data communication interface 4280 and humidifier controller 5250.

The processor, or multiple such processors, may be configured to implement one or more methodologies described herein such as one or more algorithms expressed as computer programs stored in memory 4260. In some cases, as previously discussed, such processor(s) may be integrated with a PAP device 4000 or treatment compensator 105. However, in some devices the processor(s) may be implemented discretely from the flow generation components of the PAP device, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein.

J.4.2.4 Clock 4232

Preferably PAP device 4000 includes a clock 4232 that is connected to processor.

J.4.2.5 Therapy Device Controller 4240

In one form of the present technology, therapy device controller 4240 is a pressure control module that forms part of the algorithms executed by the processor such as of the central controller.

In one form of the present technology, therapy device controller 4240 may include a dedicated motor control integrated circuit. For example, in one form a MC33035 brushless DC motor controller, manufactured by ONSEMI is used. In some embodiments, the therapy device controller 4240 may include one or more of the components of FIG. 17.

J.4.2.6 Protection Circuits 4250

Optionally a PAP device 4000 in accordance with the present technology includes one or more protection circuits 4250.

One form of protection circuit 4250 in accordance with the present technology is an electrical protection circuit.

One form of protection circuit 4250 in accordance with the present technology is a temperature or pressure safety circuit.

J.4.2.7 Memory 4260

In accordance with one form of the present technology the PAP device 4000 and/or treatment compensator includes memory 4260, preferably non-volatile memory. In some forms, memory 4260 may include battery powered static RAM. In some forms, memory 4260 may include volatile RAM.

Preferably memory 4260 is located on PCBA 4202. Memory 4260 may be in the form of EEPROM, or NAND flash.

Additionally or alternatively, PAP device 4000 and/or treatment compensator includes removable form of memory 4260, for example a memory card made in accordance with the Secure Digital (SD) standard.

J.4.2.8 Transducers 4270

Optional transducers may be internal of the device, or external of the PAP device. External transducers may be located for example on or form part of the air delivery circuit, e.g. the patient interface and/or the treatment compensator. External transducers may be in the form of non-contact sensors such as a Doppler radar movement sensor that transmit or transfer data to the PAP device.

J.4.2.8.1 Flow 4274

An optional flow transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In use, a signal or total flow Qt signal, from the flow transducer 4274, is received by a processor. However, other sensors for producing such a flow signal or estimating flow may be implemented. For example, a mass flow sensor, such as a hot wire mass flow sensor, may be implemented to generate a flow signal in some embodiments. Optionally, flow may be estimated from one or more signals of other sensors described here, such as in accordance with any of the methodologies described in a U.S. patent application Ser. No. 12/192,247, the disclosure of which is incorporated herein by reference.

J.4.2.8.2 Pressure

One or more optional pressure transducer 4272 in accordance with the present technology may be located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272, is received by a processor or controller described herein. In one form, the signal from the pressure transducer 4272 is filtered prior to being received by the processor.

J.4.2.8.3 Motor Speed

In one form of the present technology motor speed signal 4276 may be generated. A motor speed signal 4276 may be provided by therapy device controller 4240. Motor speed may, for example, be generated by an optional speed sensor, such as a Hall effect sensor, or inferred from back EMF as previously described.

J.4.2.9 Data Communication Systems

In one form of the present technology, a data communication interface 4280 is provided, and is connected to any of the processors described herein. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of processor. In another form, data communication interface 4280 is an integrated circuit that is separate from processor.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

J.4.2.10 Output Devices 4290 Including Optional Display, Alarms, Etc.

An output device 4290 in accordance with the present technology may take the form of one or more of a visual, audio and haptic unit. A visual display may be a Liquid Crystal Display (LCD) or Light Emitting Diode (LED) display.

J.4.2.10.1 Display Driver 4292

A display driver 4292 receives as an input the characters, symbols, or images intended for display on the display 4294, and converts them to commands that cause the display 4294 to display those characters, symbols, or images.

J.4.2.10.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

J.4.2.11 Therapy Device 4245

In a preferred form of the present technology, the therapy device 4245 is under the control of or formed as part of a controller to deliver therapy to a patient 1000 or otherwise generate them and then compensate them for delivery as described herein.

In some cases, the therapy device 4245 may include a positive air pressure device 4140.

J.5 Humidifier 5000

Figure 37:
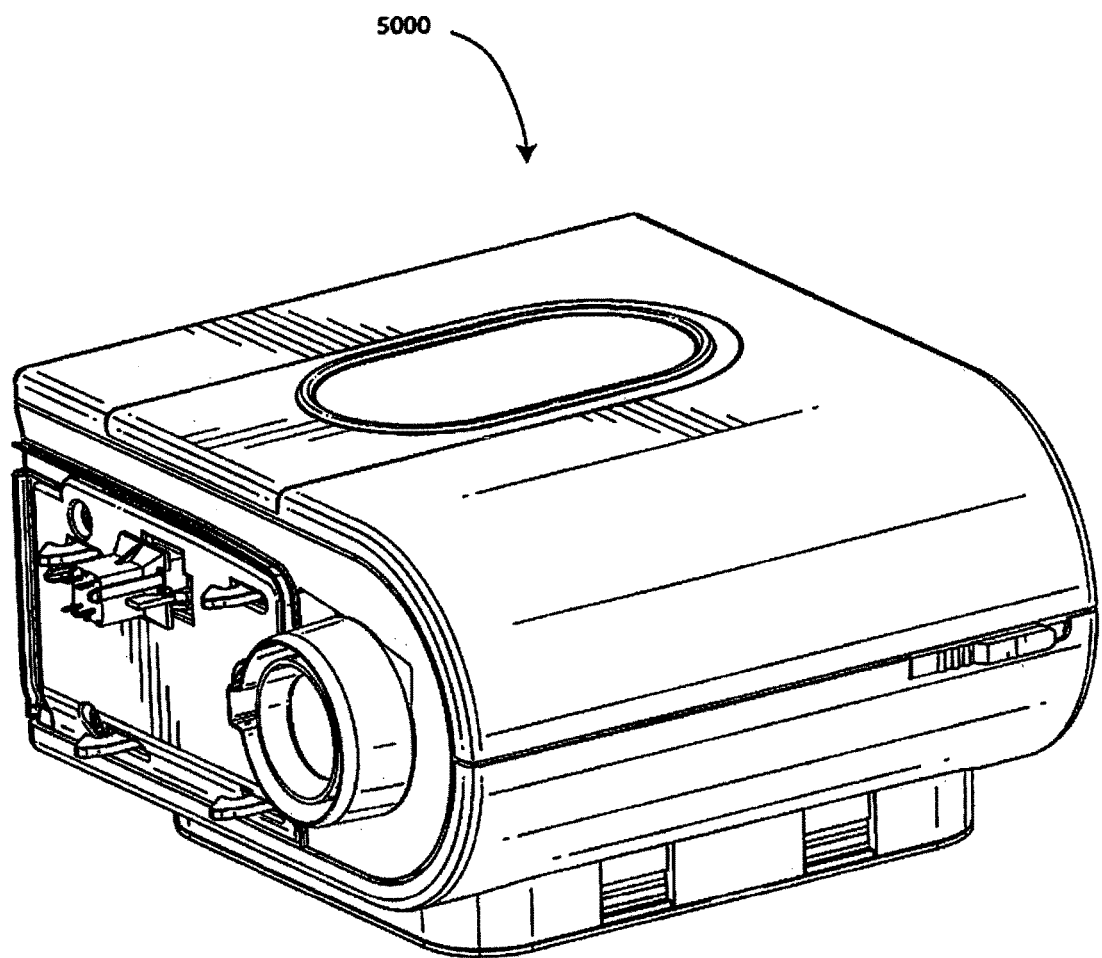
FIG. 37 shows a humidifier in accordance with one aspect of the present technology.

In one form of the present technology there is provided a humidifier 5000, such as the example illustrated in FIG. 37. The humidifier may include a water reservoir and a heating plate 5240 as shown in FIG. 36*c*.

H. Additional Technology Examples

Although the technology herein has been described with reference to particular embodiments, it is to be understood that these embodiments are merely illustrative of its principles and applications. It is therefore to be understood that numerous modifications may be made to the illustrative embodiments and that other arrangements may be devised without departing from the spirit and scope of the present technology. For example, the technology may be implemented according to any one or more of the following.

Example 1

A respiratory treatment apparatus comprising:

a flow pressurizer apparatus configured to generate a pressurized flow of air through a fine bore delivery conduit toward a patient interface;

a treatment compensator coupled with the fine bore delivery conduit and configured at the patient interface to reduce a first pressure to a second pressure for patient inspiration above atmospheric pressure; and a processor configured to control adjustments to the first pressure generated by the flow pressurizer apparatus and/or the second pressure of the treatment compensator.

Example 2

The respiratory treatment apparatus of Example 1 wherein the treatment compensator comprises a proportional valve.

Example 3

The respiratory treatment apparatus of Example 2 wherein the proportional valve comprises a high pressure inlet chamber coupled with the fine bore delivery conduit and a low pressure outlet chamber coupled with the patient interface, the high pressure inlet chamber for the first pressure and the low pressure outlet chamber for the second pressure.

Example 4

The respiratory treatment apparatus of any one of Examples 2-3 wherein the treatment compensator includes a solenoid.

Example 5

The respiratory treatment apparatus of any one of Examples 2-4 wherein the treatment compensator includes a pressure sensor, the sensor configured to sense the second pressure reduced by the treatment compensator.

Example 6

The respiratory treatment apparatus of any one of Examples 2-5 wherein the treatment compensator includes an actuator to adjust the proportional valve, and wherein the treatment compensator includes a pressure sensor.

Example 7

The respiratory treatment apparatus of any one of Examples 2-6 wherein the processor is configured to control an actuator to adjust the proportional valve so as to control a measure of the second pressure from a pressure sensor of the treatment compensator to meet a target pressure.

Example 8

The respiratory treatment apparatus of Example 7 wherein the treatment compensator includes a controller with the processor.

Example 9

The respiratory treatment apparatus of Example 8 wherein the controller includes an output driver for the actuator and an error evaluation unit to generate an error signal for the processor based on a signal representing a measure of pressure from the pressure sensor and a signal representing a target pressure.

Example 10

The respiratory treatment apparatus of Example 9 wherein the controller further includes a pressure signal processor.

Example 11

The respiratory treatment apparatus of any one of Examples 1-9 wherein the treatment compensator further includes a relief valve to release pressure of the treatment compensator to atmosphere.

Example 12

The respiratory treatment apparatus of Examples 11 wherein a controller of the treatment compensator sets an operation of the relief valve in response to a detected pressure.

Example 13

The respiratory treatment apparatus of any one of Examples 1-12 wherein the flow pressurizer apparatus comprises a first stage blower and second stage blower, an outlet of the first stage blower being coupled with an inlet of the second stage blower and an outlet of the second stage blower coupled with the fine bore delivery conduit.

Example 14

The respiratory treatment apparatus of Example 13 wherein the flow pressurizer apparatus further comprises a bypass conduit coupling the outlet of the second stage blower with an inlet of the first stage blower, the bypass conduit coupled with a flow diverter to selectively permit flow through the bypass conduit.

Example 15

The respiratory treatment apparatus of any one of Examples 1-14 wherein the treatment compensator further comprises a step down surface with a set of orifices between a high pressure inlet chamber, coupled with the fine bore delivery conduit, and a low pressure outlet chamber, coupled with the patient interface.

Example 16

The respiratory treatment apparatus of Example 15 wherein the treatment compensator further comprises a seal to selectively open and close the set of orifices.

Example 17

The respiratory treatment apparatus of Example 16 wherein movement of the seal is controlled by the processor to satisfy a target pressure.

Example 18

The respiratory treatment apparatus of any one of Examples 16-17 wherein the step down surface comprises a plurality of orifices.

Example 19

The respiratory treatment apparatus of Example 18, wherein each of the plurality of orifices comprises a respective boss raised above the step down surface.

Example 20

The respiratory treatment apparatus of any one of Examples 16-19 wherein the step down surface further includes a plurality of channels about a periphery of the step down surface.

Example 21

The respiratory treatment apparatus of any one of Examples 1-20 further comprising a pressure tank reservoir coupled with the fine bore delivery conduit proximate to the flow pressurizer apparatus, the reservoir configured to pressurize the gas of the fine bore delivery conduit during peak operations and charge from it during low flow operations.

Example 22

The respiratory treatment apparatus of Example 21 further comprising a pressure regulator to limit pressure entering the fine bore delivery conduit from the reservoir.

Example 23

The respiratory treatment apparatus of Example 22 further comprising a secondary pressure reservoir proximate to the treatment compensator.

Example 24

The respiratory treatment apparatus of any one of Examples 1-23 wherein the flow pressurizer apparatus is configured to generate air pressures in a range of about 70 cm $H_2O$ to 140 cm $H_2O$.

Example 25

The respiratory treatment apparatus of any one of Examples 1-24 wherein the treatment compensator is configured to reduce pressures to a range of about 2-40 cm $H_2O$.

Example 26

The respiratory treatment apparatus of any one of Examples 1-25 wherein fine bore delivery conduit is a delivery tube with an outside diameter in a range of about 7 mm to 10 mm.

Example 27

The respiratory treatment apparatus of Example 1 wherein the treatment compensator comprises a divider valve.

Example 28

The respiratory treatment apparatus of Example 27 wherein the divider valve comprises a multi-sectional piston.

Example 29

The respiratory treatment apparatus of any one of Examples 27-28 wherein the divider valve comprises a first piston chamber and a second piston chamber, the first piston chamber in gas communication with the fine bore conduit and the second piston chamber in gas communication with the patient interface.

Example 30

The respiratory treatment apparatus of Example 28 wherein movement of a piston coupled in the first piston chamber and the second piston chamber sets the reduced second pressure by a ratio of the first piston chamber and the second piston chamber.

Example 31

The respiratory treatment apparatus of Example 30 wherein the processor calculates a setting for control of the first pressure as a function of the ratio.

Example 32

The respiratory treatment apparatus of any one of Examples 1-30 wherein the patient interface comprises a mask with a vent.

Example 33

A pressure controller device for a respiratory treatment apparatus to reduce a first pressure of a flow pressurizer apparatus for patient inspiration to a second pressure above atmospheric pressure for a patient interface, the pressure controller device comprising:

a high pressure inlet adapted to couple with a gas pressurizer apparatus, the high pressure inlet coupled with a high pressure inlet chamber;

a low pressure outlet adapted to couple with a patient interface, the low pressure outlet coupled with a low pressure outlet chamber;

a pressure sensor to sense pressure of the low pressure outlet chamber and generate a signal representing pressure of the low pressure outlet;

a set of orifices on a step down surface between the high pressure inlet chamber and the low pressure outlet chamber;

an actuator seal configured to movably close and open the set of orifices, and a processor configured to control adjustments to the actuator seal based on the measure of pressure.

Example 34

The pressure controller device of Example 33 wherein the actuator seal comprises a sealing surface arranged to sealingly close and open the set of orifices when actuated by a solenoid.

Example 35

The pressure controller device of any one of Examples 33-34 wherein the processor is configured to control the actuator seal so as to control the measure of pressure to meet a target pressure.

Example 36

The pressure controller device of any one of Examples 33-35 further comprising an output driver for the actuator and an error evaluation unit to generate an error signal for the processor based on the signal representing the measure of pressure and a signal representing a target pressure.

Example 37

The pressure controller device of any one of Examples 33-36 further including a pressure signal processor to filter the signal representing pressure of the low pressure outlet.

Example 38

The pressure controller device of any one of Examples 33-37 further comprising a relief valve to release pressure to atmosphere.

Example 39

The pressure controller device of any one of Examples 33-38 wherein the processor sets an operation of the relief valve in response to a detected pressure.

Example 40

The pressure controller device of any one of Examples 33-39 wherein the step down surface further comprises a plurality of orifices.

Example 41

The pressure controller device of Example 40, wherein each of the plurality of orifices comprises a respective boss raised above the step down surface.

Example 42

The pressure controller device of any one of Examples 33-41 wherein the step down surface further includes a plurality of channels about a periphery of the step down surface.

Example 43

The pressure controller device of any one of Examples 33-42 further comprising a pilot flow conduit coupling the high pressure inlet chamber and an interior chamber, the interior chamber separated from the low pressure outlet chamber by a flexible diaphragm.

Example 44

The pressure controller device of any one of Examples 33-43 wherein the step down surface further includes an exhaust orifice to permit gas escape to atmosphere.

Example 45

A pressure controller device for a respiratory treatment apparatus to reduce a first pressure of a flow pressurizer apparatus to a second pressure for patient inspiration above atmospheric pressure, the controller device comprising:
  a high pressure inlet adapted to couple with a gas pressurizer apparatus, the high pressure inlet coupled with a high pressure inlet chamber;
  a low pressure outlet adapted to couple with a patient interface, the low pressure outlet coupled with a low pressure outlet chamber;
  a pressure sensor to sense pressure associated with the low pressure outlet chamber and generate a signal representing pressure; and
  a divider valve comprising a multi-sectional piston, a first piston chamber and a second piston chamber, the first piston chamber in gas communication with the high pressure inlet chamber and the second piston chamber in gas communication with the patient interface.

Example 46

The pressure controller device of Example 43 wherein movement of the multi-sectional piston coupled in the first piston chamber and the second piston chamber sets the reduced second pressure by a ratio of the first piston chamber and the second piston chamber.

Example 47

The pressure controller device of Example 44 further comprising a processor configured to calculate a setting for control of a pressure of the high pressure inlet chamber as a function of the ratio.

Example 48

The pressure controller device of any one of Examples 43-45 wherein the pressure controller device comprises a respiratory mask.

Example 49

The pressure controller device of any one of Examples 43-46 wherein the pressure controller device comprises a swivel elbow coupler.

Example 50

A gas pressure controller device to reduce a first pressure of a flow of gas to a second pressure, the pressure controller device comprising:
  a high pressure inlet, the high pressure inlet coupled with a high pressure inlet chamber;
  aglow pressure outlet, the low pressure outlet coupled with a low pressure outlet chamber;
  a set of orifices on a step down surface between the high pressure inlet chamber and the low pressure outlet chamber; and
  an actuator seal configured to movably adjust a size of a gap between the actuator seal and the set of orifices in response to a detected pressure so as to set the second pressure.

Example 51

The gas pressure controller device of Example 50 wherein an actuator of the actuator seal comprises a solenoid.

Example 52

The gas pressure controller device of any one of Examples 50-51 wherein the actuator seal comprises a platen seat ring.

Example 53

The gas pressure controller device of any one of Examples 50-52 wherein the step down surface further comprises a plurality of boss orifices raised above the step down surface.

Example 54

The gas pressure controller device of any one of Examples 50-53 wherein the step down surface further includes a plurality of channels about a periphery of the step down surface.

Example 55

The gas pressure controller device of any one of Examples 50-54 further comprising a pilot flow conduit coupling an interior chamber and the high pressure inlet chamber, the interior chamber separated from the low pressure outlet chamber by a flexible diaphragm.

Example 56

The gas pressure controller device of any one of Examples 50-55 wherein the step down surface further includes an exhaust orifice to permit gas escape to atmosphere.

Example 57

The gas pressure controller device of Example 56 wherein the exhaust orifice includes a traversable capillary tube.

Example 58

The gas pressure controller device of Example 57 wherein the capillary tube is in gas communication with an interior chamber, the interior chamber separated from the low pressure outlet chamber by a flexible diaphragm.

Example 59

The gas pressure controller device of Example 58 wherein the actuator seal further comprises a valve seat in the interior chamber, the valve seat coupled to a solenoid to selectively open and close an entrance to the capillary tube.

Example 60

The gas pressure controller device of Example 58 wherein positioning of the valve seat at the entrance to the capillary tube sets a pressure of the interior chamber that adjusts the actuator seal through movement of the diaphragm.

Example 61

The gas pressure controller device of any one of Examples 50 to 50 wherein the high pressure inlet is coupled with a flow pressurizer apparatus to generate a breathable gas at the first pressure.

Example 61

The gas pressure controller device of any one of Examples 50 to 61 wherein the low pressure outlet is coupled with a patient interface to deliver a breathable gas at the second pressure for a respiratory treatment.

Example 62

A flow control valve using servo pilot assistance comprising any one, some or all of:
a lower valve seat with multiple orifices, each orifice having a central flow axis, each central flow axis being generally parallel;
at least one high pressure inlet port to supply higher pressure fluid through the valve seat orifices;
at least one low pressure outlet port for lower pressure fluid to flow through the lower valve seat orifices;
a diaphragm assembly, with or without a center platen, to adapt with the lower valve seat orifices to close or restrict flow between the higher pressure inlet and the lower pressure outlet,
a pilot pressure chamber on top of the diaphragm assembly, the pilot pressure chamber to have a generally constant supply of fluid bled into the pilot chamber from a higher pressure source; and
a pilot valve to relieve fluid pressure from the pilot chamber, the pilot valve mechanically actuated by relative axial position of an externally positioned member and an axial position of the diaphragm assembly, wherein as the diaphragm assembly is raised away from the lower valve seat the pilot valve becomes more restricted, and wherein as the externally positioned member is raised upward the pilot valve becomes less restricted,
whereby movement of the diaphragm assembly follows movement of the externally positioned member, assisted by changes in the pressure in the pilot pressure chamber.

Example 62

The flow control valve of Example 61 wherein the pilot valve's externally positioned member is positioned with a solenoid.

Example 63

The flow control valve of any one of Examples 61-62 wherein each of the multiple orifices has a raised boss around its perimeter.

Example 64

The flow control valve of any one of Examples 61-63 wherein the low pressure outlet port is adapted to couple with a patient interface to deliver a breathable gas for a respiratory treatment.

Example 65

The flow control valve of any one of Examples 61-64 wherein the high pressure inlet port is adapted to couple with a flow pressurizer apparatus to receive a breathable gas for a respiratory treatment.

Example 66

A pressure control system comprising solenoid-actuated, pilot-assisted flow control valve with a structure of the flow control valve of any one of Examples 61-65, at least one sensor, and an at least one controller, the flow control valve, at sensor one sensor and at least one controller configured to provide closed-loop control to a fluid system connected to the flow control valve's low pressure outlet port.

The invention claimed is:
1. A respiratory treatment apparatus comprising:
a flow pressurizer apparatus configured to generate a pressurized flow of air through a fine bore delivery conduit toward a patient interface;
a treatment compensator coupled with the fine bore delivery conduit at the patient interface, and configured to reduce a first pressure to a second pressure for delivery to a patient from the treatment compensator, the second pressure being above atmospheric pressure; and
a processor configured to control adjustments to the first pressure generated by the flow pressurizer apparatus or the second pressure of the treatment compensator,
wherein the treatment compensator further comprises a step down surface with a set of orifices between a high pressure inlet chamber, coupled with the fine bore delivery conduit, and a low pressure outlet chamber, coupled with the patient interface,
wherein the treatment compensator further comprises a seal to selectively open and close the set of orifices,
wherein each of the set of orifices comprises a respective boss raised above the step down surface.

2. The respiratory treatment apparatus of claim 1 wherein the treatment compensator comprises a proportional valve.

3. The respiratory treatment apparatus of claim 2 wherein the proportional valve comprises a high pressure inlet chamber coupled with the fine bore delivery conduit and a low pressure outlet chamber coupled with the patient interface, the high pressure inlet chamber for the first pressure and the low pressure outlet chamber for the second pressure.

4. The respiratory treatment apparatus of claim 2 wherein the treatment compensator includes a solenoid.

5. The respiratory treatment apparatus of claim 2 wherein the treatment compensator includes a pressure sensor, the sensor configured to sense the second pressure reduced by the treatment compensator.

6. The respiratory treatment apparatus of claim 2 wherein the treatment compensator includes an actuator to adjust the proportional valve, and wherein the treatment compensator includes a pressure sensor.

7. The respiratory treatment apparatus of claim 2 wherein the processor is configured to control an actuator to adjust the proportional valve so as to control a measure of the second pressure from a pressure sensor of the treatment compensator to meet a target pressure.

8. The respiratory treatment apparatus of claim 6 wherein the treatment compensator includes a controller with the processor.

9. The respiratory treatment apparatus of claim 8 wherein the controller includes an output driver for the actuator and an error evaluation unit to generate an error signal for the processor based on a signal representing a measure of pressure from the pressure sensor and a signal representing a target pressure.

10. The respiratory treatment apparatus of claim 9 wherein the controller further includes a pressure signal processor.

11. The respiratory treatment apparatus of claim 1 wherein the treatment compensator further includes a relief valve to release pressure of the treatment compensator to atmosphere.

12. The respiratory treatment apparatus of claim 11 wherein a controller of the treatment compensator sets an operation of the relief valve in response to a detected pressure.

13. The respiratory treatment apparatus of claim 1 wherein the flow pressurizer apparatus comprises a first stage blower and second stage blower, an outlet of the first stage blower being coupled with an inlet of the second stage blower and an outlet of the second stage blower coupled with the fine bore delivery conduit.

14. The respiratory treatment apparatus of claim 13 wherein the flow pressurizer apparatus further comprises a bypass conduit coupling the outlet of the second stage blower with an inlet of the first stage blower, the bypass conduit coupled with a flow diverter to selectively permit flow through the bypass conduit.

15. The respiratory treatment apparatus of claim 1 wherein movement of the seal is controlled by the processor to satisfy a target pressure.

16. The respiratory treatment apparatus of claim 1 wherein the step down surface further includes a plurality of channels about a periphery of the step down surface.

17. The respiratory treatment apparatus of claim 1 further comprising a pressure tank reservoir coupled with the fine bore delivery conduit proximate to the flow pressurizer apparatus, the reservoir configured to pressurize the air of the fine bore delivery conduit during peak operations and charge from it during low flow operations.

18. The respiratory treatment apparatus of claim 17 further comprising a pressure regulator to limit pressure entering the fine bore delivery conduit from the reservoir.

19. The respiratory treatment apparatus of claim 18 further comprising a secondary pressure reservoir proximate to the treatment compensator.

20. The respiratory treatment apparatus of claim 1 wherein the flow pressurizer apparatus is configured to generate air pressures in a range of about 70 cm $H_2O$ to 140 cm $H_2O$.

21. The respiratory treatment apparatus of claim 1 wherein the treatment compensator is configured to reduce pressures to a range of about 2-40 cm $H_2O$.

22. The respiratory treatment apparatus of claim 1 wherein the fine bore delivery conduit is a delivery tube with an outside diameter in a range of about 7 mm to 10 mm.

23. The respiratory treatment apparatus of claim 1 wherein the patient interface comprises a mask with a vent.

24. The respiratory treatment apparatus of claim 1 wherein the processor is configured to control adjustments to the first pressure generated by the flow pressurizer apparatus and the reduction of pressure at the treatment compensator.

25. The respiratory treatment apparatus of claim 1 wherein the processor is configured to control adjustments to the reduction of pressure at the treatment compensator.

26. The respiratory treatment apparatus of claim 1 wherein the processor is configured to control adjustments to the first pressure generated by the flow pressurizer apparatus.

27. A respiratory treatment apparatus comprising:
a flow pressurizer apparatus configured to generate a pressurized flow of air through a fine bore delivery conduit toward a patient interface;
a treatment compensator coupled with the fine bore delivery conduit at the patient interface, and configured to reduce a first pressure to a second pressure for delivery to a patient from the treatment compensator, the second pressure being above atmospheric pressure; and
a processor configured to control adjustments to the first pressure generated by the flow pressurizer apparatus or the second pressure of the treatment compensator,
wherein the treatment compensator further comprises a step down surface with a set of orifices between a high pressure inlet chamber, coupled with the fine bore delivery conduit, and a low pressure outlet chamber, coupled with the patient interface,
wherein the treatment compensator further comprises a seal to selectively open and close the set of orifices,
wherein the step down surface further includes a plurality of channels about a periphery of the step down surface.

* * * * *